(12) United States Patent
Gasperino et al.

(10) Patent No.: US 10,549,273 B2
(45) Date of Patent: Feb. 4, 2020

(54) FLOW ASSAY WITH AT LEAST ONE ELECTRICALLY-ACTUATED FLUID FLOW CONTROL VALVE AND RELATED METHODS

(71) Applicant: Tokitae LLC, Bellevue, WA (US)

(72) Inventors: David Gasperino, Lake Forest Park, WA (US); Kevin Paul Flood Nichols, Issaquah, WA (US); Bernhard Hans Weigl, Seattle, WA (US); Benjamin K. Wilson, Kirkland, WA (US); Ozgur Emek Yildirim, Bellevue, WA (US)

(73) Assignee: Tokitae LLC, Bellevue, WA (US)

( * ) Notice: Subject to any disclaimer, the term of this patent is extended or adjusted under 35 U.S.C. 154(b) by 371 days.

(21) Appl. No.: 15/482,593

(22) Filed: Apr. 7, 2017

(65) Prior Publication Data

US 2017/0212109 A1 Jul. 27, 2017

Related U.S. Application Data

(63) Continuation-in-part of application No. 14/490,956, filed on Sep. 19, 2014, now Pat. No. 9,638,685.

(51) Int. Cl.
*B01L 3/00* (2006.01)
*G01N 33/487* (2006.01)
*G01N 21/84* (2006.01)

(52) U.S. Cl.
CPC ....... *B01L 3/5023* (2013.01); *B01L 3/502738* (2013.01); *G01N 33/48707* (2013.01); *B01L 2300/0645* (2013.01); *B01L 2300/0825* (2013.01); *B01L 2400/0406* (2013.01); *B01L 2400/0427* (2013.01); *B01L 2400/0688* (2013.01); *G01N 21/8483* (2013.01)

(58) Field of Classification Search
CPC ............ B01L 3/5023; B01L 3/502738; B01L 2400/0688; B01L 2400/0427; B01L 2400/0406; B01L 2300/0825; B01L 2300/0645; G01N 33/48707; G01N 21/8483

See application file for complete search history.

(56) References Cited

U.S. PATENT DOCUMENTS

| | | | |
|---|---|---|---|
| 7,216,660 B2 | 5/2007 | Troian et al. | |
| 7,264,337 B2 | 9/2007 | Lee et al. | |
| 8,037,903 B2 | 10/2011 | Wang et al. | |
| 8,356,631 B2 | 1/2013 | Suzuki et al. | |

(Continued)

FOREIGN PATENT DOCUMENTS

| | | |
|---|---|---|
| WO | 2014033329 | 3/2014 |
| WO | 2016044080 | 3/2016 |

OTHER PUBLICATIONS

T. Merian, et al., "Development and surface characterization of an electrowetting valve for capillary-driven microfluidics", Colloids and Surfaces A: Physiochemical and Engineering Aspects, 414: p. 251-258, Nov. (Year: 2012).*

(Continued)

*Primary Examiner* — J. Christopher Ball
(74) *Attorney, Agent, or Firm* — Dorsey & Whitney LLP

(57) ABSTRACT

Embodiments disclosed herein are directed to flow assays including at least one electrically-actuated valve configured to control fluid flow. Methods of operating such flow assays are also disclosed.

39 Claims, 17 Drawing Sheets

(56) References Cited

U.S. PATENT DOCUMENTS

| | | |
|---|---|---|
| 2002/0166592 A1 | 11/2002 | Liu et al. |
| 2004/0011648 A1 | 1/2004 | Paul et al. |
| 2004/0067166 A1 | 4/2004 | Karinka et al. |
| 2005/0136550 A1 | 6/2005 | Yang et al. |
| 2005/0230252 A1 | 10/2005 | Tsai et al. |
| 2008/0257438 A1 | 10/2008 | Wang et al. |
| 2010/0159599 A1 | 6/2010 | Song et al. |
| 2010/0200073 A1 | 8/2010 | Suzuki |
| 2011/0185827 A1 | 8/2011 | Asano et al. |
| 2012/0181184 A1 | 7/2012 | Whitesides et al. |
| 2012/0273053 A1 | 11/2012 | Murphy et al. |
| 2013/0087459 A1 | 4/2013 | Kong et al. |
| 2013/0128036 A1 | 5/2013 | Whitesides et al. |
| 2013/0330713 A1 | 12/2013 | Jakubowicz et al. |
| 2016/0084796 A1 | 3/2016 | Gasperino et al. |

OTHER PUBLICATIONS

European Patent Office, Extended European Search Report, Pursuant to Rule 62 EPC; App. No. EP 15 84 1137; Mar. 20, 2018; pp. 1-9.

Gerbers et al.; "A new paper-based platform technology for point-of-care diagnostics"; Lab Chip; Aug. 15, 2014; pp. 4042-4049; vol. 14; Royal Society of Chemistry 2014.

He,Fei; "Development of capillary-driven microfluidic biosensors for food safety and quality assurance"; (2014). Doctoral Dissertations May 2014—current, 9; located at http://scholarworks.umass.edu/dissertations_2/9.

Koo et al; "An inkjet-printed electrowetting valve for paper-fluidic sensors"; Analyst; Jun. 17, 2013; pp. 4998-5004; vol. 138; Royal Society of Chemistry 2013.

Nashida et al.; "Electrochemical immunoassay on a microfluidic device with sequential injection and flushing functions"; Biosensors and Bioelectronics; Feb. 13, 2007; vol. 22; pp. 3167-3173; Elsevier B.V. 2007.

Tang et al.; "Paper-based electrochemical immunoassay for rapid, inexpensive cancer biomarker protein detection"; Anal. Methods; Sep. 10, 2014; pp. 8878-8881; vol. 6, Royal Society of Chemistry 2014.

Yamaguchi et al.; "Electrowetting-based pH- and biomolecule-responsive valves and pH filters"; Biosensors and Bioelectronics; Nov. 19, 2008; pp. 2171-2176; vol. 24; Elsevier B.V.

PCT International Search Report; International App. No. PCT/US2018/026195; dated Jul. 26, 2018; pp. 1-4.

U.S. Appl. No. 14/490,956, filed Sep. 19, 2014, Gasperino.

PCT International Search Report; International App. No. PCT/US2015/049590; Dec. 22, 2015; DD. 1-3.

Esquivel et al. "Microfluidic fuel cells on paper: meeting the power needs of next generation lateral flow devices" Energy and Environmental Science, 2014, 7, 1744-1749.

Ko et al. "Active Digital Microfluidic Paper Chips with Inkjet-Printed Patterned Electrodes" Advanced Materials, 2014, 26, 2335-2340.

Ren et al. "Automated on-chip droplet dispensing with volume control by electro-wetting actuation and capacitance metering" Sensors and Actuators B 98 (2004) 319-327.

Toley et al. "Tunable-Delay Shunts for Paper Microfluidic Devices" Analytical Chemistry, 2013, D 85, 11545-11552.

Yeo et al. "Electrowetting, Applications" Department of Mechanical Engineering, Monash University, 2008, pp. 606-615.

\* cited by examiner

FLOW ASSAY WITH AT LEAST ONE ELECTRICALLY-ACTUATED FLUID FLOW CONTROL VALVE AND RELATED METHODS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application is related to and/or claims the benefit of the earliest available effective filing date(s) from the following listed application(s) (the "Priority Applications"), if any, listed below (e.g., claims earliest available priority dates for other than provisional patent applications or claims benefits under 35 U.S.C § 119(e) for provisional patent applications, for any and all parent, grandparent, great-grandparent, etc. applications of the Priority Application(s)). In addition, the present application is related to the "Related Applications," if any, listed below.

PRIORITY APPLICATIONS

For purposes of the USPTO extra-statutory requirements, the present application constitutes a continuation-in-part of U.S. patent application Ser. No. 14/490,956, entitled flow Assay with at least one ELECTRICALLY-ACTUATED FLUID FLOW CONTROL VALVE AND RELATED METHODS, naming David Gasperino; Kevin Paul Flood Nichols; Benjamin K. Wilson; and Ozgur Emek Yildirim as inventors, filed on 19 Sep. 2014, which is currently co-pending or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed Application, USPTO Official Gazette Mar. 18, 2003. The USPTO further has provided forms for the Application Data Sheet which allow automatic loading of bibliographic data but which require identification of each application as a continuation, continuation-in-part, or divisional of a parent application. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above and in any ADS filed in this application, but expressly points out that such designation(s) are not to be construed in any way as any type of commentary and/or admission as to whether or not the present application contains any new matter in addition to the matter of its parent application(s).

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

BACKGROUND

A lateral flow assay ("LFA") can be a paper-based device that detects a presence of an analyte in a sample without the need for costly equipment. LFAs are a common point of care diagnostic tool.

LFAs function by wicking (e.g., capillary action) a sample of interest through a porous membrane (e.g. paper) where chemical reactions can occur in and on the surface of the porous membrane. The LFA can contain a conjugate material therein. Conjugate materials are typically formulated to provide the solvent(s) and reactant(s) necessary to dissolve, react, color, tag, or bond to the suspected analyte in a sample. Thus, if the analyte is present, the conjugate or a component thereof will react with the analyte in the sample. The conjugate can include a taggant or other material configured to provide a visual indication of the presence of the analyte, reacted analyte, or analyte-conjugate complex. Typically, the readout of an LFA is a visual change at some point along a length of the LFA. Many LFAs include an analyte collection material near the distal end of the LFA whereby the analyte and any taggant bonded thereto are bound in large concentration to provide visual indication of a positive or negative result.

LFAs can have limited flow control so that once the liquid enters a LFA, the liquid continues flowing through capillary action at a predetermined rate at least partially governed by the Lucas-Washburn equation. Without flow control, the complexity of chemical reactions that can be carried out in an LFA is limited.

SUMMARY

Embodiments disclosed herein are directed to fluid assays (e.g., LFAs) including an electrically-actuated valve configured to control fluid flow. Methods of operating such fluid assays are also disclosed.

In an embodiment, a flow assay for detecting a presence of an analyte in a sample is disclosed. The flow assay includes at least one hydrophilic porous layer having a proximal end through which the sample can be introduced, a distal end spaced from the proximal end, a first side spaced from a second side, and a gap located between the proximal end and the distal end and located between the first side and the second side. The flow assay includes at least one first hydrophobic layer disposed adjacent to the first side of the at least one hydrophilic porous layer to partially define the gap and at least one second hydrophobic layer disposed adjacent to the second side of the at least one hydrophilic porous layer to partially define the gap. The flow assay further includes a first electrode electrically coupled to the at least one first hydrophobic layer and separated from the at least one hydrophilic porous layer by the at least one first hydrophobic layer and a second electrode electrically coupled to the at least one second hydrophobic layer and separated from the at least one hydrophilic porous layer by the at least one second hydrophobic layer. The flow assay also includes a power source electrically coupled to the first and second electrodes, the power source configured to apply a voltage between the first electrode and the second electrode.

In an embodiment, a method of detecting a presence of an analyte in a sample is disclosed. The method includes providing a flow assay including at least one hydrophilic porous layer having a proximal end through which the sample can be introduced, a distal end spaced from the proximal end, a first side spaced from a second side, and a gap located between the proximal end and the distal end and located between the first side and the second side. The provided flow assay includes at least one first hydrophobic layer disposed adjacent to the first side of the at least one hydrophilic porous layer to partially define the gap and at least one second hydrophobic layer disposed adjacent to the second side of the at least one hydrophilic porous layer to partially define the gap. The provided flow assay also includes a first electrode electrically coupled to the at least one first hydrophobic layer and separated from the at least one hydrophilic porous layer by the at least one first hydrophobic layer, a second electrode electrically coupled to the at least one second hydrophobic layer and separated from the at least one hydrophilic porous layer by the at least one second hydrophobic layer, and a power source electrically coupled to the first and second electrodes. The method includes introducing the sample at the proximal end of the at least one hydrophilic porous layer of the flow assay. The method further includes applying a voltage between the first electrode and the second electrode effective to alter a hydrophobicity of at least one of the at least one first hydrophobic layer or the at least one second hydrophobic layer.

In an embodiment, a flow assay is disclosed. The flow assay includes at least one common area. The flow assay also includes at least one first branch and at least one second branch extending longitudinally from and fluidly coupled to the at least one common area. Each of the at least one first branch and the at least one second branch includes at least one hydrophilic porous layer including a proximal branch end adjacent to the at least one common area, a distal branch end spaced from the proximal branch end, a first branch side spaced from a second branch end, and at least one gap located between the proximal branch end and the distal branch end. Each of the at least one first branch and the at least one second branch can also include at least one first hydrophobic layer disposed adjacent to the first branch side to partially define the at least one gap, at least one second hydrophobic layer disposed adjacent to the second branch side to partially define the at least one gap, a first electrode separated from the at least one hydrophilic porous layer by the at least one first hydrophobic layer; and a second electrode separated from the at least one hydrophilic porous layer by the at least one second hydrophobic layer. Also, the flow assay includes a power source electrically coupled to the first and second electrodes. The power source is configured to generate a first voltage between the first electrode and the second electrode of the at least one first branch to enable at least a portion of the sample to flow across the at least one gap of the at least one first branch. The power source is also configured to generate a second voltage between the first electrode and the second electrode of the at least one second branch to enable at least a portion of the sample flow across the at least one gap of the at least one second branch, wherein the second voltage is different than the first voltage.

In an embodiment, a method to detect a presence of at least one analyte in a sample is disclosed. The method includes flowing the sample through at least one first branch. Flowing the sample through at least one first branch includes flowing the sample from a first proximal branch end of at least one hydrophilic porous layer of the at least one first branch to at least one first gap. The at least one first gap is located between the first proximal branch end and a first distal branch end that is spaced from the first proximal branch end. The at least one hydrophilic porous layer of the at least one first branch includes a first branch side spaced from a second branch side. Flowing the sample through at least one first branch also includes preventing the flow of the sample across the at least one first gap because of at least at least one first hydrophobic layer that is disposed adjacent to the first branch side and partially defining the at least one first gap and at least one second hydrophobic layer that is disposed adjacent to the second branch side and partially defining the at least one first gap. Flowing the sample through at least one first branch further includes, after preventing the flow of the sample across the at least one first gap, applying a first voltage between a first electrode and a second electrode effective to alter a hydrophobicity of the at least one first hydrophobic layer or the at least one second hydrophobic layer. The first electrode is separated from the at least one first hydrophilic porous layer of the at least one first branch by the at least one first hydrophobic layer and the second electrode is separated from the at least one first hydrophilic porous layer of the at least one first branch by the at least one second hydrophobic layer. Also, flowing the sample through at least one first branch includes, responsive to applying a first voltage between a first electrode and a second electrode, enabling at least a portion of the sample to flow across the at least one first gap. The method also includes flowing the sample at least partially through at least one second branch. Flowing the sample at least partially through at least one second branch includes flowing the sample from a second proximal branch end of at least one hydrophilic porous layer of the at least one second branch to at least one second gap. The at least one second gap is located between the second proximal branch end and a second distal branch end that is spaced from the second proximal branch end. The at least one hydrophilic porous layer of the at least one second branch includes a third branch side spaced from a fourth branch side. Flowing the sample at least partially through at least one second branch further includes preventing the flow of the sample across the at least one second gap because of at least at least one first hydrophobic layer that is disposed adjacent to the third branch side to partially define the at least one second gap at least one second hydrophobic layer that is disposed adjacent to the fourth branch side to partially define the at least one second gap.

In an embodiment, a flow assay for detecting a presence of an analyte in a sample is disclosed. The flow assay includes at least one common area. The flow assay also includes at least one first branch and at least one second branch extending longitudinally from the at least one common area. Each of the at least one first branch and the at least one second branch includes at least one hydrophilic porous layer including a proximal branch end adjacent to the at least one common area, a distal branch end spaced from the proximal branch end, a first branch side spaced from a second branch end, and at least one gap located between the proximal branch end and the distal branch end. Each of the at least one first branch and the at least one second branch also includes at least one first hydrophobic layer disposed adjacent to the first side of the at least one hydrophilic porous layer to partially define the at least one gap, at least one second hydrophobic layer disposed adjacent to the second side of the at least one hydrophilic porous layer to partially define the at least one gap, a first electrode electrically coupled to the at least one first hydrophobic layer and separated from the at least one hydrophilic porous layer by the at least one first hydrophobic layer, and a second electrode electrically coupled to the at least one second hydrophobic layer and separated from the at least one hydrophilic porous layer by the at least one second hydrophobic layer. The flow assay further includes a power source electrically coupled to the first and second electrodes; the power source configured to generate a first voltage between the first electrode and the second electrode of the at least one first branch and a second voltage between the first electrode and the second electrode of the at least one second branch, wherein the second voltage is different than the first voltage. Also, the flow assay includes a control system including control electrical circuitry communicably coupled to the power source. The control electrical circuitry is configured to transmit a first activation signal to the power source that is configured to cause the power source to generate the first voltage and a second activation signal to the power source that is configured to cause the power source to generate the second voltage. The flow assay is configured to at least one of the at least one gap of the at least one first branch exhibits distance between adjacent portions or segments of the at least one hydrophilic porous layer of the at least one first branch and the at least one gap of the at least one second branch is at least partially defined by a second distance between adjacent portions or segments of the at least one hydrophilic porous layer of the at least one second branch, wherein the second distance is less than the first distance; the at least one first hydrophobic layer and the at least one second hydrophobic layer of the at least one first branch collectively exhibit a third hydrophobicity and the at least one first hydrophobic layer and the at least one second hydrophobic layer of the at least one second branch collectively exhibit a fourth hydrophobicity that is different than the third hydrophobicity; the at least one gap of the at least one first branch is at least partially occupied by at least one first hydrophobic porous material exhibiting a first hydrophobicity and the at least one gap of the at least one second branch is at least partially occupied by at least one second hydrophobic porous material exhibiting a second hydrophobicity that is different than the first hydrophobicity; or the at least one gap of the at least one first branch is at least partially occupied by at least one hydrophobic porous material and the at least one gap of the at least one second branch is at least partially occupied by air.

Features from any of the disclosed embodiments can be used in combination with one another, without limitation. In addition, other features and advantages of the present disclosure will become apparent to those of ordinary skill in the art through consideration of the following detailed description and the accompanying drawings.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1A:
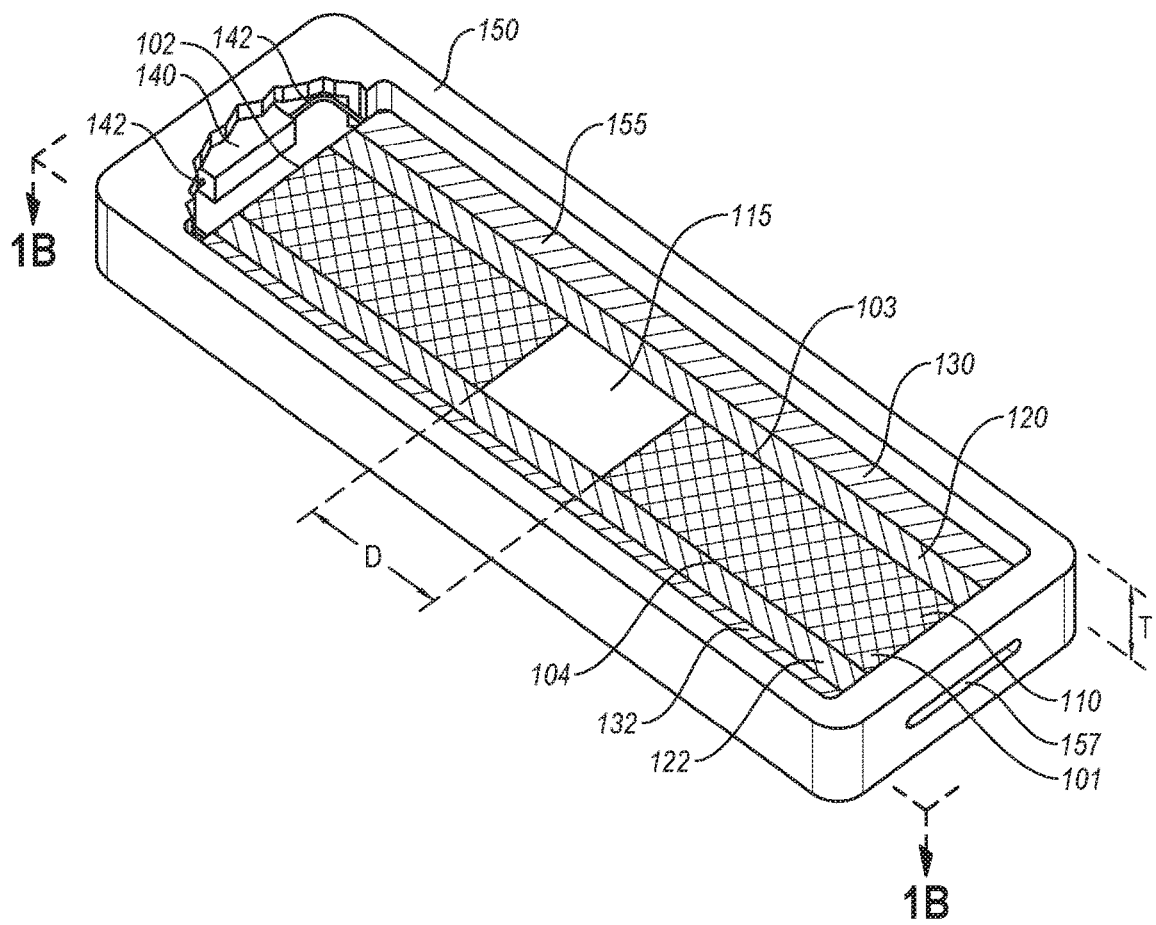
FIG. 1A is an isometric partial cutaway view of a flow assay according to an embodiment.

Embodiments disclosed herein are directed to flow assays (e.g., an LFA) including an electrically-actuated valve configured to control fluid flow. Methods of operating such microfluidic assays are also disclosed.

An LFA can be used to provide point of care testing for a variety of purposes, such as drug tests, pregnancy tests, flu tests, fertility tests, human immunodeficiency virus ("HIV") tests, hepatitis tests, by way of non-limiting example. LFAs function by moving a sample including analyte therein through a length of a capillary bed via capillary action. During capillary transport, the analyte in the sample is exposed to a conjugate material configured to react with the analyte to aid in detection thereof. The conjugate contains a taggant or color molecule. The taggant or color molecule is configured to react with the analyte, reacted analyte molecule, or analyte-conjugate complex and provide a visual indication thereof when concentrated (e.g., bound to an indication strip) in large numbers.

The disclosed embodiments include hydrophilic porous layer that functions as a capillary bed and has a gap therein bordered by hydrophobic material electrically coupled to electrodes, collectively forming an electrically-operated valve. The gap and hydrophobic layers are configured to stop capillary flow of the sample long enough to allow a desired reaction between the analyte in the sample and the conjugate to occur. The sample can be allowed to flow past the gap responsive to application of voltage to the hydrophobic layers. The application of voltage can be controlled via a control system according to desired operational parameters or other criteria.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented here.

Figure 1B:
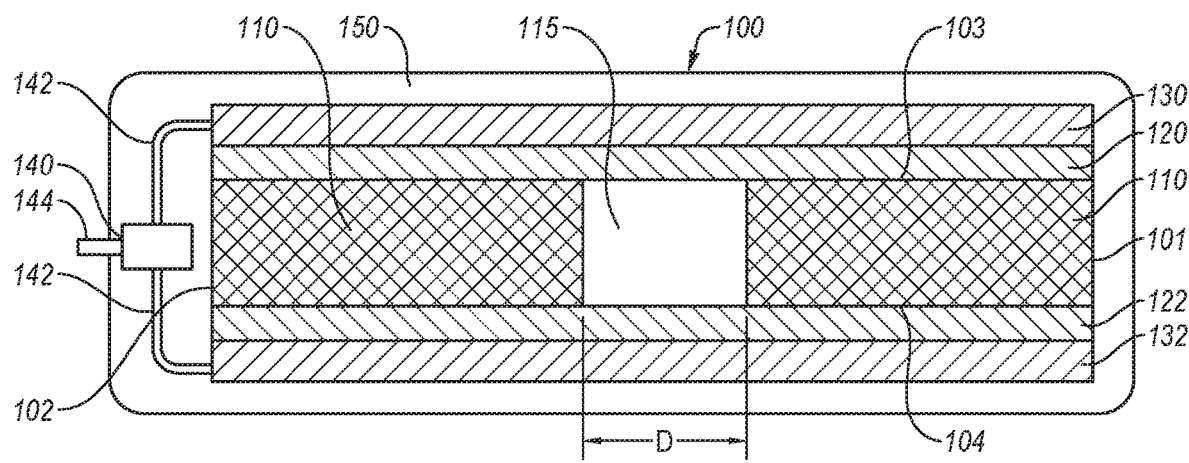
FIG. 1B is a front cross-sectional view of the flow assay of FIG. 1A taken along the line 1B-1B of FIG. 1A.

FIGS. 1A and 1B are illustrations of a flow assay 100 according to an embodiment. FIG. 1A is an isometric cutaway view of the flow assay 100. FIG. 1B is a front cross-sectional view of the flow assay 100 of FIG. 1A taken along the line 1B-1B. The flow assay 100 can be used to determine the presence of one or more specific analytes in a sample. The flow assay 100 can include at least one hydrophilic porous layer 110. The at least one hydrophilic porous layer 110 can include a proximal end 101 spaced from a distal end 102, a first side 103 spaced from a second side 104, and a gap 115 located between the proximal end 101 and the distal end 102 and between the first side 103 and the second side 104. The gap 115 is at least partially defined by the distance "D" between adjacent portions or segments of the at least one hydrophilic porous layer 110.

The flow assay 100 further includes at least one first hydrophobic layer 120 disposed adjacent to the first side 103 of the at least one hydrophilic porous layer 110. The at least one first hydrophobic layer 120 at least partially defines the gap 115. The flow assay 100 also includes at least one second hydrophobic layer 122 disposed adjacent to the second side 104 of the at least one hydrophilic porous layer 110 to at least partially define the gap 115.

The flow assay 100 further includes a first electrode 130 electrically coupled to the at least one first hydrophobic layer 120. The first electrode 130 can be separated from the at least one hydrophilic porous layer 110 by the at least one first hydrophobic layer 120. The flow assay 100 includes a second electrode 132 electrically coupled to the at least one second hydrophobic layer 122. The second electrode 132 can be separated (e.g., spaced) from the hydrophilic porous layer 110 by the at least one second hydrophobic layer 122. The flow assay 100 can include a power source 140 electrically coupled to the first and second electrodes 130 and 132 via electrical connections 142 (e.g., wiring). The power source 140 can be configured to generate, supply, or apply a voltage between the first electrode 130 and the second electrode 132 effective to enable at least the analyte to flow across the gap 115 of the at least one hydrophilic porous layer 110. An actuator 144, electrically coupled with the power source 140, can be configured to initiate and terminate application of voltage. Optionally, the flow assay 100 can include a housing 150 enclosing at least a portion of the hydrophilic porous layer 110, the first and second hydrophobic layers 120 and 122, the first and second electrodes 130 and 132, the power source 140, or the electrical connections 142.

During use, the flow assay 100 can be used to determine or detect the presence of a specific analyte or analytes in a sample. Typical samples can include a liquid containing the analyte (e.g., dispersion, emulsion, etc.) such as diluted or undiluted blood, serum, urine, saliva, mucus, or other samples from a test subject. When exposed to a sample, the at least one hydrophilic porous layer 110 can move the sample through the at least one hydrophilic porous layer 110 via capillary action. The sample can travel through the at least one hydrophilic porous layer 110 until it reaches the gap 115. In an embodiment, the at least one hydrophilic porous layer 110 can further include a conjugate material in at least a portion thereof (e.g., embedded or otherwise dispersed therein). The conjugate material can be formulated to react with a specific analyte (e.g., antigen, molecule, etc.) to yield a specific analyte-conjugate complex or molecule. Typical conjugate materials can include chemical reactants, antibodies, bio-active agents, sugars, salts, taggants, and other materials formulated to ensure satisfactory reaction or bonding between the analyte and one or more conjugate components or indicator components. For example an analyte can be a virus or antigen and a conjugate can contain the antibody to the virus or antigen.

It can be desirable to force the sample and conjugate material to react together for a time longer than the capillary action of the at least one hydrophilic porous layer 110 allows. For example, a given reaction between the conjugate and the analyte in the sample can require 20 minutes to sufficiently develop, whereas the capillary action can carry the analyte past a view area or indicator strip designed to give a visual indication of a product of a reaction in less than 15 minutes, thereby causing a false negative test result.

In the flow assay 100, the sample cannot progress further towards the distal end 102 due to the distance "D" between portions of the at least one hydrophilic porous layer 110 at the gap 115 and the hydrophobic influence of the hydrophobic first and second layers 120 and 122. A voltage can be supplied by the power source 140 to at least one of the first or second electrodes 130 and 132 through the electrical connections 142. The actuator 144 electrically coupled to the power source 140 can control application of the voltage to the first or second electrodes 130 and 132. The applied voltage can act to allow the sample to progress past the gap 115 toward the distal end 102. The voltage can be selectively applied only after a time sufficient to allow for satisfactory extent of, or effective reaction between, the conjugate material and the analyte in the sample. As the conjugate reacts with the sample, a new molecule or complex can be formed. Upon application of the voltage, the complex or new molecule can move toward the distal end 102 through decreased hydrophobicity, induced hydrophilicity, or electro-wetting at one or more of the first or second hydrophobic layers 120, 122 and capillary action within the at least one hydrophilic porous layer 110 proximate to the distal end 102. The application of the voltage can have an electrowetting effect (e.g., lowering the contact angle of a liquid) on the sample, thereby allowing the sample to cross the gap 115.

Without wishing to be bound by theory, it is hypothesized that application of voltage to some hydrophobic materials or electrodes in contact with sample material or conjugate material can result in formation of a layer of less hydrophobic material or at least partially hydrophilic material on the surface of the hydrophobic materials, thereby allowing the sample material to move toward the distal end 102. The layer of less hydrophobic material or at least partially hydrophilic material can reduce the contact angle of the liquid (e.g., sample) sufficient to allow the liquid to cross the gap 115. Thus, the electrically-actuated fluid valves described herein can function at least partially through one or more of electrowetting or formation/coating of at least less hydrophobic material on the surface of the hydrophobic material (or electrodes) in contact with the sample at the gap 115.

In an embodiment, one or more taggants can be disposed in or on the at least one hydrophilic porous layer 110 in the conjugate or proximate to the distal end 102. The one or more taggants can be disposed across the width of the at least one hydrophilic porous layer 110 in one or more lines (e.g., stripe, or strip), dots, blocks, shapes, other designs, or combinations of one or more of the foregoing. The one or more taggants can be formulated to react with a conjugate/analyte complex, conjugate-altered analyte, or analyte molecule to produce a visual indicator of the presence of a conjugate/analyte complex, conjugate altered analyte, or analyte molecule in the sample. Taggants can include latex, gold (e.g., colloidal gold), or other suitable molecules configured to provide a color change or visual indication of a reaction with an analyte when concentrated in large numbers, such as on an indicator portion.

In an embodiment, the flow assay 100 can include an indicator portion or test line. The indicator portion can be a discrete portion of the at least one hydrophilic porous layer 110 that can be proximate to the distal end 102. The indicator portion can include a large concentration of molecules or particles configured to bind to the conjugate/analyte complex, conjugate altered analyte, or analyte molecule including any bound taggant thereon in the sample are located. The indicator portion can include binding molecules, anti-bodies or other particles configured to bind to the conjugate/analyte complex, conjugate altered analyte, or analyte molecule. As larger and larger numbers of the conjugate/analyte complex, conjugate altered analyte, or analyte molecules including bound taggant are bound in the indicator portion, a visual indicator (e.g., color development or change) begins to develop/show therein. The indicator portion can be configured as a strip, stripe, dot, or other shape, as desired.

In an embodiment, the flow assay 100 can include a control portion or control line configured to provide a visual indication that the flow assay operated properly. The control portion can be disposed on a discrete portion of the at least one hydrophilic porous layer 110 at or proximate to the distal end 102 (e.g., closer to the distal end than the indicator portion). The control portion can include a molecule or group of molecules located in a discrete portion of the hydrophilic porous layer 110. The molecules in the control portion can be configured to react with the sample (e.g., any substance in the sample fluid or carried therewith) in order to demonstrate that the flow assay 100 works properly or is complete. The control portion can include a control taggant therein. The control taggant can include latex, gold, or any other particles configured to give a visual indication of their presence upon concentration in large numbers.

In an embodiment, the hydrophilic porous layer 110 can include one or more storage portions. The one or more storage portions can be configured as pads, reservoirs, or portions of the hydrophilic porous layer 110 configured to store a large volume of the sample compared to other portions of the hydrophilic porous layer. For example, the flow assay 100 can include a storage portion near the proximal end 101 configured to hold a large volume of the sample fluid applied to the at least one hydrophilic porous layer 110. The at least one hydrophilic porous layer 110 can then draw the sample therefrom (e.g., the sample travels through the hydrophilic porous layer by capillary action). A similar storage portion can be located near the distal end 102 and can be configured to wick the sample therein, thereby drawing or allowing a sufficient amount of the sample to travel to the distal end 102 to ensure the test provides accurate results.

Any of the flow assays described herein can include one or more taggants, one or more storage portions, an indicator portion, or a control portion.

In an embodiment, the at least one hydrophilic porous layer 110 can include a porous material (e.g., matrix) having a thickness. The at least one hydrophilic porous layer 110 can include, by way of non-limiting example, porous paper, glass fibers (e.g., a glass fiber mat or pad), polymers (e.g., carbonized polymers), or any other material capable of capillary action effective to induce lateral flow therethrough. For example, the at least one hydrophilic porous layer 110 can include nitrocellulose (e.g., a nitrocellulose or cellulose acetate paper or pad).

The at least one hydrophilic porous layer 110 can exhibit a length and width. The length, as measured from the proximal end 101 to the distal end 102, can be at least about 0.25 inches, such as about 0.5 inches to about 5 inches, about 1 inch to about 4 inches, about 1.5 inches to about 3 inches, about 0.5 inches to about 2 inches, about 0.5 inches, about 1 inch, about 1.5 inches, about 2 inches, about 2.5 inches, about 3 inches, or about 4 inches. The width, as measured from the first side 103 to the second side 104, can be at least about 0.125 inches, such as about 0.25 inches to about 1, about 0.375 inches to about 0.75 inches, about 0.5 inches to about 0.625 inches, about 0.25 inches to about 0.75 inches, about 0.25 inches, about 0.5 inches, about 0.625 inches, about 0.75 inches, or about 1 inch. In an embodiment, the at least one hydrophilic porous layer 110 can exhibit a ratio of length to width of about 1:1 or greater, such as about 1:1 to about 20:1, about 2:1 to about 10:1, about 3:1 to about 8:1, about 4:1 to about 6:1, about 2:1, about 3:1, about 4:1, or about 5:1.

In an embodiment, the gap 115 can be defined by the distance D between adjacent portions of the at least one hydrophilic porous layer 110. In an embodiment, the gap 115 can be empty, such as occupied by substantially only air or another gas. The adjacent portions of the at least one hydrophilic porous layer 110 can include a proximal portion at the proximal end 101 and a distal portion at the distal end 102 having the gap 115 therebetween. In an embodiment, the gap 115 can extend the entire width of the at least one hydrophilic porous layer 110. Put another way, the gap 115 can extend from the first side 103 to the second side 104. The distance D can be selected based upon one or more of the desired contact angle of the sample, the voltage necessary for the sample to cross the gap 115, or the limitations of how small a gap 115 can be made. The gap 115 can exhibit a distance D, along the length of the flow assay 100, between the proximal portion and the distal portion of about 0.001 inches or more, such as about 0.001 inches to about 1 inch, about 0.005 inches to about 0.5 inches, about 0.01 inches to about 0.05 inches, about 0.02 inches to about 0.04 inches, about 0.02 inches to about 0.3 inches, about 0.05 inches to about 0.5 inches, about 0.025 inches, about 0.05 inches, about 0.1 inches, about 0.25 inches, or about 0.5 inches.

The first and second hydrophobic layers 120 and 122 can include a material configured to reduce in hydrophobicity, plate with a more hydrophilic material, or erode to expose a more hydrophilic material upon application of voltage thereto. For example, the first and second hydrophobic layers 120 and 122 can include, by way of non-limiting example, polymers, silicones, silanes (e.g., trichloro(perfluorooctyl)silane), heptadecafluorodecyltrimethoxysilane, octadecyldimethylchlorosilane, dimethyldichlorosilane, Teflon, or Teflon AF. The first and second hydrophobic layers 120 and 122 can each be made of the same material or each made of a different material.

Each of the first and second electrodes 130 and 132 can include any material suitable to act as an anode or a cathode. For example, the first and second electrodes 130 and 132 can include a metal, a metal alloy, or other suitable electrically conducting compound in the form of a thin film, a plate, a wire, or any other suitable electrical conducting structure. By way of non-limiting example, at least one of the first and second electrodes can include an alkali metal, and alkaline earth metal, a transition metal, a metalloid, an alloy of one or more of the foregoing, a carbon containing material (e.g., graphite or sintered polymer), or an oxide of one or more of the foregoing (e.g., nickel, iron, copper, silver, gold, platinum, palladium, zinc, tin, aluminum, indium, lithium, titanium, germanium, or indium tin oxide). In an embodiment, the first electrode 130 can be configured as an anode and the second electrode 132 can be configured as a cathode. In an embodiment, the first electrode 130 can be configured as a cathode in the second electrode 132 can be configured as an anode. In an embodiment, each of the first electrode 130 and the second electrode 132 can include the same material or a different material. In an embodiment, one or more of the first electrode 130 in the second electrode 132 can include an electrically conductive layer through which the at least one hydrophilic porous layer 110 is viewable (e.g., indium tin oxide).

In an embodiment, at least one of the first or second electrodes 130 and 132 can be configured to chemically react with the sample or conjugate component during application of voltage. In an embodiment, at least one of the first or second electrodes 130 and 132 configured to chemically react with the sample during application of voltage is configured to be coated with a product of the chemical reaction, the product of the chemical reaction being at least partially hydrophilic or less hydrophobic than the original electrode material. In an embodiment, at least one of the first or second electrodes 130 and 132 can be configured to undergo a redox reaction with the sample or a component thereof during application of voltage between the first electrode 130 and the second electrode 132.

In an embodiment, at least one of the first or second hydrophobic layers 120 and 122 can be configured to chemically react with the sample during application of voltage. In an embodiment, at least one of the first or second hydrophobic layers 120, 122 configured to chemically react with the sample during application of voltage is configured to be coated with a product of the chemical reaction, the product of the chemical reaction being at least partially hydrophilic or less hydrophobic than at least one of the first or second hydrophobic layers 120, 122. In an embodiment, at least one of the first or second hydrophobic layers 120, 122 can be configured to undergo a redox reaction with the sample or a component thereof during application of voltage between the first electrode 130 and the second electrode 132.

While depicted as extending the entire length of the at least one hydrophilic porous layer 110, one or more of the first hydrophobic layer 120, the second hydrophobic layer 122, the first electrode 130, or the second electrode 132 can extend less than the length of the at least one hydrophilic porous layer 110. One or more of the first hydrophobic layer 120, the second hydrophobic layer 122, the first electrode 130, or the second electrode 132 can extend a minimum of the distance D at the gap 115 effective to allow the sample to cross the gap 115 upon application of voltage. For example, the first hydrophobic layer 120, the second hydrophobic layer 122, the first electrode 130, and the second electrode 132 can extend a nominal distance past each side of the gap 115 (e.g., overlapping the at least one hydrophilic porous layer 110) effective for the applied voltage to induce the sample to cross the gap 115.

The first and second electrodes 130 and 132 can be electrically coupled to the power source 140 via the electrical connections 142 (e.g., wiring). The power source 140 can include one or more of a battery or a fixed power supply (e.g., hard wiring, plug-in adapter, etc.) configured to selectively supply the specific voltage (e.g., 9 volts) to at least one of the first electrode 130 in the second electrode 132. For example, the power source 140 can supply at least about 1 volt, such as about 1 volt to about 75 volts, about 3 volts to about 30 volts, about 6 volts to about 12 volts, about 1 volt to about 9 volts, about 3 volts, about 6 volts, or about 9 volts. The actuator 144 can be electrically coupled to the battery to control application of voltage between the first and second electrodes 130 and 132. The actuator 144 can be operated by a manual control (e.g., a button, switch, dial, lever, etc.) or an automatic control (e.g., sensor controlled, timer controlled, control electrical circuitry controlled, etc.). The power source 140 can supply power to all or some of the flow assay 100 including any components therein.

As shown in FIG. 1A, the housing 150 can substantially enclose the at least one hydrophilic porous layer 110, the first and second hydrophobic layers 120 and 122, the first and second electrodes 130 and 132, the power source 140, and the electrical connections 142. The actuator 144 (shown in FIG. 1B) can be at least partially enclosed within the housing 150. The housing 150 can include one or more openings 155 (e.g., a cutout, view hole, or window), through which the flow assay can be viewed. The one or more openings 155 can be covered with a transparent material (e.g., glass, plastic, or the like) to allow a user to visibly inspect the flow assay 100. The housing 150 can include a sample opening 157 at or near the proximal end 101, through which a sample can be introduced to the at least one hydrophilic porous layer 110. In an embodiment, the at least one hydrophilic porous layer 110 can protrude out of the sample opening 157 to or beyond the outer periphery of the housing 150.

The housing 150 can have a thickness "T" larger than that of, and sufficient to enclose, the at least one hydrophilic porous layer 110, the first and second hydrophobic layers 120 and 122, the first and second electrodes 130 and 132, the power source 140, the electrical connections 142, and the actuator 144. In an embodiment, the housing 150 can be bisected at a point in the thickness T along the length and width thereof sufficient to form two halves of the housing 150, which can open in a clam shell style (not shown). Such a configuration can allow for replacement or selection and use of different flow assays (e.g., flow assays configured to detect different analytes) within the same housing 150. In an embodiment, the housing 150 can be configured to at least partially enclose additional features disclosed herein below. For example, the housing 150 can be larger at the distal end 102 to accommodate control electrical circuitry.

Figure 2A:
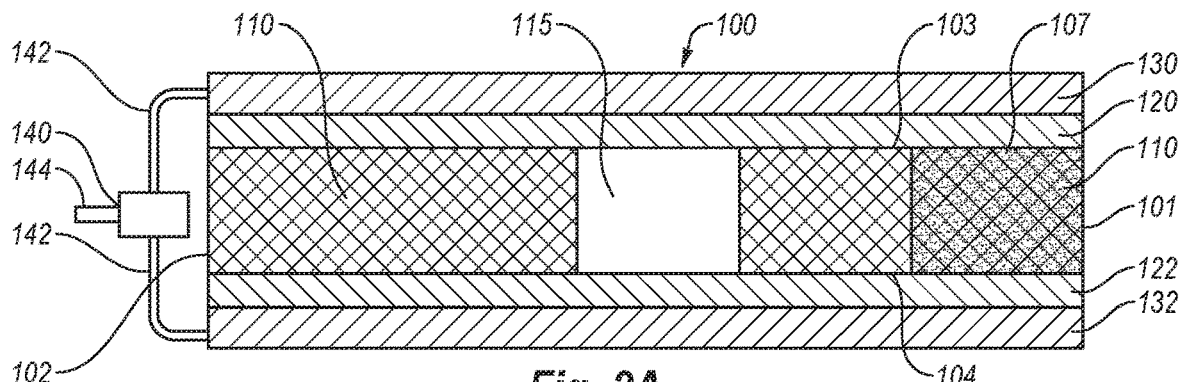
FIGS. 2A-2D are front cross-sectional views of the flow assay of FIG. 1A at different points during use.
Figure 2B:
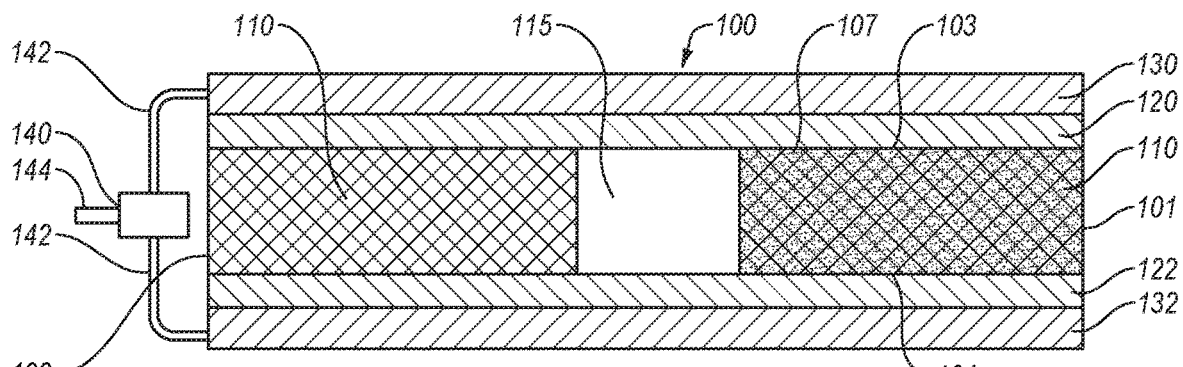
Figure 2C:
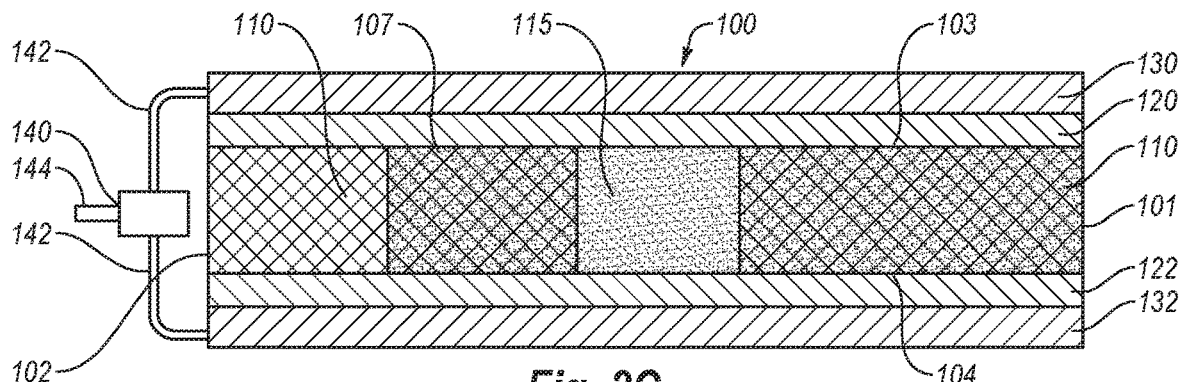

FIGS. 2A-2D are front cross-sectional views of the flow assay 100 of FIGS. 1A and 1B at different points during use. At a point shown in FIG. 2A, a sample 107 can be introduced to the proximal end 101 of the at least one hydrophilic porous layer 110. The sample 107 can be introduced to the proximal end 101 of the at least one hydrophilic porous layer 110 via one or more of immersion, blotting, spotting, or any other suitable sampling technique. The porous material of the at least one hydrophilic porous layer 110 can draw or advance the sample through the length of the at least one hydrophilic porous layer from the proximal end 101 toward the distal end 102 through capillary action (e.g., wicking). At a point shown in FIG. 2B, the at least one hydrophilic porous layer 110 can draw or advance the sample 107 toward the distal end 102 until the sample 107 reaches the gap 115. In an embodiment, a conjugate can be disposed within the at least one hydrophilic porous layer 110 near the proximal end 101. The conjugate can be formulated to react with, bond to, or alter the analyte in the sample 107. It can be necessary to allow the reaction of the analyte and the conjugate to progress for a longer period of time than the capillary action of the at least one hydrophilic porous layer 110 can allow. At a point shown in FIG. 2B, the sample can dwell (e.g., not progress past) at the gap 115 without an external force or stimulus for a sufficient amount of time to allow the reaction to take place. As shown in FIG. 2C, a sufficient voltage can be applied between the first and second electrodes 130 and 132, thereby allowing the sample 107, including any reacted analyte or analyte conjugate complex, to progress towards the distal end 102 past the gap 115. Thus, the gap 115, the first and second hydrophobic layers 120 and 122, the first and second electrodes 130 and 132, and the power source 140 can function as a valve mechanism to selectively prevent or allow the sample 107 to move towards the distal end 102 past the gap 115.

Figure 2D:
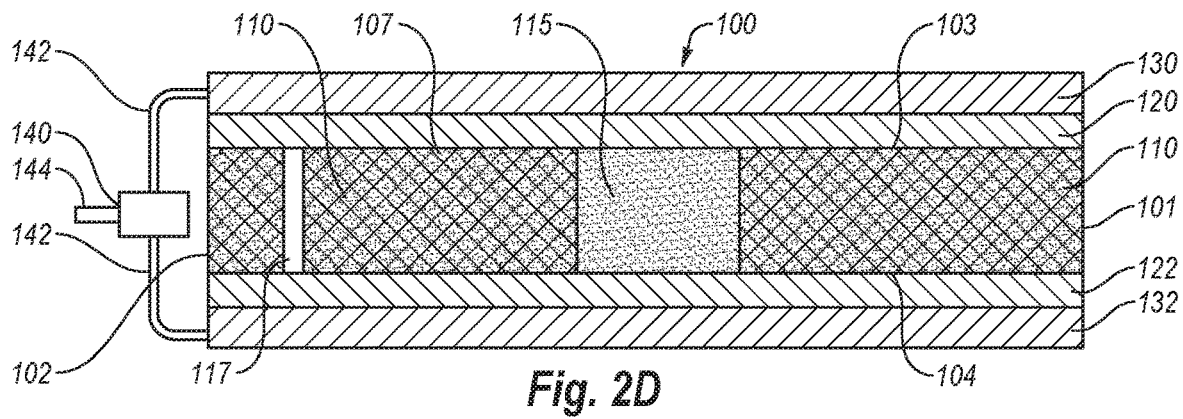

At a point shown in FIG. 2D, the sample can progress within the at least one hydrophilic porous layer 110 to the distal end 102 of the distal portion through capillary action, thereby coming into contact with or passing a indicator portion 117 disposed within the at least one hydrophilic porous layer 110 at or proximate to the distal end 102. The indicator portion 117 can include a plurality of molecules configured react with the product of the reaction between the analyte in the sample and the conjugate (including any taggant therein) or the analyte to give a visual indication of the presence of the analyte in the sample 107. In an embodiment, the taggant can be configured to change the color of the sample liquid or produce a distinctive visual delineation (e.g., stripe, dot, shape, etc.) on the indicator portion 117 of the hydrophilic porous layer 110 when concentrated on the binding molecules therein. The binding molecules can be an antibody or molecule similar or identical to that of the conjugate, such that the analyte bonds to the binding molecules in the indicator portion similarly as to the conjugate, thereby concentrating the analyte and any conjugate (including taggant(s)) thereon in the indicator portion 117.

Figure 3:
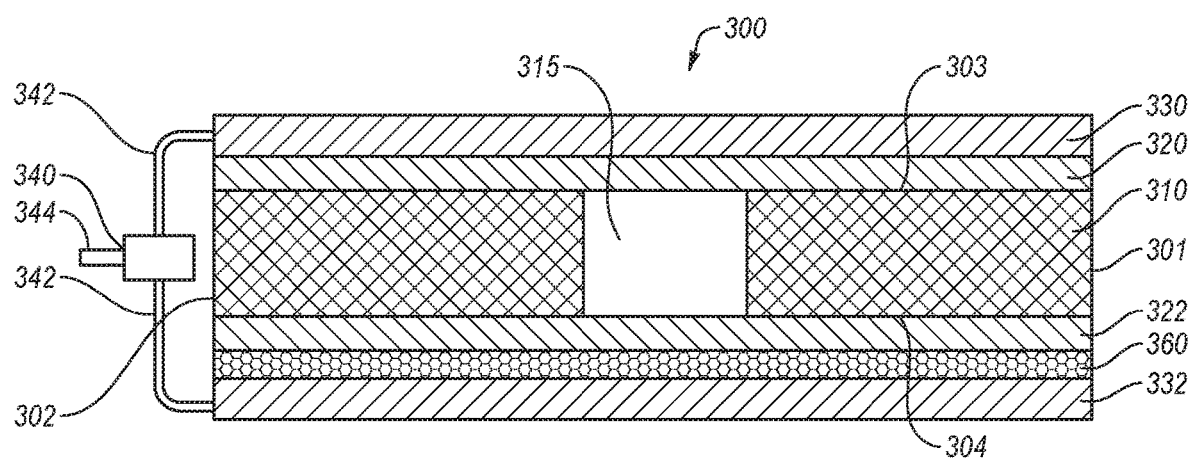
FIG. 3 is a front cross-sectional view of a flow assay according to an embodiment.

FIG. 3 is an illustration of a flow assay according to an embodiment. The flow assay 300 can include at least one hydrophilic porous layer 310 having a proximal end 301, a distal end 302, a first side 303, and second side 304 and gap 315 therebetween substantially similar or identical to the at least one hydrophilic porous layer 110 having a proximal end 101, distal and 102, first side 103, second side 104 and gap 115 therebetween. The flow assay 300 can further include a first hydrophobic layer 320 and a second hydrophobic layer 322 substantially similar or identical to the first hydrophobic layer 120 in the second hydrophobic layer 122. The flow assay 300 can include a first electrode 330 and a second electrode 332 substantially similar or identical to the first and second electrodes 130 and 132, respectively. The flow assay 300 can include a power source 340 electrically coupled to the first and second electrodes 330 and 332 via electrical connections 342, which can be substantially similar or identical to the power source 140 and electrical connections in 142. The power source 340 can be controlled by an actuator 344 substantially similar or identical to the actuator 144.

In the illustrated embodiment, the flow assay 300 can include an insulating layer 360 disposed between the at least one second hydrophobic layer 322 the second electrode 332 as shown in FIG. 3, or between the at least one first hydrophobic layer 320 and the first electrode 330 (not shown). In such embodiments, the insulating layer 360 can act to limit the amount of voltage applied to the sample in the flow assay, thereby controlling the temperature of the sample during use. The insulating layer 360 can include rubber, polymers (e.g., plastics such as polyethylene terephthalate or (e.g., biaxially-oriented polyethylene terephthalate or Mylar, polytetrafluoroethylene or Teflon®) acetate, acrylic, etc.), ceramic materials, glass, or other electrically insulating materials. The at least one insulating layer 360 can have a width sufficient to prevent voltage from passing from between the second hydrophobic layer 322 and the second electrode 332. For example, the at least one insulating layer 360 can exhibit a thickness of about 0.005 inches or more, such as about 0.005 inches to about 0.125 inches, about 0.01 inches to about 0.0625 inches, about 0.025 inches to about 0.05 inches, about 0.01 inches, about 0.025 inches, or about 0.05 inches. Although shown as extending the entire length of the flow assay 300, the insulating layer 360 can extend less than the entire distance of the flow assay 300. For example, the insulating layer 360 can extend only as far as the at least one second hydrophobic layer 322 or the second electrode 332. In an embodiment, an insulating layer 360 can be disposed between the at least one first hydrophobic layer 320 and the first electrode 330 substantially as described above.

Figure 4:
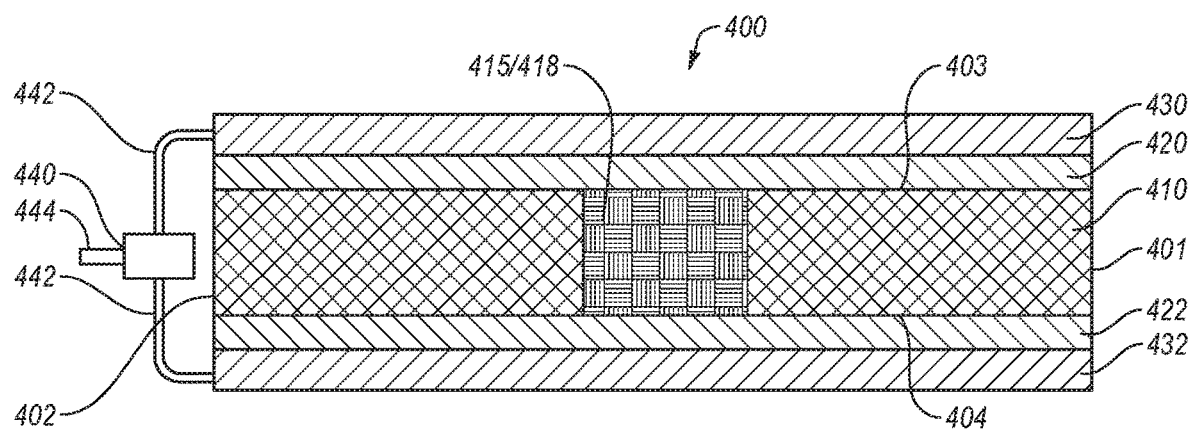
FIG. 4 is a front cross-sectional view of a flow assay according to an embodiment.

FIG. 4 is an illustration of a flow assay according to an embodiment. The flow assay 400 can be substantially similar to the flow assay 100 described herein. The flow assay 400 can include at least one hydrophilic porous layer 410 having a proximal end 401, a distal end 402, a first side 403, and second side 404 and gap 415 therebetween substantially similar or identical to the at least one hydrophilic porous layer 110 having a proximal end 101, distal end 102, first side 103, second side 104 and gap 115 therebetween. The flow assay 400 can include the first hydrophobic layer 420 and a second hydrophobic layer 422 substantially similar or identical to the first hydrophobic layer 120 in the second hydrophobic layer 122. The flow assay 400 can include a first electrode 430 and a second electrode 432 substantially similar or identical to the first and second electrodes 130 and 132, respectively. The flow assay 400 can include a power source 440 electrically connected to the first and second electrodes 430 and 432 via electrical connections 442, which can be substantially similar or identical to the power source 140 and electrical connections in 142. The power source can be controlled by an actuator 444 substantially similar or identical to the actuator 144.

In the illustrated embodiment, a hydrophobic porous material 418 is disposed within the gap 415. The hydrophobic porous material 418 can include any of those materials described above for the at least one first and second hydrophobic layers 120 and 122. In an embodiment, the hydrophobic porous material 418 can include a plurality of fibers (e.g., a matrix, paper, or pad) of any of the hydrophobic materials (e.g., materials used in hydrophobic layers) described herein. In an embodiment, the hydrophobic porous material 418 can be different than the material used in the at least one first and second hydrophobic layers 420 and 422. In an embodiment, the hydrophobic porous material 418 can be the same material used in the at least one first and second hydrophobic layers 420 and 422. The hydrophobic porous material 418 can function to prevent the sample from progressing past the proximal portion of the at least one hydrophilic porous layer 410 until a voltage is applied to one or more of the first and second electrodes 430 and 432. The hydrophobic porous material 418 in within the gap 415 can be configured to reduce in hydrophobicity, become at least partially hydrophilic, or otherwise aid or allow the sample to progress to the distal end 402 of the at least one hydrophilic porous layer 410 upon application of voltage from the power source 440.

The hydrophobic porous material 418 can extend the entire length of the gap 415 from the proximal portion to the distal portion of the at least one hydrophilic porous layer 410. In an embodiment, the hydrophobic porous material 418 can extend less than the entire length of the gap 415, such as about ½ of the length of the gap 415, about one quarter of the length of the gap 415, or about ⅛ of the length of the gap 415. In such embodiments, the hydrophobic porous material 418 can be disposed adjacent to the proximal portion of the at least one hydrophilic porous layer 410, adjacent to the distal portion of the at least one hydrophilic porous layer for 410, centered therebetween, or at a point nearer to one or the proximal portion of the distal portion.

Figure 5:
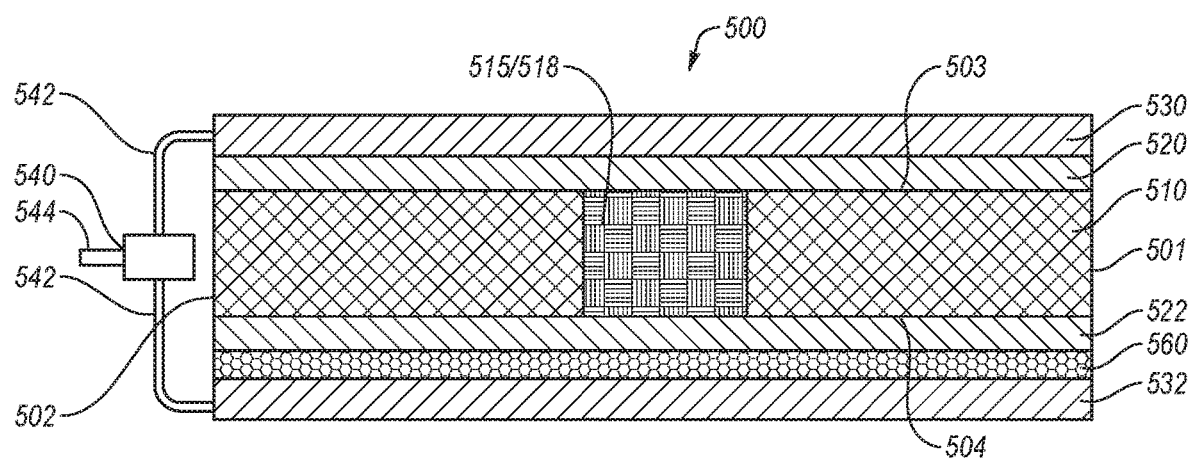
FIG. 5 is a front cross-sectional view of a flow assay according to an embodiment.

FIG. 5 is an illustration of a flow assay according to an embodiment. The flow assay 500 can be substantially similar to the flow assay 100 described herein. The flow assay 500 can include at least one hydrophilic porous layer 510 having a proximal end 501, a distal end 502, a first side 503, and second side 504 and gap 515 therebetween substantially similar or identical to the at least one hydrophilic porous layer 110 having a proximal end 101, distal and 102, first side 103, second side 104 and gap 115 therebetween. The flow assay 500 can include a first hydrophobic layer 520 and a second hydrophobic layer 522 substantially similar or identical to the first hydrophobic layer 120 and the second hydrophobic layer 122. The flow assay 500 can include a first electrode 530 and a second electrode 532 substantially similar or identical to the first and second electrodes 130 and 132, respectively. The flow assay 500 can include a power source 540 electrically connected to the first and second electrodes 530 and 532 via electrical connections 542 which can be substantially similar or identical to the power source 140 an electrical connections in 142. The power source can be controlled by an actuator 544 substantially similar or identical to the actuator 144.

The flow assay 500 can include an insulating layer 560 and a hydrophobic porous material 518 disposed in the gap 515. The insulating layer 560 can be substantially similar or identical to the insulating layer 360 described above, including but not limited any materials, dimensions, positions, or characteristics thereof. The hydrophobic porous material 518 can be substantially similar or identical to that described above with respect to the flow assay 400 in FIG. 4, including but not limited to any materials, dimensions, positions, or characteristics thereof.

Figure 6A:
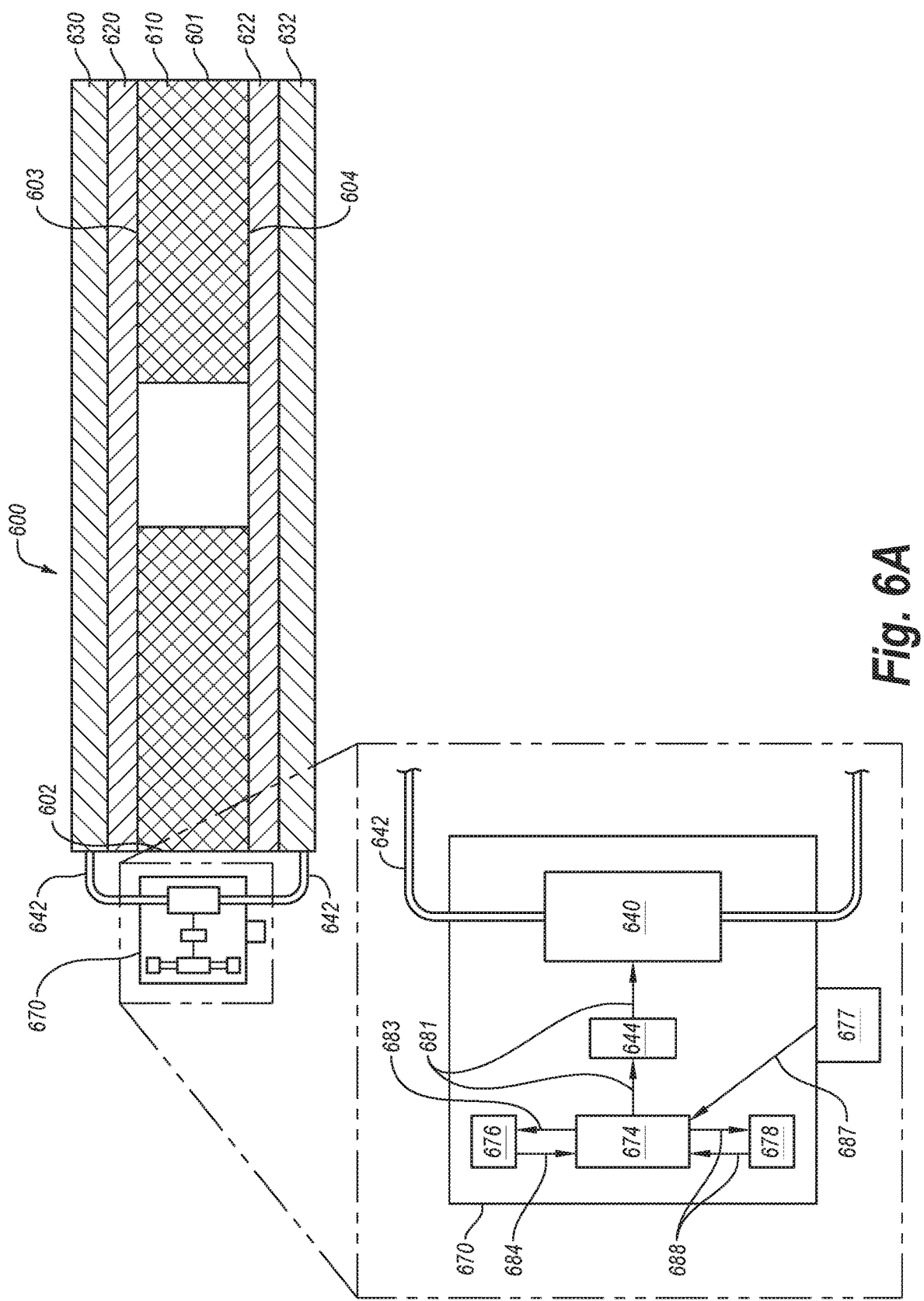
FIG. 6A is a front cross-sectional view of a flow assay according to an embodiment.

FIG. 6A is an illustration of a flow assay according to an embodiment. The flow assay 600 can be substantially similar to the flow assay 100 described herein. The flow assay 600 can include at least one hydrophilic porous layer 610 having a proximal end 601, a distal end 602, a first side 603, and second side 604, and gap 615 therebetween substantially similar or identical to the at least one hydrophilic porous layer 110 having a proximal end 101, distal end 102, first side 103, second side 104, and gap 115 therebetween. The flow assay 600 can include a first hydrophobic layer 620 and a second hydrophobic layer 622 substantially similar or identical to the first hydrophobic layer 120 and the second hydrophobic layer 122. The flow assay 600 can include a first electrode 630 and a second electrode 632 substantially similar or identical to the first and second electrodes 130 and 132, respectively. The flow assay 600 can include a power source 640 electrically coupled to the first and second electrodes 630 and 632 via electrical connections 642 that can be substantially similar or identical to the power source 140 an electrical connections in 142. The power source 640 can be controlled by an actuator 644 substantially similar or identical to the actuator 144.

The flow assay 600 can include a control system 670 including control electrical circuitry 674 (e.g., one or more logic circuits). The control electrical circuitry 674 can be operably coupled to and configured to selectively direct one or more actuators 644 via one or more activation or actuation signals 681 to cause the power source 640 to supply or terminate voltage to the first or second electrodes 630 and 632. The control electrical circuitry 674 can selectively control the amount of voltage applied or the duration of application of voltage based on or responsive to selected operational parameters. The control electrical circuitry 674 can be operably connected to the power source 640 (e.g., via the actuator or directly).

The control system 670 can include a timer 676 operably coupled to and controlled by the control electrical circuitry 674. The timer 676 can be configured to begin timing responsive to a start signal 683 and provide a timer signal 684 to the control electrical circuitry 674 after a specific duration has passed after the start signal 683. The timer signal 684 can trigger the control electrical circuitry 674 to provide (e.g., relay) the activation signal 681 to the actuator 644, thereby directing the power source 640 to provide voltage to one or more of the first or second electrodes 630, 632. The duration required for the timer signal 684 can be at least partially based upon on or more of the desired reaction time of the suspected analyte in a sample and the conjugate used in the at least one hydrophilic porous layer 610, one or more dimensions of the at least one hydrophilic porous layer 610, the material make-up of the at least one hydrophilic porous layer 610, or the sample type. In an embodiment, the start signal 683 can be triggered by user input at a user interface 677, a button, a switch, a computer command, or by control electrical circuitry responsive to a detection or feedback signal from a sensor. User interface 677 can include, by way of non-limiting example, a keypad, monitor, touch screen, voice command recognition, or combinations thereof that is operably coupled to the control electrical circuitry and which can generate a user input signal 687 to the control electrical circuitry.

As will be discussed in more detail below, instructions that the control electrical circuitry 674 of the control system 670 employs for directing and controlling the operation of the flow assay 600 including one or more of the timer 676, the one or more actuators 644, the power source 640, or one or more sensors can be pre-programmed in the control electrical circuitry 674, or programmed at the user interface 677 by the user or other person such as a medical professional like a doctor, a nurse, lab technician, etc. For example, the programming of the control electrical circuitry 674 can be effected via at least one of software, hardware, firmware, programmable logical devices, or other technique for controlling the operation of the flow assay 600. The instructions can be stored on a memory 678 operably coupled to and accessible by the control electrical circuitry 674. The user interface 677 can be used to input data into or access the memory 678. The power source 640 can supply power to all or some of the flow assay 600 including any components therein.

Figure 6B:
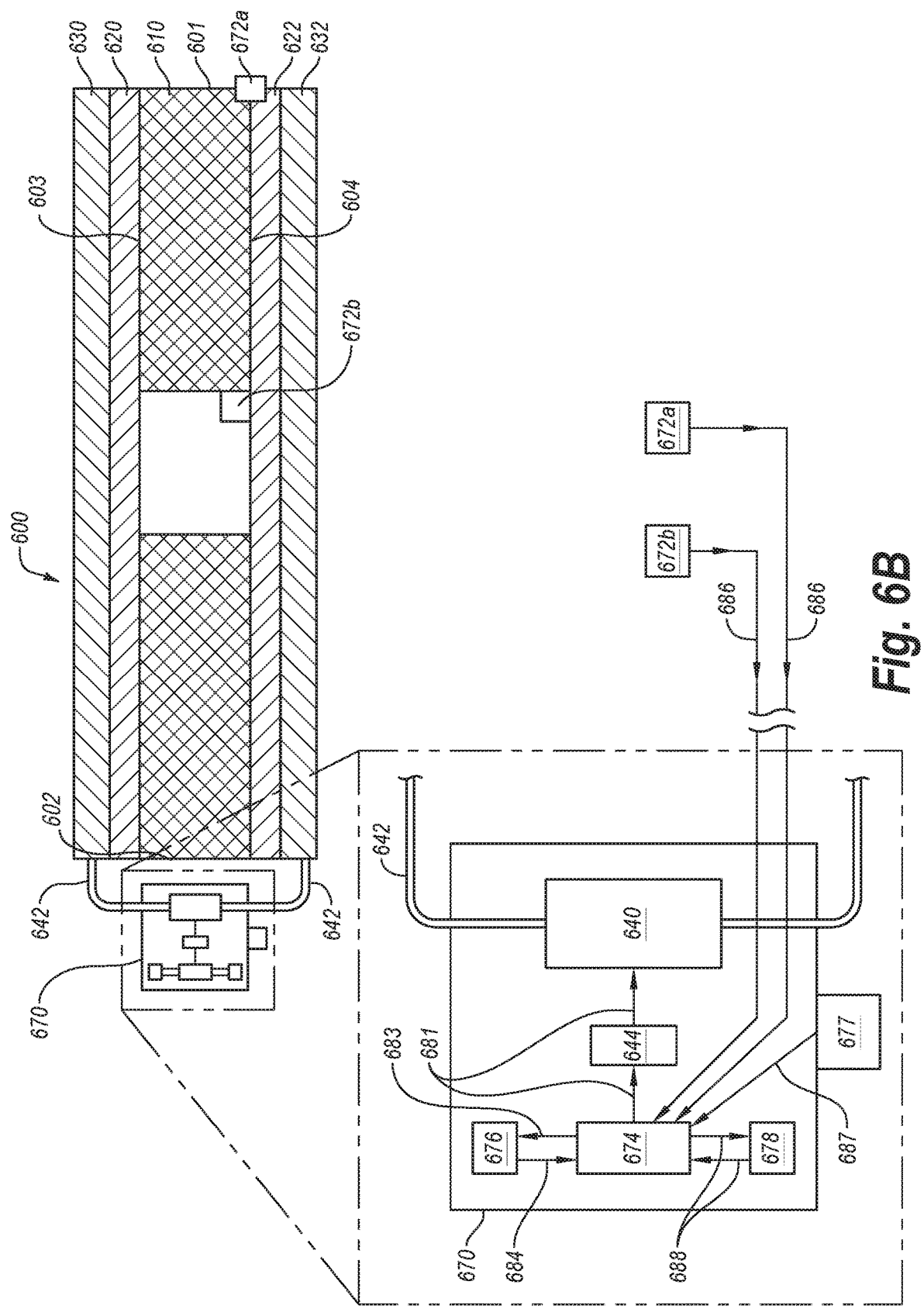
FIG. 6B is a front cross-sectional view of a flow assay according to an embodiment.

The flow assay 600 depicted in FIG. 6B can be substantially similar or identical to the flow assay depicted in FIG. 6A, and can further include one or more sensors 672a and 672b operably connected (e.g., by wiring or by wireless connection) to the control electrical circuitry 674. The one or more sensors 672a and 672b can be configured to provide detection or feedback signals 686 to the control electrical circuitry 674. The one or more sensors 672a and 672b can be configured to detect, by way of non-limiting example, the presence of a sample (e.g., a presence of the sample at or near a gap), the pH in the sample, the resistance in the sample, or any other suitable criteria. For example, one or more of the sensors 672a or 672b can include one of a pH meter, a resistance meter, or any other suitable sensor. In another example, the one or more sensors 672a or 672b can include a fluid sensor, such as a capacitance sensor. The fluid sensor can be disposed in or near a gap. The control system 670 including control electrical circuitry 674 can be configured to selectively direct one or more actuators 644 via one or more activation or actuation signals 681 to cause the power source 640 to supply voltage to the first or second electrodes 630 and 632 responsive to feedback from one or more sensors 672a or 672b. The timer signal 684, user input signal 687 (e.g., user indication to immediately apply voltage), or sensor feedback signal(s) 686 can be collectively or individually referred to as activation signal(s) 681. The one or more activation signals 681 can be delivered to the control electrical circuitry 674 which can relay the activation signal 681 to the actuator 644. The feedback signal(s) 686 from the sensors 672a and 672b can include information regarding one or more of detection of the presence of a sample, detection of a specific pH, detection of a specific resistance in the sample, no detection of any selected indicia, or any other suitable criteria. In an embodiment, housing (not shown) similar or identical to housing 150, can at least partially enclose one or more portions of the control system 670.

For example, as shown in FIG. 6B, the sensor 672a can be positioned at or proximate to the proximal end 601 of the flow assay 600. The sensor 672a can be a resistance sensor, whereby, upon exposure to a liquid in the sample, either directly or as transmitted through the at least one hydrophilic porous layer, the sensor 672a can detect a change in resistance due to the presence of the sample and send feedback to the control electrical circuitry 674. In an embodiment, upon receiving feedback from the sensor 672a, the control electrical circuitry 674 can selectively generate a start signal 683 to the timer 676 which can in turn generate a timer signal 684 to the control electrical circuitry 674 upon expiration of a selected time period. The control electrical circuitry 674 can then send the activation signal 681 to the actuator 644 to apply a selected voltage, thereby allowing the sample including any analyte therein or any analyte-conjugate complex to cross the gap 615. In an embodiment, the amount or duration of voltage can be adjusted by the control electrical circuitry responsive to feedback from the one or more sensors 672a or 672b. For example, if a pH meter is used for sensor 672a or 672b, the control electrical circuitry can send an activation signal 681 to the actuator to apply higher or lower voltage or for a shorter or longer duration based on the level of the detected pH as communicated in the feedback signal 686.

In an embodiment, the sensor 672b can be positioned at, within, or proximate to the gap 615. The sensor 672b can be a pH sensor configured to sense a pH of the sample, or a resistance sensor configured to determine a change in resistance upon contacting the sample. The sensor 672b positioned at, within, or proximate to the gap 615 can send feedback to the control electrical circuitry 674 indicating that the sample has reached the gap 615 or is at a certain pH which can then trigger the start signal 683 to the timer 676. The timer 676 can send the timer signal 684 to the control electrical circuitry 674, which can send the activation signal 681 to the actuator 644 to apply voltage to the first and second electrodes 630 and 632, thereby allowing the sample to cross the gap 615.

In an embodiment, the sensor 672a and a sensor 672b can be configured as different sensor types or the same sensor type. For example, the sensor 672a can be positioned proximate to the proximal end 601 and the sensor 672b can be positioned proximate to the gap 615, with both sensors contacting the at least one hydrophilic porous layer 610. Both of the sensors 672a and 672b can be pH sensors, and as the sample is moved through the at least one hydrophilic layer 610 towards the gap 615, the sensor 672a can detect a first pH and sensor 672b can detect a second pH. The detected pHs can be sent to the control electrical circuitry 674 as feedback and the extent of a reaction between the sample and the conjugate material within the at least one hydrophilic layer 610 can be determined responsive to the feedback. In an embodiment, two or more sensors can be used in a flow assay. In an embodiment, one or more of the sensors 672a and 672b can be positioned anywhere along the length of the flow assay 600. In an embodiment, the sensors 672a and 672b can be modular, or able to be replaced, with the same sensor or replaced with another type of sensor. In an embodiment, the sensor 672a can be a resistance sensor configured to send feedback upon detection of a sample to start a timer and the sensor 672b can be a pH sensor configured to detect the selected pH of the sample, either one of which can provide the feedback to trigger application of voltage.

The control system 670 can further include a memory 678 operably coupled with the control electrical circuitry 674. The memory 678 can be programmed with and store instructions for controlling the operation of the flow assay 600.

The memory 678 can be programmed with and store operational parameters such as but not limited to timer durations, voltage application, voltage termination, voltage amount, and voltage duration. Operational parameters can be selected based at least partially on one or more of other operational parameters, or further criteria such as but not limited to the sample type, the hydrophilic porous layer material, conjugate type, suspected analyte type, electrode material, hydrophobic layer material, dimensions of one or more of hydrophilic porous layers, electrodes, hydrophobic layers.

The above criteria for determining the operational parameters can be stored in the memory 678. The control electrical circuitry 674 or memory 678 can be programmed via the user interface 677. The memory 678 can be programmed with instructions for operation, operational parameters, or instructions for determining operational parameters based on any of the above listed criteria via a user interface 677. The memory 678 can be accessed 688 (e.g., access, input, store, or retrieve information in or from) by the control electrical circuitry 674 to compare, determine, or otherwise use the instructions for operation, operational parameters, instructions for determining operational parameters or user input stored therein. Using the information stored in the memory 678, the control electrical circuitry 674 can determine and control the timer 676 or send/relay an activation signal 681 to the actuator 644. Such a determinations, controls, and or signals can be based upon and responsive to one or more of instructions for operation, operational parameters, instructions for determining operational parameters, receipt of timer signal, or feedback from the sensors.

For example, the user can input one or more of the dimensions and material of the at least one hydrophilic porous layer 610, the gap distance D, the material in the gap 615, the conjugate material, or the suspected analyte into the memory 678. The control electrical circuitry 674 can select, adjust, or determine the timer duration, voltage amount, or voltage duration based on the information in the memory 678 or input by the user at the user interface 677. In an embodiment, the control electrical circuitry can access 688 (e.g., access, input, store, or retrieve information in or from) the memory 678 to determine or adjust one or more of instructions for operation, instructions for determining operational parameters, timer duration, voltage amount, or voltage duration. Such determination and adjustment can be responsive to one or more of sensor feedback signals 686, timer signals 684, or activation signals 681, criteria in the memory 678, or user input signals 687.

In an embodiment, a housing (not shown) similar or identical to housing 150, can at least partially enclose one or more portions of the control system 670 and one or more of the first and second sensors 672a and 672b. Any of the disclosed embodiments herein can include one or more of the control system 670, at least one sensor 672a and 672b, the control electrical circuitry 674, the timer 676, the user interface 677, or the memory 678 as described above.

Figure 7:
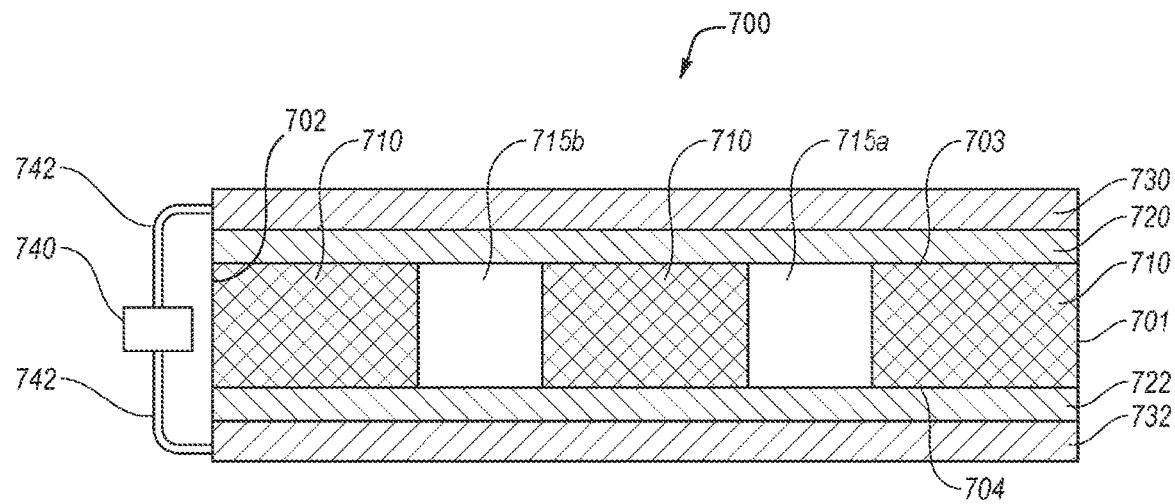
FIG. 7 is front cross-sectional view of a flow assay according to an embodiment.

FIG. 7 is an illustration of a flow assay according to an embodiment. The flow assay 700 can include at least one hydrophilic porous layer 710 having a proximal end 701, a distal end 702, a first side 703, and second side 704 substantially similar or identical to the at least one hydrophilic porous layer 110 having the proximal end 101, distal and 102, first side 103, and second side 104. The flow assay 700 can include a first hydrophobic layer 720 and a second hydrophobic layer 722 substantially similar or identical to the first hydrophobic layer 120 and the second hydrophobic layer 122. The flow assay 700 can include a first electrode 730 and a second electrode 732 substantially similar or identical to the first and second electrodes 130 and 132, respectively. The flow assay 700 can include a power source 740 electrically coupled to the first and second electrodes 730 and 732 via electrical connections 742 which can be substantially similar or identical to the power source 140 an electrical connections in 142. The power source can be controlled by an actuator 744 substantially similar or identical to the actuator 144. The flow assay can include a control system (not shown) or one or more sensors (not shown) as described herein.

The hydrophilic porous layer 710 can include one or more gaps therein, such as a first gap 715a and a second gap 715b spaced therefrom. The first gap 715a can be located proximate to the proximal end 701 and the second gap 715b can be located proximate to the distal end 702. Thus, the hydrophilic porous layer 710 can include a proximal portion at the proximal end 701, a distal portion near the distal end 702, and a medial portion therebetween, with the medial portion being isolated from the proximal and distal portions by the first and second gaps 715a and 715b. The first and second electrodes 730 and 732 can function and be used to allow the sample and any materials therein to progress past the individual first and second gaps 715a and 715b in a similar or identical manner as any electrodes and gaps described herein In an embodiment, a first conjugate can be located in the proximal portion of the at least one hydrophilic porous layer 710 and a second conjugate can be located within the medial portion of the at least one hydrophilic porous layer 710. It can be desirable to allow the sample (including any analyte therein) to react with the first conjugate for a selected time to allow sufficient or complete reaction thereof prior to applying voltage to the first and second electrodes 730 and 732 sufficient to allow the sample, reacted analyte, and or analyte-first conjugate complex to progress to the medial portion of the at least one hydrophilic porous layer 710. At the medial portion, the sample, reacted analyte, and or analyte-first conjugate complex can come into contact and react with the second conjugate for a time sufficient to allow satisfactory or complete reaction therebetween. After such time, voltage can be applied to the first and second electrodes 730 and 732 sufficient to allow the sample including any analyte, reacted analyte, or analyte-first and second conjugate complex to flow past the gap 715b to the distal portion of the at least one hydrophilic porous layer 710. An indicator portion (not shown) can be disposed in the distal portion of the at least one hydrophilic porous layer 710 at or proximate to the distal end 702. The indicator portion can include molecules configured to bind the analyte (including any conjugate and taggant bonded thereto) thereon. The conjugate can contain a taggant configured to provide a visual indication of the analyte, the reacted analyte, the analyte-first and second conjugate complex or combinations of one or more of the foregoing upon concentration in large numbers at the indication portion or strip.

In an embodiment, one or more of the at least one first hydrophobic layer 720, at least one second hydrophobic layers 722, or the first and second electrodes 730 and 732 can be broken (e.g., have a gap therein) between the proximal and distal ends of the medial portion of the at least one hydrophilic porous layer 710. The first and second electrodes 730 and 732 can be electrically coupled to the power source 740 on both sides of the gap therein. In operation, voltage can be selectively applied to the at least one first and second hydrophobic layers 720 and 722 and the first and second electrodes 730 and 732 only near the gap 715a or only near the gap 715b.

Figure 8:
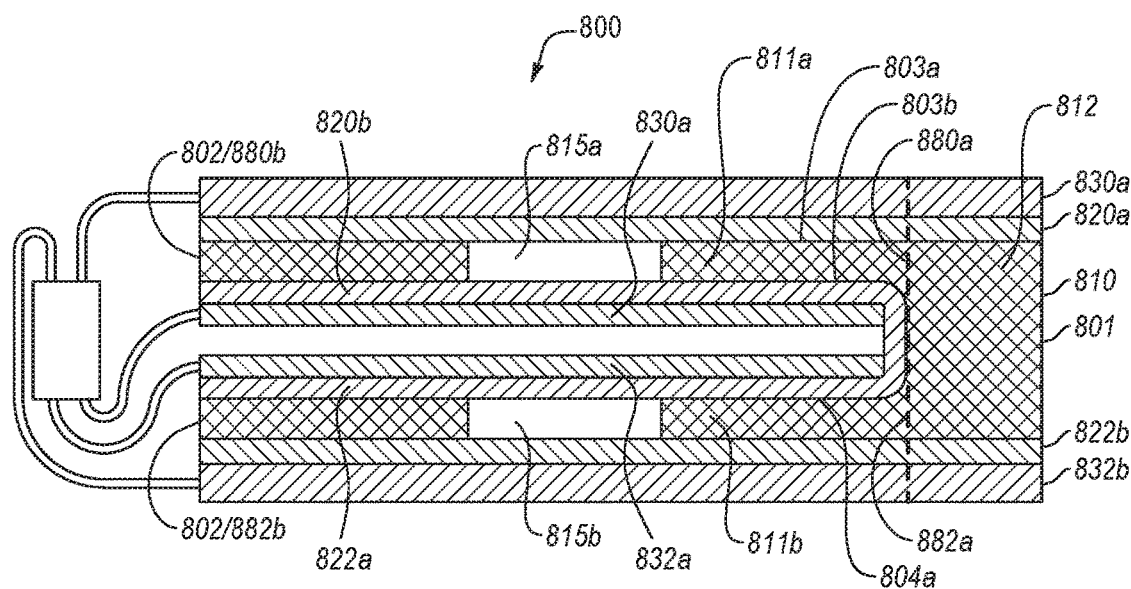
FIG. 8 is a front cross-sectional view of a flow assay according to an embodiment.

FIG. 8 is an illustration of a flow assay 800 according to an embodiment. In an embodiment, the flow assay 800 can split into two or more branches, each configured to individually test for an analyte substantially as described herein. Portions or components of the flow assay 800 can be substantially similar to portions or component of any flow assay described herein.

The flow assay 800 can include at least one hydrophilic porous layer 810 having a proximal end 801, a plurality of distal ends 802, at least one common area 812, and at least one first branch 811a and at least one second branch 811b on the distal end 802 side of the reference line S. The first and second branches 811a and 811b of the at least one hydrophilic porous layer 810 are separated by a space therebetween extending from a point intermediate to the proximal and distal ends 801 and 802 (marked by the reference line S) to the distal end 802. The split or division between the branches 811a and 811b can allow for substantially simultaneous capillary flow of the same sample material into both branches 811a and 811b. In an embodiment, each branch

811a and 811b can be configured to detect the presence of the same analyte or a different analyte. In an embodiment, each branch 811a or 811b can have the same or different conjugate materials therein. In an embodiment, each branch 811a or 811b can have the same conjugate materials therein, present in different concentrations in the branches. In an embodiment, each conjugate in the branch 811a or 811b can have the same or different taggants therein. In an embodiment, each conjugate in the branch 811a or 811b can have the same taggants therein, present in different concentrations in the branches. In an embodiment, each branch 811a or 811b can have the same or different indicator portions therein. In an embodiment, each branch 811a or 811b can have different indicator portions therein wherein the differences are in the pattern of positioning of the indicators, such as smaller or larger dots, lines, dashes, or other patterns. The flow assay 800 can include any conjugate or taggant described herein.

The common area 812 is configured to receive or otherwise have a sample disposed therein. For example, the common area 812 can be disposed in to a sample opening of the flow assay 800 (e.g., the sample opening 157 of FIG. 1A). The common area 812 can be fluidly coupled to the sample opening, the first branch 811a, and the second branch 811b. As such, the common area 812 can form a fluid pathway that enables a sample that is introduced at the sample opening to flow across the common area 812 and into at least one of the first or second branches 811a or 811b.

The first branch 811a and the second branch 811b include at least one hydrophilic porous layer 810. The common area 812 can also include at least one hydrophilic porous layer 810. In an embodiment, as illustrated, the hydrophilic porous layer 810 of at least a portion of the first branch 811a, at least a portion of the second branch 811b, and the common area 812 are formed from the same material and collectively form a single hydrophilic porous layer. In another embodiment, the hydrophilic porous layer 810 of at least two of at least a portion of the first branch 811a, at least a portion of the second branch 811b, or the common area 812 are formed from different material or are not continuous.

The at least one hydrophilic porous layer 810 of the first branch 811a can extend from a first proximal branch end 880a to a first distal branch end 880b. The hydrophilic porous layer 810 of the first branch 811a also includes a first side 803a, a second side 803b, and at least one first gap 815a located between the first proximal branch end 880a and the first distal branch end 880b. The first gap 815a can be configured substantially similar or identical to any gap described herein. For example, the first gap 815a can have any gap distance D, any material therein, or any other property described for a gap herein. The first branch 811a can also include at least one first hydrophobic layer 820a bound to the at least one hydrophilic porous layer along the first side 803a, at least one second hydrophobic layer 820b bound to the at least one hydrophilic porous layer along the second side 803b, a first electrode 830a attached to and extending along the length of the first hydrophobic layer 820a, and a second electrode 830b attached to and extending along length of the second hydrophobic layer 820b. It is noted that the first and second hydrophobic layers 820a and 820b can be the same as or similar to any of the hydrophobic layers disclosed herein. Similarly, the first and second electrodes 830a and 830b can be the same as or similar to any of the electrodes disclosed herein.

Except as otherwise disclosed herein, the second branch 811b can be the same as or substantially similar to the first branch 811a. For example, the at least one hydrophilic porous layer 810 of the second branch 811b can extend from a second proximal branch end 882a to a second distal branch end 882b, a third side 804a spaced from a fourth side 804b, and at least one second gap 815b located between the second proximal branch end 882a and the second distal branch end 882b. The second branch 811b can also include at least one third hydrophobic layer 820a, at least one fourth hydrophobic layer 822b, a third electrode 832a, and a fourth electrode 832b. The third and fourth hydrophobic layers 822a and 822b can be the same as or different than the first or second hydrophobic layers 820a and 822b. The third and fourth electrodes 832a and 832b can be the same as or different than the first and second electrodes 830a and 830b.

In an embodiment, the second gap 815b can be the same as the first gap 815a. In an embodiment, the second gap 815b can be different than the first gap 815b, such as but not limited to dimensions or materials therein.

In an embodiment, as shown, the second and third hydrophobic layers 820b and 822a can be integrally formed such that the second and third hydrophobic layer 820b and 810b form a continuous hydrophobic layer, such as a continuous U-shaped hydrophobic layer. In an embodiment, the second and third hydrophobic layers 820b and 822a are not integrally formed together. Instead, the second and third hydrophobic layers 820b and 822a form two distinct hydrophobic layers that can contact each other or are spaced from each other.

During use, the first electrode 830a and the second electrode 830b of the first branch 811a can be used to apply a voltage from the power source 840 via the electrical connections 842 at the same time or at a different time as the (generally opposite the first electrode 830) the third electrode 832a and the fourth electrode 832b of the second branch 811b. For example, two different conjugates can be used in flow assay 800, a first conjugate in the first branch 811a and a second conjugate in the second branch 811b. The first and second conjugates can be configured to react with the same analyte in a sample by a different means or react with different analytes in the same sample. It can be necessary for the samples to remain at the gaps 815a and 815b for different times. Thus, voltage can be applied to the first electrode 830a and the second electrode 830b of the first branch 811a at a different time than voltage is applied to the third electrode 832a and the fourth electrode 832b of the second branch 811b.

Although shown as substantially the same, the branches 811a and 811b can have one or more of different dimensions (e.g., length, width, or thickness), different materials therein, different conjugates, different taggants, different voltages amounts or durations applied, or different sized gaps.

In an embodiment, the flow assay 800 can include a housing substantially similar to any housing described herein. In an embodiment, the flow assay 800 can include a control system including one or more of control electrical circuitry, a timer, one or more sensors, a user interface, or memory, each being substantially similar or identical to any described herein. For example, the flow assay 800 can include at least one sensor in each of the branches 811a and 811b operably coupled with the control electrical circuitry to selectively control the application of voltage in each of the branches 811a and 811b responsive to the sensors. In an embodiment, the flow assay 800 can include one or more timers, configured to time each branch 811a and 811b separately and provide a timer signal to the control electrical circuitry.

Figure 9:
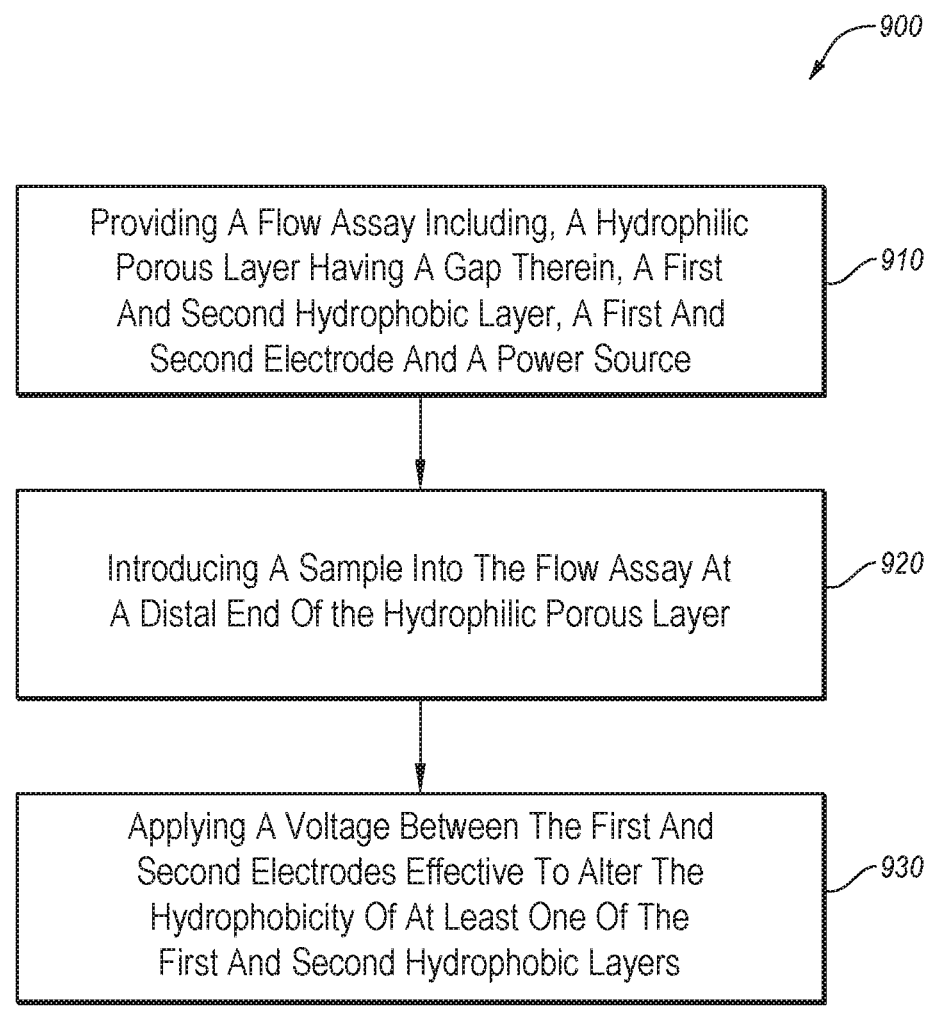
FIG. 9 is a schematic of a method of using a flow assay according to an embodiment.

FIG. 9 is a flow diagram of an embodiment of a method 900 of detecting the presence of an analyte in a sample. The method can include an act 910 of providing a flow assay. The flow assay can be substantially similar to any flow assay described herein. For example, the flow assay can include at least one hydrophilic porous layer having a proximal end through which the sample can be introduced, a distal end spaced from the proximal end, a first side spaced from a second side, and a gap located between the proximal end and the distal end and located between the first side and the second side. The flow assay can include at least one first hydrophobic layer disposed adjacent to the first side of the at least one hydrophilic porous layer to partially define the gap and at least one second hydrophobic layer disposed adjacent to the second side of the at least one hydrophilic porous layer to partially define the gap. The flow assay can further include a first electrode electrically coupled to the at least one first hydrophobic layer and separated from the at least one hydrophilic porous layer by the at least one first hydrophobic layer, and a second electrode electrically coupled to the at least one second hydrophobic layer and separated from the at least one hydrophilic porous layer by the at least one second hydrophobic layer.

The method 900 can include an act 920 of introducing the sample at the distal end of the at least one hydrophilic porous layer of the flow assay. The act 920 can include immersing, spotting, dotting, blotting, dropping, pipetting or any other means of applying a liquid sample to a porous substance.

The method 900 can further include an act of 930 of applying a voltage between the first electrode and the second electrode effective to alter a hydrophobicity of at least one of the at least one first hydrophobic layer or the at least one second hydrophobic layer. The act 930 can include applying or using a voltage effective to allow one or more of the analyte, analyte-conjugate complex, reacted analyte, or the sample in the at least one hydrophilic porous layer to progress past the gap therein so the determination of the presence of the analyte in the sample can be made. In an embodiment, the act 930 can include applying or using a voltage effective to enable a chemical reaction between the sample and at least one of the first electrode, the second electrode, the first hydrophobic layer, or the second hydrophobic layer sufficient to form a reaction product on the surface of the first electrode, the second electrode, the first hydrophobic layer, or the second hydrophobic layer.

In an embodiment, the act 930 can include selectively applying (e.g., initiating, terminating, amount, or duration) of the voltage after a predetermined time period at least partially based on at least one of the type of suspected analyte, sample type, the type of hydrophilic porous material using in the at least one hydrophilic porous layer, one or more dimensions of the at least one hydrophilic porous layer, the type of conjugate used in the hydrophilic porous layer, or any other suitable criteria disclosed herein. In an embodiment, the length of time the voltage is applied can be used to at least partially determine the amount of voltage used.

In an embodiment, the method 900 can include the act of allowing the sample to flow to the gap for a predetermined amount of time prior to applying the voltage. In an embodiment, the method 900 can include the act of allowing the sample to flow across the gap (while the voltage is supplied) for a predetermined amount of time prior to terminating the application of voltage. In an embodiment, the predetermined amount of time can be selected based upon one or more of the time it takes for the suspected analyte to react with the conjugate to a satisfactory degree, the dimensions of the at least one hydrophilic porous layer, the material type of the at least one hydrophilic porous layer, the analyte, the sample, the conjugate, or any other suitable criteria described herein.

In an embodiment, the predetermined amount of time can be 5 seconds or more, such as about 5 seconds to about 1 hour, about 30 seconds to about 45 minutes, about 1 minute to about 30 minutes, about 5 minutes to about 20 minutes, about 10 minutes to about 30 minutes, about 5 minutes, about 10 minutes about, about 15 minutes, about 20 minutes, about 30 minutes, or about 1 hour.

In an embodiment, the material used to form the at least one hydrophilic porous layer can be selected at least partially based upon one or more of suspected analyte or analyte type, sample type, one or more dimensions of the gap, presence and type of material in the gap, required conjugate, amount of voltage needed for the sample to cross the gap, or the dimensions of the at least one hydrophilic porous layer (e.g., length, thickness, or width).

In an embodiment, the user interface can be used to direct the control electrical circuitry of the control system to provide or relay an activation signal to the actuator or directly to the power supply to a selected time period after the user direction is input into the user interface. In an embodiment, the user can input the selected time period (e.g., the selected delay time) such as any time period descried herein. In an embodiment, the user can input the selected voltage amount, such as any voltage amount described herein.

In an embodiment, the method 900 can include programming operational instructions, programming operational parameters, inputting criteria, or programming instructions for determining operational parameters into the memory 678 via the user interface 677. Thus, in an embodiment, applying a voltage between the first and second electrodes takes place at least partly according to a pre-programmed operational instruction, parameter or criteria. In an embodiment, the user interface can be used to input, by way of non-limiting example, the sample type, suspected analyte being detected, one or more dimensions of the at least one hydrophilic porous layer, one or more dimensions of the gap, presence and type of material in the gap, type of hydrophobic material used in the at least one first and second hydrophobic layers, or any other criteria. In an embodiment, the operational parameters can be input or selected based on one or more of the time it takes for the suspected analyte to react with the conjugate to a satisfactory degree, one or more of the dimensions of the at least one hydrophilic porous layer, one or more of the dimensions of the gap, the material type of the at least one hydrophilic porous layer, the analyte or type thereof, the sample or type thereof, the conjugate or type thereof, presence or type of material in the gap, type of hydrophobic material used in the hydrophobic material layers, or any other suitable criteria described herein. In an embodiment, the control electrical circuitry can determine the operational parameters at least partially based on one or more of the other operational parameters or one or more of the criteria listed above. In an embodiment, the control electrical circuitry can direct a signal to one or more of the timer, actuator, or power supply to carry out one of the operational parameters responsive to user input of the operational parameters or the determined operational parameters.

In an embodiment, the method 900 can further include selecting the sample type via the user interface, and wherein applying the voltage includes applying the voltage after a selected or predetermined time at least partially based on the sample or type thereof. In an embodiment, the method 900 can further include visually detecting the presence of the analyte or lack thereof. Visually detecting the presence of the analyte or lack thereof can be accomplished through a window in the housing of the flow assay or through one or more transparent electrodes or electrically conductive layer thereon, through which the at least one hydrophilic porous layer is visible or viewable. In an embodiment, a user can time keep track of the time the sample dwells at the gap before directing the application of voltage.

FIGS. 10-13 illustrate flow assays according to different embodiments. Except as otherwise disclosed herein, the flow assays of FIGS. 10-13 can be substantially the same as or similar to any of the flow assays disclosed herein, such as the flow assay 800 of FIG. 8. The flow assays shown in FIGS. 10-13 include at least one first branch that is configured to detect (e.g., provide an indication, such as a visual indication) a first characteristic of a sample and the second branch that is configured to detect a second characteristic of the sample that can be different than the first characteristic. For example, the first branch can be configured to detect a first concentration of at least one analyte that can be present in the sample while the second branch can be configured to detect a second concentration of the at least one analyte that is different than the first concentration. In such an example, the flow assay can provide an at least semi-quantitative output. In another example, the first branch can be configured to detect at least one first analyte that can be present in the sample and the second branch can be configured to detect at least one second analyte that can be present in the sample. The second analyte is different than the first analyte.

In either example, the period of time that the sample needs to react with at least one conjugate or taggant that is disposed in the flow assay can vary depending on the characteristics sensed by the first branch and the second branch. In particular, the characteristics sensed by the first branch can require the sample to react with the conjugate or taggant for a first period of time while the second branch can require the sample to react with the conjugate or taggant for a second period of time that is different than the first period of time.

The flow assays illustrated in FIGS. 10-13 can be configured to enable a portion of the sample to flow across a gap of the first branch only when a first voltage is applied to electrodes of the first branch. The power source can be configured to only apply the first voltage after a first selected time period. Similarly, the flow assay can be configured to enable a portion of the sample to flow across a gap of the second branch only when a second voltage that is different than the second voltage is applied to the electrodes of the second branch. The power source can be configured to only apply the second voltage after a second selected time period that is different than the first selected time period. As such, the flow assay can be configured to selectively and controllably enable to the flow the sample across the gaps of the first and second branches by selectively and controllably applying the first or second voltage to the electrodes of the first branch or second branch. In an embodiment, the power source can be configured to apply the same voltage simultaneously to all the electrodes of the flow assay. For example, the power source can be configured to apply the first voltage to the electrodes of the first and second branches after the first selected time period and the second voltage to the electrodes of the first and second branches after the second selected time period. In an embodiment, the power source can be configured to selectively apply different voltages to the electrodes of the different branches. For example, the power source can be configured to selectively apply the first voltage to the electrodes of the first branch after the first selected time period and a different voltage (e.g., no voltage or the second voltage) to the electrodes of the second branch. Similarly, the power source can be configured to selectively apply the second voltage to the electrodes of the second branch after the second selected time period and a different voltage (e.g., no voltage or the first voltage) to the electrodes of the first branch.

For example, the flow assays of FIGS. 10-13 can be configured such that one of the first or second voltage is greater than the other of the first or second voltage by at least about 5%, at least about 10%, at least about 15%, at least about 25%, at least about 50%, at least about 75%, at least about 100%, at least about 150%, at least about 200%, at least about 300%, at least about 500%, about 5% to about 50%, about 25% to about 75%, about 50% to about 100%, about 75% to about 150%, about 100% to about 200%, about 150% to about 300%, or about 250% to about 500%. In another example, one of the first or second voltage is greater than the other of the first or second voltage by about 0.1 volts to about 75 volts, about 1 volt to about 50 volts, about 3 volts to about 30 volts, about 6 volts to about 12 volts, about 0.1 volts to about 1 volt, about 0.5 volts to about 2 volts, about 1 volt to about 9 volts, about 1 volt, about 3 volts, about 6 volts, or about 9 volts. In another example, the first voltage exhibits any of the voltages disclosed herein and the second voltage is greater than the first voltage by at least about 5% (including any percentages disclosed herein) or about 0.1 volts to about 75 volts (including any of the voltages disclosed herein). In another example, the second voltage exhibits any of the voltages disclosed herein and the first voltage is greater than the second voltage by at least about 5% (including any percentages disclosed herein) or about 0.1 volts to about 75 volts (including any of the voltages disclosed herein).

It is noted that the mechanisms shown in FIGS. 10-13 can be used in any of the flow assays shown in FIGS. 1A-8.

Figure 10:
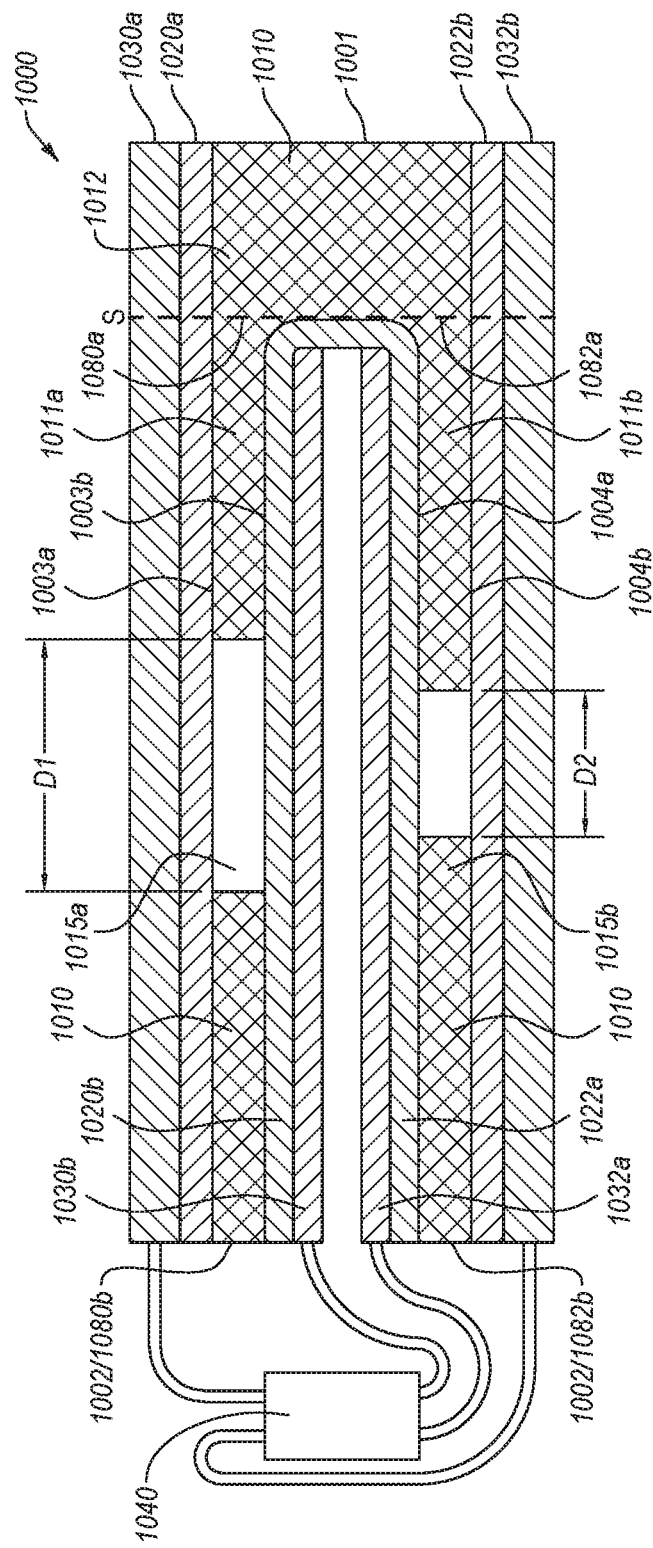
FIG. 10 is a front cross-sectional view of a flow assay according to an embodiment.

FIG. 10 illustrates a flow assay 1000 according to an embodiment. Except as otherwise disclosed herein, the flow assay 1000 can be substantially the same as or similar to any of the flow assays disclosed herein. For example, the flow assay includes a proximal end 1001 and a plurality of distal ends 1002 opposite the proximal end 1001. The flow assay 1000 includes at least one common area 1012 that is at, near, or fluidly coupled to the proximal end 1001. The flow assay 1000 also includes at least one first branch 1011a and at least one second branch 1011b on the distal end 1002 side of the reference line S that are positioned in parallel with each other. The first and second branches 1011a and 1011b extend longitudinally from the common area 1012, such as from the reference line S towards (e.g., to) the distal ends 1002. The first and second branches 1011a and 1011b can be separated by a space therebetween extending from a point intermediate to the proximal and distal ends 1001 and 1002 (marked by reference line S) towards the distal ends 1002. The first and second branches 1011a and 1011b are also fluidly coupled to the common area 1012. As such, any fluid that is introduced into, flows into, or is otherwise present in the common area 1012 can flow into at least a portion of the first or second branch 1011a and 1011b.

The hydrophilic porous layer 1010 of the first branch 1011a extends from a first proximal branch end 1080a that is adjacent to the common area to a first distal branch end 1080b spaced from the first proximal branch end 1080a. The first distal branch end 1080b can be at or near the distal end 1002. The hydrophilic porous layer 1010 of the first branch 1011a also includes a first side 1003a spaced from a second side 1003b. The first branch 1011a also includes at least one first hydrophobic layer 1020a disposed adjacent to the first side 1003a, at least one second hydrophobic layer 1020b disposed adjacent to the second side 1003b, a first electrode 1030*a* separated from the hydrophilic porous layer 1010 of the first branch 1011*a* by the first hydrophobic layer 1020*a*, and a second electrode 1030*b* that are each separated from the hydrophilic porous layer 1010 of the first branch 1011*a* by the second hydrophobic layer 1020*b*. Also, the first branch 1011*a* includes at least one first gap 1015*a* located between the first proximal branch end 1080*a* and the first distal branch end 1080*b* that is partially defined by the first and second hydrophobic layers 1020*a* and 1020*b*.

Except as otherwise disclosed herein, the second branch 1011*b* can be the same as or substantially similar to the first branch 1011*a*. For example, hydrophilic porous layer 1010 of the second branch 1011*b* extends from a second proximal branch end 1082*a* to a second distal branch end 1082*b* spaced from the second proximal branch end 1082*a*. The hydrophilic porous layer 1010 of the second branch 1011*b* can also include a third side 1004*a* spaced from a fourth side 1004*b*. The second branch 1011*b* also includes at least one third hydrophobic layer 1022*a* disposed adjacent to the third side 1004*a*, at least one fourth hydrophobic layer 1022*b* disposed adjacent to the fourth side 1004*b*, a third electrode 1032*a* separated from the hydrophilic porous layer 1010 of the second branch 1011*b* by the third hydrophobic layer 1022*a*, and a fourth electrode 1032*b* separated from the hydrophilic porous layer 1010 of the second branch 1011*b* by the fourth hydrophobic layer 1022*b*. Also, the second branch 1011*b* includes at least one second gap 1015*b* located between the second proximal branch end 1082*a* and the second distal branch end 1082*b* that is partially defined by the third and fourth hydrophobic layers 1022*a* and 1022*b*.

The voltage required to enable the sample to flow across one of the first or second gaps 1015*a* or 1015*b* depends at least in part on the distance between adjacent portions or segments of the hydrophilic porous layer 1010 that at least partially defines the first and second gaps 1015*a* and 1015*b*, respectively. In an embodiment, the first gap 1015*a* is at least partially defined by a first distance D1 between adjacent portions or segments of the hydrophilic porous layer 1010 of the first branch 1011*a*. The first distance D1 is selected to require application of a first voltage from the power source 1040 to enable a sample to flow across the first gap 1015*a*. Similarly, second gap 1015*b* is at least partially defined by a second distance D2 between adjacent portions of segments of the hydrophilic porous layer 1010 of the second branch 1011*a*. The second distance D2 is selected to require application of a second voltage from the power source 1140 that is different from the first voltage to enable a sample to flow across the second gap 1015*b*. The first distance D1 is different than the second distance D2.

For example, one of the first or second distance D1 or D2 is greater than the other of the first or second distance D1 or D2 by at least about 5%, at least about 10%, at least about 15%, at least about 25%, at least about 50%, at least about 75%, at least about 100%, at least about 150%, at least about 200%, at least about 300%, about 5% to about 50%, about 25% to about 75%, about 50% to about 100%, about 75% to about 150%, about 100% to about 200%, or about 150% to about 300%. In another example, one of the first or second distance D1 or D2 is greater than the other of the first or second distance D1 or D2 by about 0.001 inches or more, such as about 0.001 inches to about 1 inch, about 0.005 inches to about 0.5 inches, about 0.01 inches to about 0.05 inches, about 0.02 inches to about 0.04 inches, about 0.02 inches to about 0.3 inches, about 0.05 inches to about 0.5 inches, about 0.01 inches or more, about 0.025 inches or more, about 0.05 inches or more, about 0.1 inches or more, about 0.25 inches or more, or about 0.5 inches or more. In another example, the first distance D1 exhibits any of the distances disclosed herein and the second distance D2 is greater than the first distance D1 by at least about 5% (including any of the percentage disclosed herein) or about least about 0.001 inches (including any of the distances disclosed herein). In another example, the second distance D2 exhibits any of the distances disclosed herein and the first distance D1 is greater than the second distance D2 by at least about 5% (including any of the percentage disclosed herein) or about least about 0.001 inches (including any of the distances disclosed herein).

As previously discussed, the flow assay 1000 includes at least one conjugate or taggant. In an embodiment, the conjugate or taggant can be disposed in or on the common area 1012. As such, the portions of the sample that enter the first branch 1011*a* and the second branch 1011*b* have an opportunity to react with the conjugate or taggant. In an embodiment, the at least one conjugate or taggant can be disposed in or on the first branch 1011*a* or the second branch 1011*a*. For example, the at least one conjugate or taggant can include at least one first conjugate or taggant that is disposed in or on at least the first branch 1011*a* (e.g., between the first proximal branch end 1080*a* and the first gap 1015*a*) and at least one second conjugate or taggant disposed in or on at least the second branch 1011*b* (e.g., between the second proximal branch end 1082*a* and the second gap 1015*b*). The first conjugate or taggant is different than the second conjugate or taggant. For instance, the first conjugate or taggant and the second conjugate or taggant can be selected to react with different analytes in the same sample.

Figure 11:
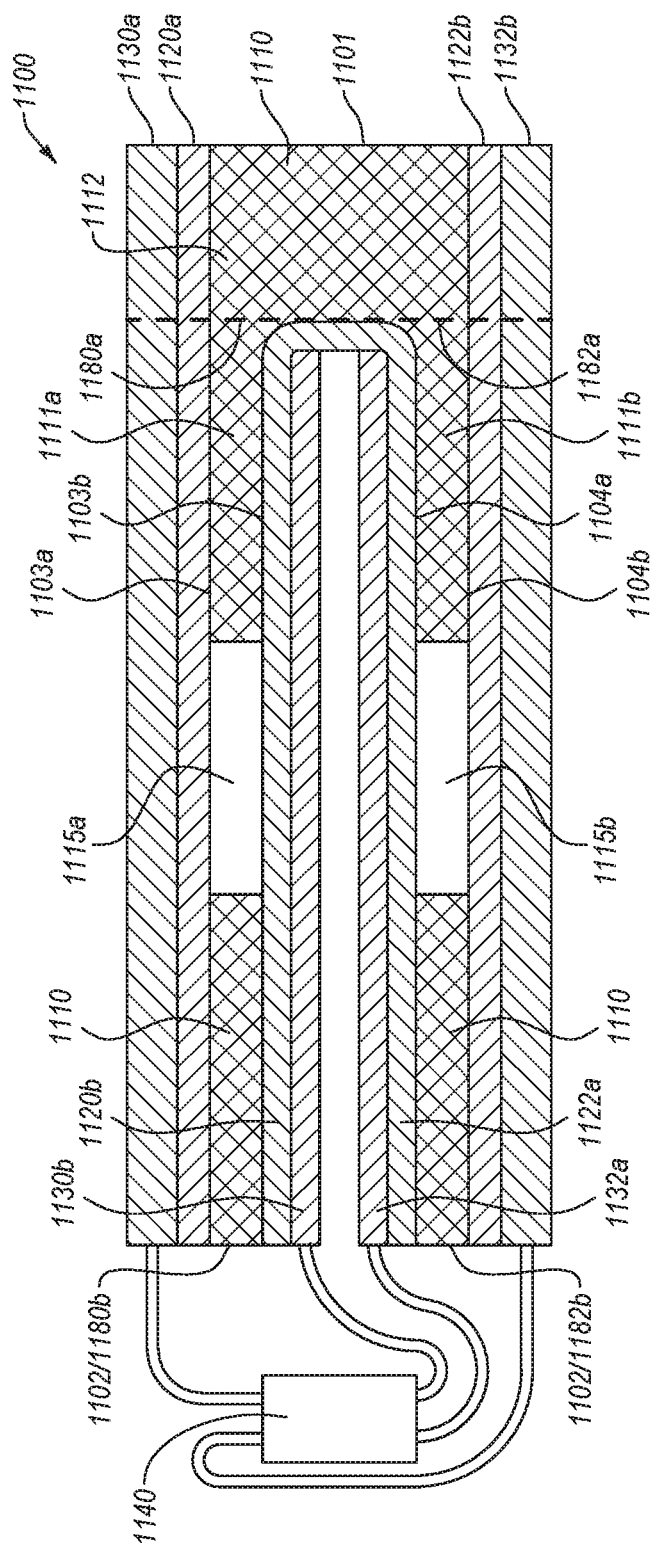
FIG. 11 is a front cross-sectional view of a flow assay according to an embodiment.

FIG. 11 illustrates a flow assay 1100 according to an embodiment. Except as otherwise disclosed herein, the flow assay 1100 can be substantially the same as or similar to any of the flow assays disclosed herein. For example, the flow assay 1100 includes a proximal end 1101 and a plurality of distal ends 1102. The flow assay 1100 includes at least one common area 1112, at least one first branch 1111*a*, and at least one second branch 1111*b*.

The first branch 1111*a* includes at least one hydrophilic porous layer 1110 extending from a first proximal branch end 1180*a* to a first distal branch end 1180*b*. The hydrophilic porous layer 1110 of the first branch 1111*a* also includes a first side 1103*a*, a second side 1103*b*, and at least one first gap 1115*a* located between the first proximal branch end 1180*a* and the first distal branch end 1180*b*. The first branch 1111*a* also includes at least one first hydrophobic layer 1120*a* disposed adjacent to the first side 1103*a* that partially defines the first gap 1115*a*, at least one second hydrophobic layer 1120*b* disposed adjacent to the second side 1103*b* that partially defines the first gap 1115*a*, a first electrode 1130*a* separated from the hydrophilic porous layer 1110 by the first hydrophobic layer 1120*a*, and a second electrode 1130*b* that is separated from the hydrophilic porous layer 1110 by the second hydrophobic layer 1120*b*.

Except as otherwise disclosed herein, the second branch 1111*b* can be the same as or substantially similar to the first branch 1111*a*. For example, the hydrophilic porous layer 1110 of the second branch 1411*b* extends from a second proximal branch end 1182*a* to a second distal branch end 1182*b*. The hydrophilic porous layer 1110 of the second branch 1111*b* also includes a third side 1104*a*, a fourth side 1104*b*, and at least one second gap 1115*b* located between the second proximal branch end 1182*a* and the second distal branch end 1182*b*. The second branch 1111*b* also includes at least one third hydrophobic layer 1122*a*, at least one fourth hydrophobic layer 1122*b*, a third electrode 1132*a*, and a fourth electrode 1132*b*.

The first and second hydrophobic layers 1120a and 1120b collectively exhibit a first hydrophobicity. The third and fourth hydrophobic layers 1122a and 1122b collectively exhibit a second hydrophobicity that is different than the first hydrophobicity. The first and second hydrophobicities are different when at least one of the contact angle between at least one of the first or second hydrophobic layers 1120a or 1120b and the contact angle between at least one of the third or fourth hydrophobic porous material 1122a or 1122b are different when at least one voltage (e.g., no voltage, the first voltage, or the second voltage) is applied to the first, second, third, and fourth electrodes 1130a, 1130b, 1132a, and 1132b. The voltage required to enable the sample to flow across one of the gaps 1115a or 1115b of the flow assay 1100 depends at least in part on the first hydrophobicity and 1120b and the second hydrophobicity. For example, the first and second hydrophobic layers 1120a and 1120b are selected to collectively exhibit a first hydrophobicity that requires application of a first voltage from the power source 1140 to enable the sample to flow across the first gap 1115a. The third and fourth hydrophobic materials 1122a and 1122b are selected to collectively exhibit a second hydrophobicity that requires application a second voltage from the power source 1140 to enable the sample to flow across the second gap 1115b. The first voltage is different than the second voltage.

In an embodiment, the first hydrophobicity is different than the second hydrophobicity because at least one of (e.g., both of) the first and second hydrophobic layers 1120a and 1120b and at least one of (e.g., both of) the third and fourth hydrophobic porous materials 1122a and 1122b include different materials. In an embodiment, the first hydrophobicity is different than the second hydrophobicity because at least one of (e.g., both of) the first and second hydrophobic layers 1120a and 1120b and at least one of (e.g., both of) the third and fourth hydrophobic porous materials 1122a and 1122b include different microstructures or nanostructures.

The first and second gaps 1115a and 1115b are at least partially defined by substantially the same or different distances between adjacent portions or segments of the hydrophilic porous layer 1110 of the first and second branches 1111a and 1111b, respectively.

Figure 12:
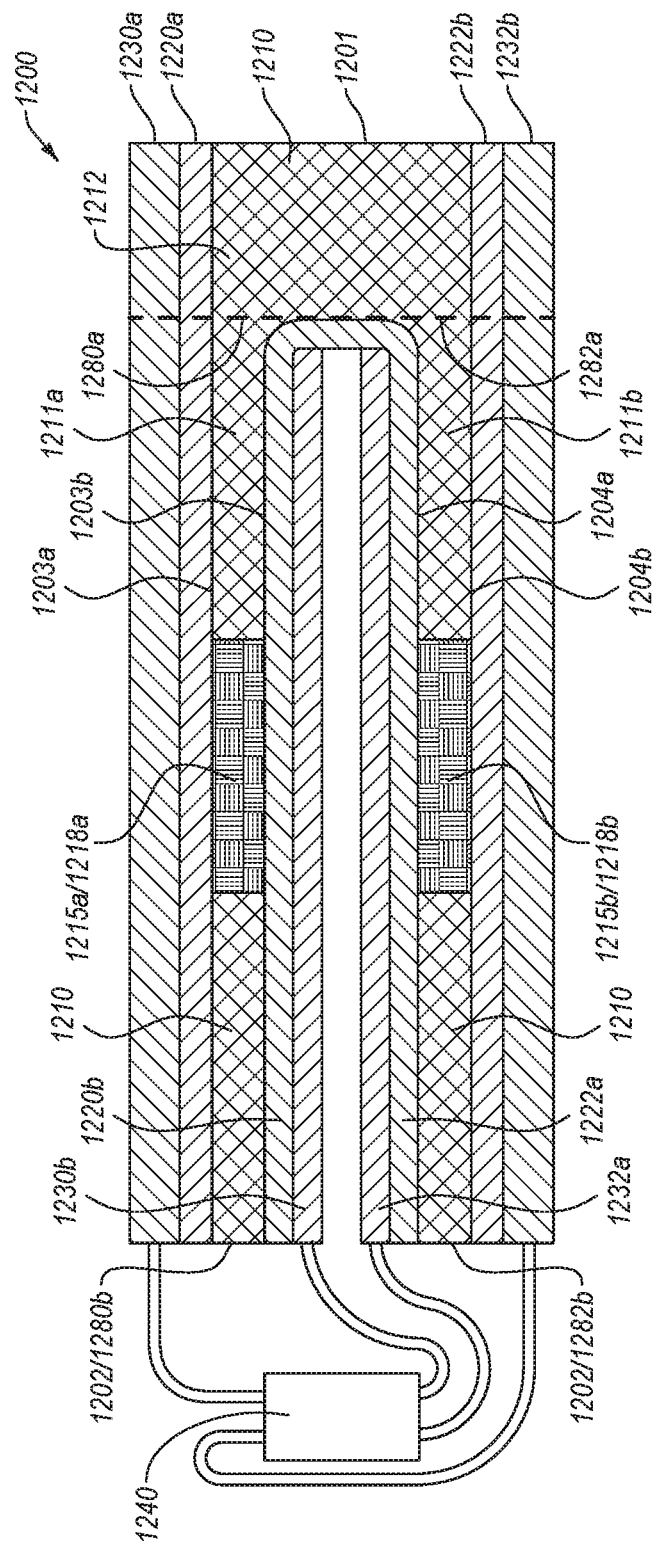
FIG. 12 is a front cross-sectional view of a flow assay according to an embodiment.

FIG. 12 illustrates a flow assay 1200 according to an embodiment. Except as otherwise disclosed herein, the flow assay 1200 can be substantially the same as or similar to any of the flow assays disclosed herein. For example, the flow assay 1200 includes a proximal end 1201, at least one distal end 1202, at least one common area 1212, at least one first branch 1211a, and at least one second branch 1211b.

The first branch 1211a includes at least one hydrophilic porous layer 1210 extending from a first proximal branch end 1280a to a first distal branch end 1280b. The hydrophilic porous layer 1210 of the first branch 1211a includes a first side 1203a, a second side 1203b, and at least one first gap 1215a located between the first proximal branch end 1280a and the first distal branch end 1280b. The first branch 1211a also includes at least one first hydrophobic layer 1220a disposed adjacent to the first side 1203a that partially defines the first gap 1215a, at least one second hydrophobic layer 1220b disposed adjacent to the second side 1203b that partially defines the first gap 1215a, a first electrode 1230a separated from the hydrophilic porous layer 1210 by the first hydrophobic layer 1220a, and a second electrode 1230b that is separated from the hydrophilic porous layer 1210 by the second hydrophobic layer 1220b Except as otherwise disclosed herein, the second branch 1211b can be the same as or substantially similar to the first branch 1211a. For example, the second branch 1211b includes at least one hydrophilic porous layer 1210 extending from a second proximal branch end 1282a to the common area 1212 to a second distal branch end 1282b. The hydrophilic porous layer 1210 of the second branch 1211b includes a third side 1204a, a fourth side 1204b, and at least one second gap 1215b. The second branch 1211b also includes at least one third hydrophobic layer 1222a, at least one fourth hydrophobic layer 1222b, a third electrode 1232a, and a fourth electrode 1232b.

The first gap 1215a is at least partially filled with at least one first hydrophobic porous material 1218a and the second gap 1215a is at least partially filled with at least one second hydrophobic porous material 1218b. The first and second hydrophobic porous materials 1218a and 1218b can be substantially the same as or similar to the hydrophobic porous material 418 of FIG. 4. For example, the first and second hydrophobic porous materials 1218a and 1218b can function to prevent the sample from progressing across the first and second gaps 1215a and 1215b, respectively. The first and second hydrophobic porous material 1218a and 1218b can be configured to reduce in hydrophobicity, become at least partially hydrophilic, or otherwise aid or allow the sample to progress across the first and second gaps 1215a and 1215b upon application of a voltage from the power source 1240.

In an embodiment, the first hydrophobic porous material 1218a exhibits a first hydrophobicity and the second hydrophobic porous material 1218b exhibits a second hydrophobicity that is different than the first hydrophobicity. The voltage required to enable the sample to flow across one of the first or second gaps 1215a or 1215b depends at least in part on the first and second hydrophobicities of the first and second hydrophobic porous materials 1218a and 1218b. For example, at least one of the first or second hydrophobic porous materials 1218a or 1218b can be configured to reduce in hydrophobicity, become at least partially hydrophilic, or otherwise aid or allow the ample to process across the first or second gap 1215a or 1215b, respectively, upon application of voltage from the power source 1240. As such, the first hydrophobic porous material 1218a can be selected to exhibit a first hydrophobicity that requires application of the first voltage from the power source 1240 to enable the sample to flow across the first gap 1215a. Similarly, the second hydrophobic porous material 1218b can be selected to exhibit a first hydrophobicity that requires application of the second voltage from the power source 1240 to enable the sample to flow across the second gap 1215b.

In an embodiment, the first hydrophobicity is different than the second hydrophobicity because the first hydrophobic porous material 1218a and the second hydrophobic porous material 1218b include different materials. In an embodiment, the first hydrophobicity is different than the second hydrophobicity because the first hydrophobic porous material 1218a and the second hydrophobic porous material 1218b include different microstructures or nanostructures.

In an embodiment, the first and second gaps 1215a and 1215b are at least partially defined by the same or different distances between adjacent portions of the hydrophilic porous layer of the first and second branches 1211a and 1211b, respectively. In an embodiment, the first and second hydrophobic layers 1220a and 1220b collectively exhibit a first hydrophobicity and the third and fourth hydrophobic layers 1222a and 1222b collectively exhibit a second hydrophobicity. In such an embodiment, the first and second hydrophobicities are the same or different.

Figure 13:
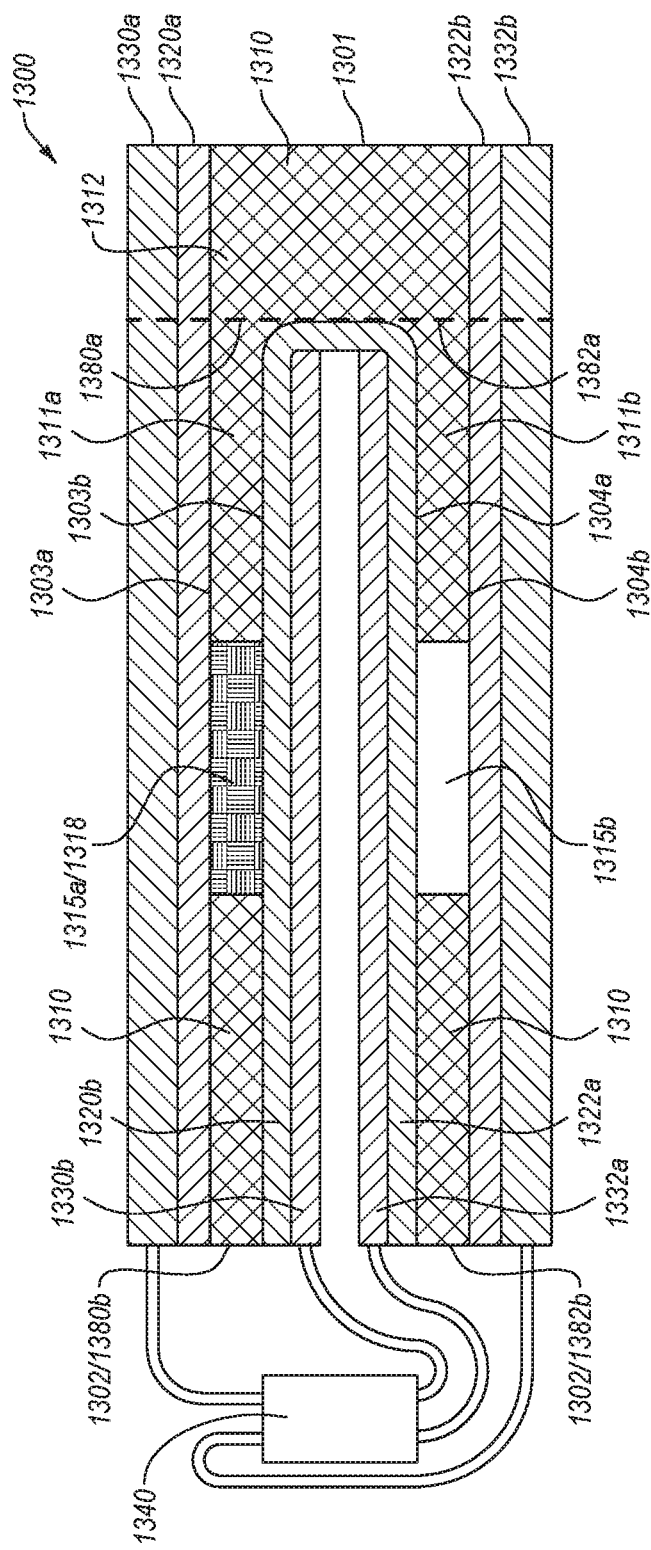
FIG. 13 is a front cross-sectional view of a flow assay according to an embodiment.

FIG. 13 illustrates a flow assay 1300 according to an embodiment. Except as otherwise disclosed herein, the flow assay 1300 can be substantially the same as or similar to any of the flow assays disclosed herein. For example, the flow assay 1300 includes a proximal end 1301, at least one distal end 1302, at least one common area 1312, at least one first branch 1311a, and at least one second branch 1311b.

The first branch 1311a includes at least one hydrophilic porous layer 1310 extending from a first proximal branch end 1380a to a first distal branch end 1380b. The hydrophilic porous layer 1310 of the first branch 1311a includes a first side 1303a, a second side 1303b, and at least one first gap 1315a. The first branch 1311a also includes at least one first hydrophobic layer 1320a, at least one second hydrophobic layer 1320b, a first electrode 1330a, and a second electrode 1330b.

Except as otherwise disclosed herein, the second branch 1311b can be the same as or substantially similar to the first branch 1311a. For example, the second branch 1311b includes at least one hydrophilic porous layer 1310 extending from a second proximal branch end 1382a to a second distal branch end 1382b. The hydrophilic porous layer 1310 of the second branch 1311b includes a third side 1304a, a fourth side 1304b, and at least one second gap 1315b. The second branch 1311b also includes at least one third hydrophobic layer 1322a, at least one fourth hydrophobic layer 1322b, a third electrode 1332a, and a fourth electrode 1332b.

The first gap 1315a is at least partially filled with at least one hydrophobic porous material 1318. The hydrophobic porous material 1318 can be the same or similar to the hydrophobic porous material 418 of FIG. 4. The second gap 1315a is at least occupied with air (e.g., substantially free of a porous material or layer). The voltage required to enable the sample to flow across one of the first or second gap 1315a or 1315b depends at least in part on whether the first or second gaps 1315a or 1315b is at least partially occupied by the hydrophobic porous material 1318 or air. For example, the hydrophobic porous material 1318 can be selected to require application of a first voltage from the power source 1340 to enable the sample to flow across the first gap 1315a. Similarly, the second gap 1315a can be configured to require application of a second voltage that is different than the first voltage from the power source 1340 to enable the sample to flow across the second gap 1315b.

In an embodiment, the first and second gaps 1315a and 1315b are at least partially defined by the same or different distances between adjacent portions of the hydrophilic porous layer of the first and second branches 1311a and 1311b, respectively. In an embodiment, the first and second hydrophobic layers 1320a and 1320b collectively exhibit a first hydrophobicity and the third and fourth hydrophobic layers 1322a and 1322b collectively exhibit a second hydrophobicity. In such an embodiment, the first and second hydrophobicities are the same or different.

Figure 14:
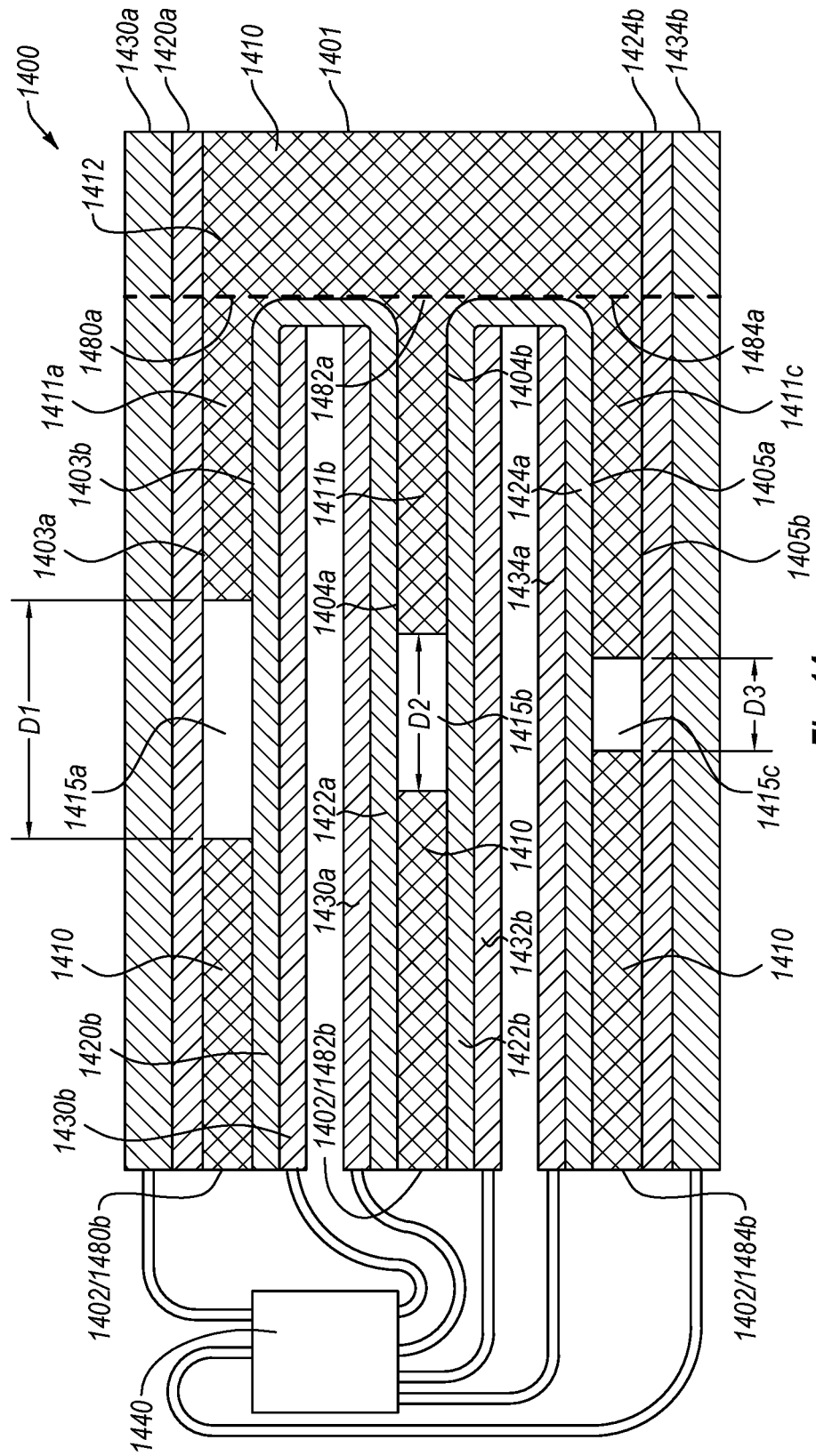
FIG. 14 is a front cross-sectional view of a flow assay according to an embodiment.

In FIGS. 1-8 and 10-13, the flow assays are illustrated as including one or two branches. However, any of the flow assays disclosed herein can include three or more branches. FIG. 14 illustrates a flow assay 1400 that includes three or more branches according to an embodiment. Except as otherwise disclosed herein, the flow assay 1400 can be substantially the same as or similar to any of the flow assays disclosed herein. For example, the flow assay 1400 includes a proximal end 1401, at least one distal end 1402, at least one common area 1412, at least one first branch 1411a, at least one second branch 1411b that is positioned in parallel with the first branch 1411a. The flow assay 1400 can also include one or more additional branches, such as at least one third branch 1411c, that are positioned in parallel with the first and second branches 1411a and 1411b.

The first, second, and third branches 1411a, 1411b, and 1411c include at least one hydrophilic porous layer 1410. The common area 1412 can also include at least one hydrophilic porous layer 1410. In an embodiment, as illustrated, the hydrophilic porous layer 1410 of at least a portion of the first branch 1411a, at least a portion of the second branch 1411b, at least a portion of the third branch 1411c, and the common area 1412 are formed from the same material and collectively form a continuous hydrophilic porous layer. In another embodiment, the hydrophilic porous layer 1410 of at least two of at least a portion of the first branch 1411a, at least a portion of the second branch 1411b, at least a portion of the third branch 1411c, or the common area 1412 are formed from different material or are discontinuous.

The hydrophilic porous layer 1410 of the first branch 1411a extends from a first proximal branch end 1480a to a first distal branch end 1480b. The hydrophilic porous layer 1410 of the first branch 1411a includes a first side 1403a, a second side 1403b, and at least one first gap 1415a. The first branch 1411a also includes at least one first hydrophobic layer 1420a, at least one second hydrophobic layer 1420b, a first electrode 1430a, and a second electrode 1430b.

Except as otherwise disclosed herein, the second branch 1411b can be the same as or substantially similar to the first branch 1411a. For example, the hydrophilic porous layer 1410 of the second branch 1411b extends from a second proximal branch end 1482a to a second distal branch end 1482b. The hydrophilic porous layer 1410 of the second branch 1411b includes a third side 1404a, a fourth side 1404b, and at least one second gap 1415b. The second branch 1411b also includes at least one third hydrophobic layer 1422a, at least one fourth hydrophobic layer 1422b, a third electrode 1432a, and a fourth electrode 1432b.

Except as otherwise disclosed herein, the third branch 1411c can be the same as or substantially similar to the first and second branches 1411a and 1411b. For example, the hydrophilic porous layer 1410 of the third branch 1411c extends from a third proximal branch end 1484a to a third distal branch end 1484b. The hydrophilic porous layer 1410 of the third branch 1411c includes a fifth side 1405a, a sixth side 1405b, and at least one first gap 1415c. The third branch 1411c also includes at least one fifth hydrophobic layer 1424a, at least one sixth hydrophobic layer 1424b, a fifth electrode 1434a, and a sixth electrode 1434b.

In an embodiment, application of a first voltage from the power source 1440 is required to enable a sample to flow across the first gap 1415a, application of a second voltage from the power source 1440 is required to enable a sample to flow across the second gap 1415c, and application of a third voltage from the power source 1440 is required to enable a sample to flow across the third gap 1415c. At least two of the first, second, or third voltages are different. The third voltage can include any of the voltages described above. In an embodiment, the power source 1440 can be configured to apply the same voltage to the first and second electrodes 1430a and 1430b, the third and fourth electrodes 1432a and 1432b, and the fifth and sixth electrodes 1434a and 1434b. In another embodiment, the power source 1440 can selectively apply different voltages to at least two of the first and second electrodes 1430a and 1430b, the third and fourth electrodes 1432a and 1432b, or the fifth and sixth electrodes 1434a and 1434b. For example, the power source 1440 can apply the first voltage to the first and second electrodes 1430a and 1430b and different voltages (e.g., no voltage, the second voltage, or the third voltage) to the third and fourth electrodes 1432a and 1432b and the fifth and sixth electrodes 1434a and 1434b.

The first, second, and third branches 1411a, 1411b, and 1411c can be configured to controllably and selective enable the sample to flow across the gaps thereof using any of the mechanisms disclosed in FIGS. 10-13. For example, as illustrated, the first, second, and third gaps 1415a, 1415b, and 1415c are at least partially defined by a first distance D1, a second distance D2, and a third distance D3 between adjacent portions or segments of the hydrophilic porous layer 1410. In such an example, at least two of the first, second, or third distances D1, D2, or D3 are different. In another example, the first and second hydrophobic layers 1420a and 1420b collectively exhibit a first hydrophobicity, the third and fourth hydrophobic layers 1422a and 1422b collectively exhibit a second hydrophobicity, and the fifth and sixth hydrophobic layers 1424a and 1424b collectively exhibit a third hydrophobicity. In such an example, at least two of the first, second, and third hydrophobicities are different. In another example, the first gap 1415a is at least partially occupied by a first hydrophobic porous material exhibiting a first hydrophobicity, the second gap 1415b is at least partially occupied by a second hydrophobic porous material exhibiting a second hydrophobicity, and the third gap 1415c is at least partially occupied by a third hydrophobic porous material exhibiting a third hydrophobicity. In such an example, at least two of the first, second, or third hydrophobicities are different. In another example, at least one of the first, second, or third gaps 1415a, 1415b, or 1415c is at least partially occupied by at least one hydrophobic porous material and a remainder of the first, second, or third gaps 1415a, 1415b, or 1415c is at least partially occupied by air.

It is understood that the flow assay 1400 can include three or more branches, such as 4, 5, 6, 7, 8, 9, 10, or more than 10 branches that are each positioned in parallel with each other. Each of the three or more branches can be configured the same as or similar to any of the branches disclosed herein.

Figure 15:
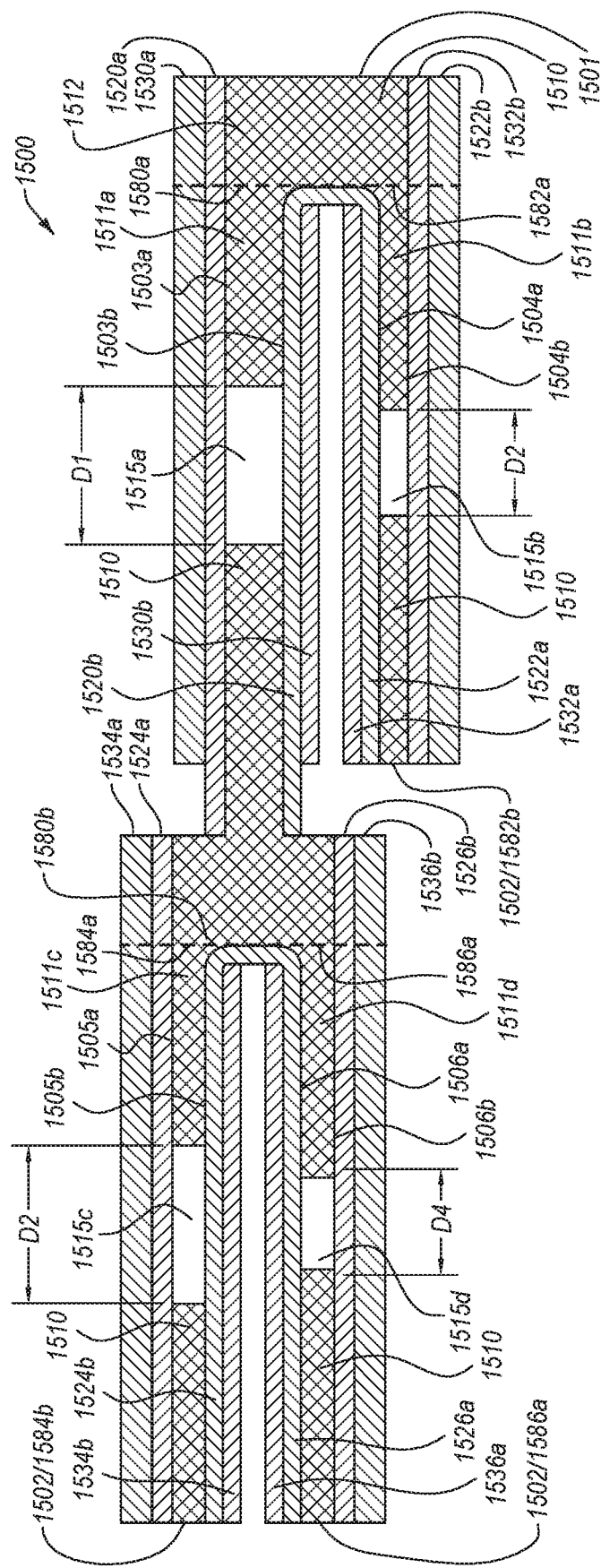
FIG. 15 is a front cross-sectional view of a flow assay according to an embodiment.

In FIGS. 8 and 10-14, the flow assays illustrate a plurality of branches that are positioned in parallel with each other. However, any of the flow assays disclosed herein can include branches are positioned in series with each other. FIG. 15 illustrates a flow assay 1500 that includes a plurality of branches according to an embodiment. Except as otherwise disclosed herein, the flow assay 1500 can be substantially the same as or similar to any of the flow assays disclosed herein. For example, the flow assay 1500 includes a proximal end 1501, at least one distal end 1502, at least one common area 1512, at least one first branch 1511a, and at least one second branch 1511b that is positioned in parallel with the first branch 1511a. The flow assay 1500 can also include at least one third branch 1511c that is positioned in series with the first branch 1511a and at least one fourth branch 1511d that is positioned in series with the first branch 1511a and in parallel with the third branch 1511c.

The first and second branches 1511a and 1511b can be the same as or substantially similar to any of the branches disclosed herein. For example, the first branch 1511a can include at least one hydrophilic porous layer 1510 extending from a first proximal branch end 1580a to a first distal branch end 1580b. The hydrophilic porous layer 1510 of the first branch 1511a includes a first side 1503a, a second side 1503b, and at least one first gap 1515a. The first branch 1511a also includes at least one first hydrophobic layer 1520a, at least one second hydrophobic layer 1520b, a first electrode 1530a, and a second electrode 1530b. Similarly, the second branch 1511b can include at least one hydrophilic porous layer 1510 extending from a second proximal branch end 1582a that is adjacent to the common area 1512 to a second distal branch end 1582b. The hydrophilic porous layer 1510 of the second branch 1511b includes a third side 1504a, a fourth side 1504b, and at least one second gap 1515b. The second branch 1511b also includes at least one third hydrophobic layer 1522a, at least one fourth hydrophobic layer 1522b, a third electrode 1532a, and a fourth electrode 1532b.

Portions of the first branch 1511a at or near the first distal branch end 1580b of the first branch 1511a can act as a common area for the third and fourth branches 1511c and 1511d. For example, the third and fourth branches 1511c and 1511d are fluidly coupled to and extend longitudinally from the first distal branch end 1580b.

The third branch 1511c and the fourth branch 1511d include at least one hydrophilic porous layer 1510. In an embodiment, as illustrated, the hydrophilic porous layer 1510 of at least a portion of the first branch 1511a, at least a portion of the third branch 1511c, and at least a portion of the fourth branch 1511d are formed from the same material and collectively form a continuous hydrophilic porous layer. In another embodiment, the hydrophilic porous layer 1510 of at least two of at least a portion of the first branch 1511a, at least a portion of the third branch 1511c, and at least a portion of the fourth branch 1511d are formed from different materials or are discontinuous.

Except as otherwise disclosed herein, the third branch 1511c can be substantially the same as or similar to the first or second branch 1511a or 1511b. For example, the hydrophilic porous layer 1510 of the third branch 1511c extends from a third proximal branch end 1584a that is adjacent to the first distal branch end 1580b to a third distal branch end 1584b. The hydrophilic porous layer 1510 of the third branch 1511c includes a fifth side 1505a, a sixth side 1505b, and at least one third gap 1515c. The third branch 1511c also includes at least one fifth hydrophobic layer 1524a, at least one sixth hydrophobic layer 1524b, a fifth electrode 1534a, and a sixth electrode 1534b.

Similarly, except as otherwise disclosed herein, the fourth branch 1511d can be substantially the same as or similar to the first, second, or third branch 1511a, 1511a, or 1511c. For example, the hydrophilic porous layer 1510 of the fourth branch 1511d extends from a fourth proximal branch end 1586a that is adjacent to the first distal branch end 1580b to a fourth distal branch end 1586b. The hydrophilic porous layer 1510 of the fourth branch 1511d includes a seventh side 1506a, an eighth side 1506b, and at least one fourth gap 1515d. The fourth branch 1511d also includes at least one seventh hydrophobic layer 1526a, at least one eighth hydrophobic layer 1526b, a seventh electrode 1536a, and an eighth electrode 1536b.

The flow assay 1500 can be configured to enable the sample to flow across the first, second, third, and fourth gaps 1515a, 1515b, 1515c, and 1515d upon application of a first, second, third, and fourth voltage from the power source (not shown), respectively, using any of the mechanisms disclosed in FIGS. 10-13, where at least two of the first, second, third, or fourth voltages are different. For example, as illustrated, the first, second, third, and fourth gaps 1515a, 1515b, 1515c, and 1515d are at least partially defined by a first, second, third, and fourth distances D1, D2, D3, and D4, respectively, between adjacent portions or segments of the hydrophilic porous layer 1510. In such an example, at least two of the first, second, third, or fourth distances D1, D2, D3, or D4 are different. In another example, the first and second hydrophobic layers 1520a and 1520b collectively exhibit a first hydrophobicity, the third and fourth hydrophobic layers 1522a and 1522b collectively exhibit a second hydrophobicity, the fifth and sixth hydrophobic layers 1524a and 1524b collectively exhibit a third hydrophobicity, and the seventh and eighth hydrophobic layers 1526a and 1526b collectively exhibit a fourth hydrophobicity. In such an example, at least two of the first, second, third, or the fourth hydrophobicities are different. In another example, the first gap 1515a is at least partially occupied by a first hydrophobic porous material exhibiting a first hydrophobicity, the second gap 1515b is at least partially occupied by a second hydrophobic porous material exhibiting a second hydrophobicity, the third gap 1515c is at least partially occupied by a third hydrophobic porous material exhibiting a third hydrophobicity, and the fourth gap 1515d is at least partially occupied by a fourth hydrophobic porous material exhibiting a fourth hydrophobicity. In such an example, at least two of the first, second, third, or the fourth hydrophobicities are different. In another example, at least one of the first, second, third, or fourth gaps 1515a, 1515b, 1515c, 1515d is at least partially occupied by at least one hydrophobic porous material and a remainder of the first, second, third, or fourth gaps 1515a, 1515b, 1515c, 1515d is at least partially occupied by air.

In an embodiment, the power source applies the same voltage to the electrodes of the first, second, third, and fourth branches 1511a, 1511b, 1511c, and 1511d simultaneously. In an embodiment, the power source selectively applies different voltages to the electrodes of at least two of the first, second, third, or fourth branches 1511a, 1511b, 1511c, or 1511d. For example, the power source can selectively apply a first voltage to the first and second electrodes 1530a and 1530b and a different voltage to at least one of the fifth and sixth electrodes 1534a and 1534b or the seventh or eighth electrodes 1536a and 1636b. The different voltage applied to the fifth and sixth electrodes 1534a and 1534b or the seventh or eighth electrodes 1536a and 1636b may not be sufficient to enable the portions of the sample that flowed across the first gap 1515a to also flow across at least one of the third or fourth gaps 1515c or 1515d.

In an embodiment, the first, second, third, and fourth branches 1511a, 1511b, 1511c, and 1511d are configured to detect different characteristics of the sample. For example, the first, second, third, and fourth branches 1511a, 1511b, 1511c, and 1511d are configured to detect different analytes that can be present in a sample or different concentrations of the same analyte. In an embodiment, only the second, third, and fourth branches 1511b, 1511c, and 1511d are configured to detect different characteristics of the sample. In such an embodiment, the first branch 1511a can controllably and selectively restrict access to the third and fourth branches 1511c and 1511d.

In an embodiment, the flow assay 1500 can include one or more additional branches (not shown) that are positioned in series with and extend longitudinally from the second branch 1511b. In an embodiment, at least one of the third or fourth branches 1511c or 1511d can also include one or more additional branches (not shown) that are positioned in series with and extend longitudinally therefrom.

Figure 16:
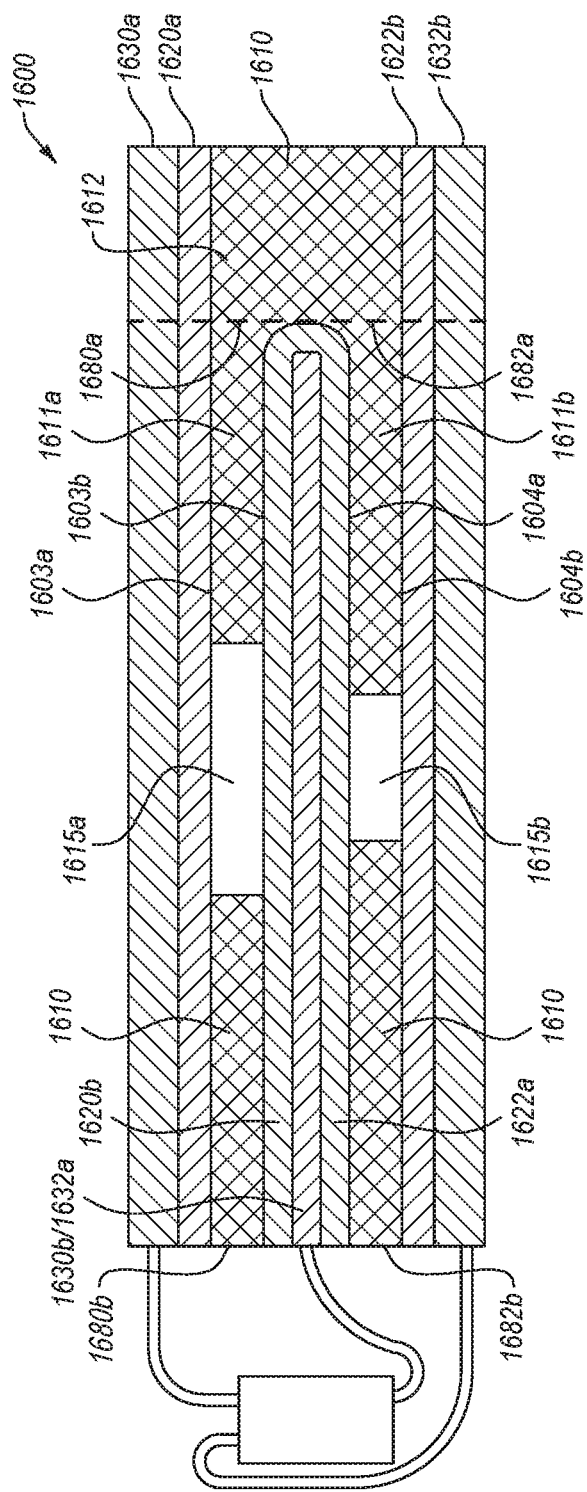
FIG. 16 is a front cross-sectional view of a flow assay according to an embodiment.

FIGS. 8 and 10-15 illustrate flow assays that include a plurality of branches having a space therebetween. FIG. 16 illustrates a flow assay 1600 that includes a plurality of branches without a space between adjacent branches according to an embodiment. Except as otherwise disclosed herein, the flow assay 1600 can be substantially the same as or similar to any of the flow assays disclosed herein. For example, the flow assay 1600 includes a proximal end 1601, at least one distal end 1602, a common area 1612, at least one first branch 1611a, and at least one second branch 1611b. The first and second branches 1611a and 1611b are not spaced apart and instead directly physically contact each other.

The first branch 1611a can include at least one hydrophilic porous layer 1610 that extends from a first proximal branch end 1680a to a first distal branch end 1680b. The hydrophilic porous layer 1610 of the first branch 1611a includes a first side 1603a, a second side 1603b, and at least one first gap 1615a. The first branch 1611a also includes at least one first hydrophobic layer 1620a, at least one second hydrophobic layer 1620b, a first electrode 1630a, and a second electrode 1630b. Similarly, the second branch 1611b includes at least one hydrophilic porous layer 1610 that extends from a second proximal branch end 1682a to a second distal branch end 1682b. The hydrophilic porous layer 1610 of the second branch 1611b includes a third side 1604a, a fourth side 1604b, and at least one second gap 1615b. The second branch 1611b also includes at least one third hydrophobic layer 1622a, at least one fourth hydrophobic layer 1622b, a third electrode 1632a, and a fourth electrode 1632b. The first, second, third, and fourth electrodes 1630a, 1630b, 1632a, and 1632b are electrically coupled to a power source 1640.

In an embodiment, the first and second branches 1611a and 1611b share one or more components therebetween. For example, as shown, the second and third electrodes 1630b and 1632a can be integrally formed together to form a common electrode. In another example, as previously discussed, the second and third hydrophobic layers 1620b and 1622a can be integrally formed together to form a continuous generally U-shaped hydrophobic layer that at least partially extends around the second and third electrodes 1630b and 1632a. In an embodiment, the first and second branches 1611a and 1611b do not share one or more components therebetween. For example, the second and third electrodes 1630b and 1632a can be distinct electrodes. In another example, the second and third hydrophobic layers 1620b and 1622a can be distinct hydrophobic layers.

Figure 17:
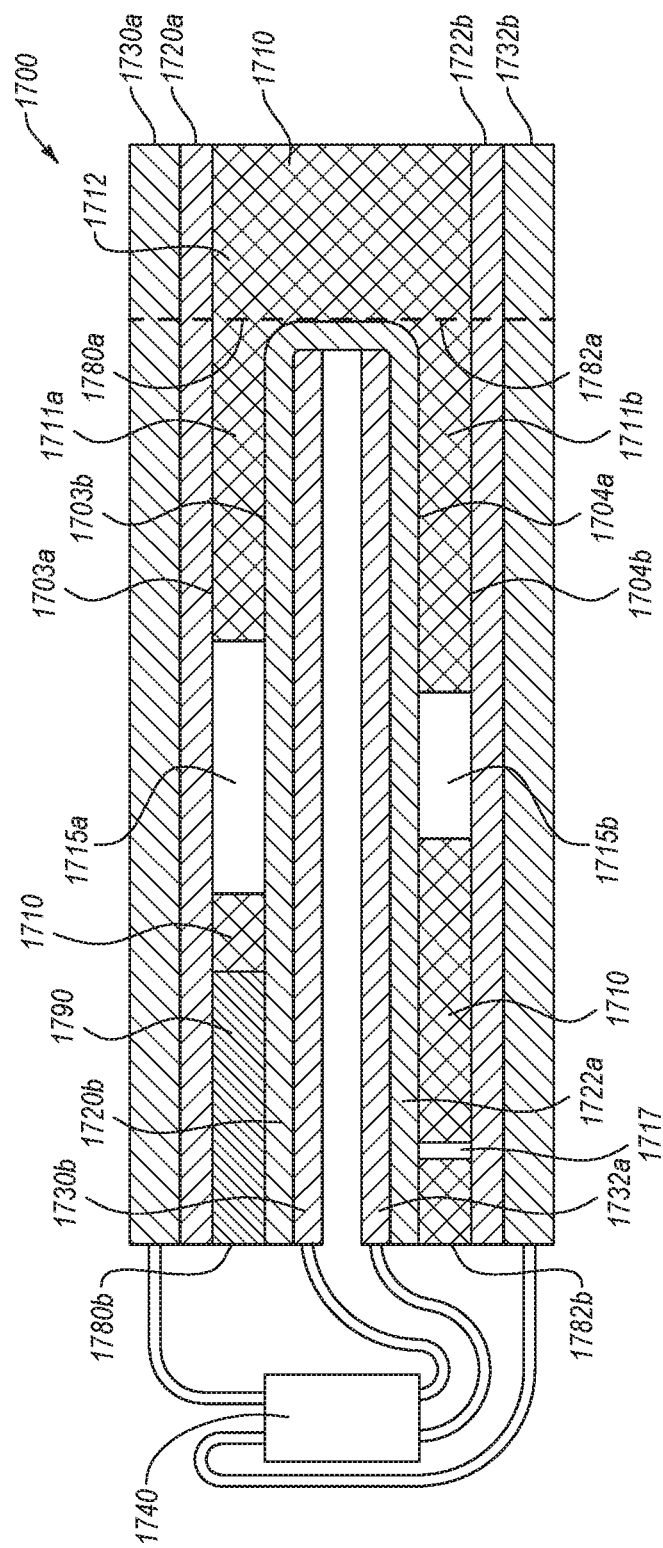
FIG. 17 is a front cross-sectional view of a flow assay according to an embodiment.

The branches illustrated in FIGS. 8 and 10-16 have been disclosed as being configured to detect one or more characteristics of a sample. However, any of the branches illustrated and discussed in relation to FIGS. 8 and 10-16 can be configured to affect the flow of the sample to at least one other branch instead of or in conjunction with detecting one or more characteristics of the sample. FIG. 17 illustrates a flow assay 1700 that includes a plurality of branches according to an embodiment. Except as otherwise disclosed herein, the flow assay 1700 can be substantially the same as or similar to any of the flow assays disclosed herein. For example, the flow assay 1700 can include a proximal end 1701, at least one distal end 1702, common area 1712, at least one first branch 1711a, and at least one second branch 1711a.

The first branch 1711a can include at least one hydrophilic porous layer 1710 that extends from a first proximal branch end 1780a to a first distal branch end 1780b. The hydrophilic porous layer 1710 of the first branch 1711a includes a first side 1703a, a second side 1703b, and at least one first gap 1715a. The first branch 1711a also includes at least one first hydrophobic layer 1720a, at least one second hydrophobic layer 1720b, a first electrode 1730a, and a second electrode 1730b. Similarly, the second branch 1711b can include at least one hydrophilic porous layer 1710 that extends from a second proximal branch end 1782*a* to a second distal branch end 1782*b*. The hydrophilic porous layer 1710 of the second branch 1711*b* includes a third side 1704*a*, a fourth side 1704*b*, and at least one second gap 1715*b*. The second branch 1711*b* also includes at least one third hydrophobic layer 1722*a*, at least one fourth hydrophobic layer 1722*b*, a third electrode 1732*a*, and a fourth electrode 1732*b*.

The first branch 1711*a* includes at least one dry waste region 1790 disposed between the first gap 1715*aa* and the first distal branch end 1780*b*. The dry waste region 1790 includes a reservoir that is configured to receive and store a portion of the sample therein. For example, the dry waste region 1790 can include a porous structure that is configured to receive and store the sample by wicking the sample. In such an example, the dry waste region 1790 can form a portion of the hydrophilic porous material, such as a portion of the hydrophilic porous material exhibiting a thickness that is greater than an average thickness of the hydrophilic porous material. In another example, the dry waste region 1790 can include a hollow structure defining a chamber (e.g., a container) and an inlet. The inlet can be configured to allow a portion of the sample to flow into the chamber.

The second branch 1711*b* can include at least one indicator portion 1717 that is located between the second distal branch end 1782*b* and the second gap 1715*b*. The indicator portion 1717 can be the same as or substantially similar to the indicator portion 117 shown in FIG. 2D. For example, the indicator portion 1717 can be configured to detect one or more characteristics of the sample and include at least one view area or indicator strip. It is noted that the first branch 1711*a* may or may not also include at least one indicator portion.

In operation, the dry waste region 1790 can be configured to control the volume and the flow rate of the sample that reaches at least the second branch 1711*b*. For example, the flow assay 1700 can detect that the volume or flow rate of the sample exceeds an operable value. The flow assay 1700 can detect the volume or flow rate of the sample using sensors (e.g., sensors 672*a* or 672*b* of FIG. 6B). Responsive to detecting the volume or flow rate of the sample, control electrical circuitry (e.g., control electrical circuitry 674 of FIGS. 6A-6B) can direct the power source 1740 to provide the first voltage to the first and second electrodes 1730*a* and 1730*b*, thereby enabling (e.g., diverting) a portion of the sample to flow across the first gap 1715*a* and into the dry waste region 1790. Enabling a portion of the sample to flow across the first gap 1715*a* decreases the volume or flow rate of the sample that reaches the second branch 1711*b*.

Figure 18:
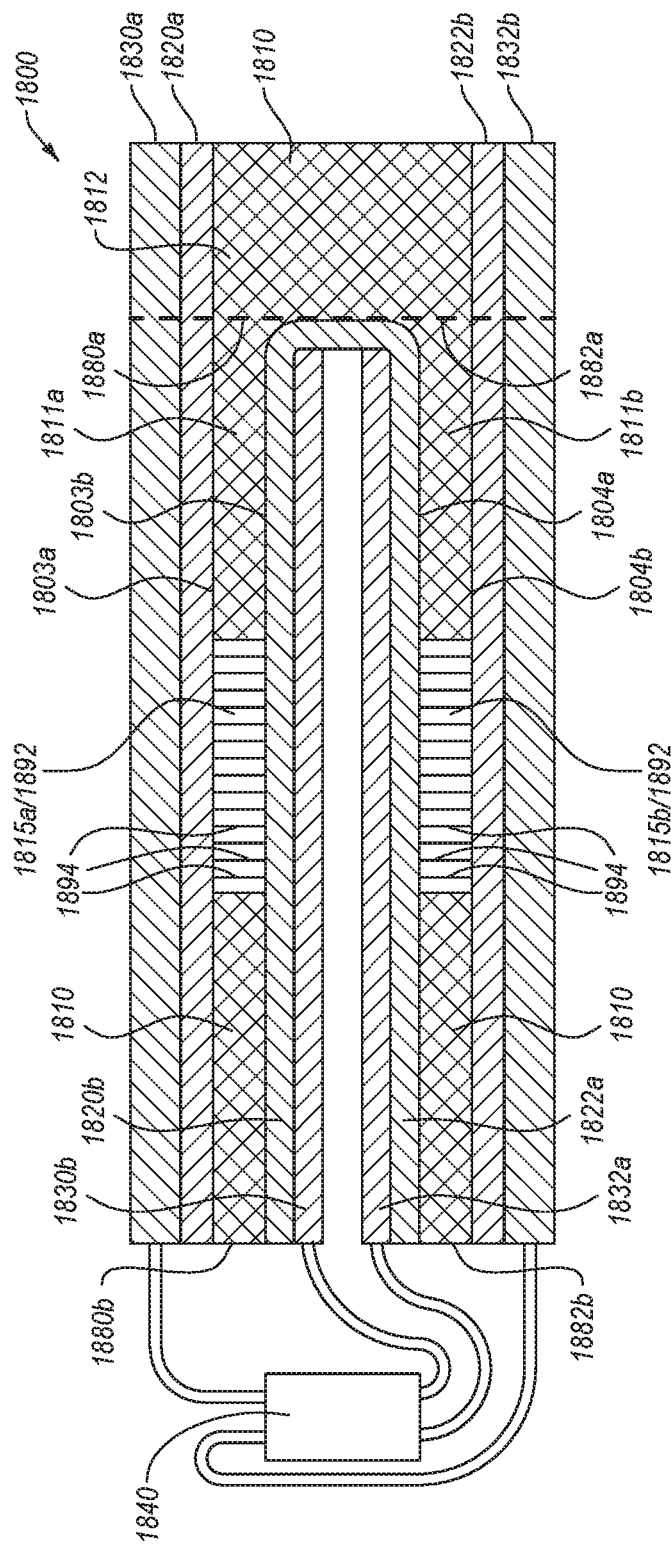
FIG. 18 is a front cross-sectional view of a flow assay according to an embodiment.

FIG. 18 illustrates a flow assay 1800 according to an embodiment. Except as otherwise disclosed herein, the flow assay 1800 is substantially the same as or similar to any of the flow assays disclosed herein. For example, the flow assay 1800 includes a proximal end 1801, at least one distal end 1802, common area 1812, at least one first branch 1811*a*, and at least one second branch 1811*b*. The first branch 1811*a* can include at least one hydrophilic porous layer 1810 extending from a first proximal branch end 1880*a* to a first distal branch end 1880*b*. The hydrophilic porous layer 1810 of the first branch 1811*a* includes a first side 1803*a*, a second side 1803*b*, and at least one first gap 1815*a*. The first branch 1811*a* also includes at least one first hydrophobic layer 1820*a*, at least one second hydrophobic layer 1820*b*, a first electrode 1830*a*, and a second electrode 1830*b*. Similarly, the second branch 1811*b* can include at least one hydrophilic porous layer 1810 extending from a second proximal branch end 1882*a* to a second distal branch end 1882*b*. The hydrophilic porous layer 1810 of the second branch 1811*b* includes a third side 1804*a*, a fourth side 1804*b*, and at least one second gap 1815*b*. The second branch 1811*b* also includes at least one third hydrophobic layer 1822*a*, at least one fourth hydrophobic layer 1822*b*, a third electrode 1832*a*, and a fourth electrode 1832*b*.

In an embodiment, the power source 1840 can provide a first voltage to the first and second electrodes 1830*a* and 1830*b* and a second voltage to the third and fourth electrodes 1832*a* and 1832*b*, thereby enabling the sample to flow across the first gap 1815*a* and the second gap 1815*b*. After a period of time, the power source 1840 can stop providing the first and second voltages to the first, second, third, and fourth electrodes 1830*a*, 1830*b*, 1832*a*, and 1832*b*. However, in some embodiments, the sample can continue to flow across the first or second gap 1815*a* or 1815*b* due to the surface tension or adhesion of the sample. Continuing to flow the sample across the first or second gap 1815*a* or 1815*b* can produce a false positive.

The flow assay 1800 can be configured to prevent the flow of a sample (e.g., a specific sample) across the first or second gap 1815*a* or 1815*b*. For example, the first and second gaps 1815*a* and 1815*b* can exhibit a first distance (not shown) and a second distance (not shown), respectively, between adjacent portions or segments of the hydrophilic porous layer 1810. At least one of the first or second distance is large enough to prevent the sample from flowing across the respective gap after the power source 1840 stops providing the first and second voltages. In another example, the first and second hydrophobic layers 1820*a* and 1820*b* collectively exhibit a first hydrophobicity and the third and fourth hydrophobic layers 1822*a* and 1822*b* collectively exhibit a second hydrophobicity. In such an example, at least one of the first or second hydrophobicity is sufficient to prevent the sample from flowing across the respective gap after the power source 1840 stops providing the first and second voltages. In another example, the first gap 1815*a* is at least partially occupied by a first hydrophobic material exhibiting a first hydrophobicity and the second gap 1815*b* is at least partially occupied by a second hydrophobic material exhibiting a second hydrophobicity. In such an example, at least one of the first or second hydrophobicity is sufficient to prevent the sample from flowing across the respective gap after the power source 1840 stops providing the first and second voltages.

In an embodiment, the flow assay 1800 can include at least one air vent 1892. The at least one air vent 1892 can be configured to flow air into the first or second gap 1815*a* or 1815*b*. The flow of air into the first or second gap 1815*a* or 1815*b* can decrease a probability that the sample will flow across the first or second gap 1815*a* or 1815*b* after the power source 1840 stops providing the first and second voltages. As such, the flow of air into the first or second gap 1815*a* or 1815*b* can decrease at least one of the first distance, the second distance, the collective hydrophobicity of the first and second hydrophobic layers 1820*a* and 1820*b*, the collective hydrophobicity of the third and fourth hydrophobic layers 1822*a* and 1822*b*, the hydrophobicity of the first hydrophobic material at least partially occupying the first gap 1815*a*, or the hydrophobicity of the second hydrophobic material at least partially occupying the second gap 1815*b* that is required to prevent the flow of the sample across the first or second gaps 1815*a* or 1815*b* when the power source 1840 stops providing the first and second voltage.

The air vent 1892 can be formed in the housing (e.g., the housing 150 of FIG. 1A) and permit air to flow from an exterior of the flow assay 1800 into an interior of the flow assay 1800. In an embodiment, the air vent 1892 can include a plurality of flaps 1894 that direct the air flow towards the first or second gaps 1815*a* or 1815*b*. In an embodiment, the air vent 1892 can be selectively opened and closed (e.g., the flaps 1894 can be selectively opened or closed). Selectively opening or closing the air vent 1892 can substantially prevent the air vent 1892 from affecting the flow of the sample across the first or second gaps 1815*a* or 1815*b* when the power source 1840 provides the first and second voltages. In an embodiment, the air vent 1892 can include an actuator (e.g., a blower, not shown) that is configured to force air from an exterior of the flow assay 1800 to an interior of the flow assay 1800.

Figure 19:
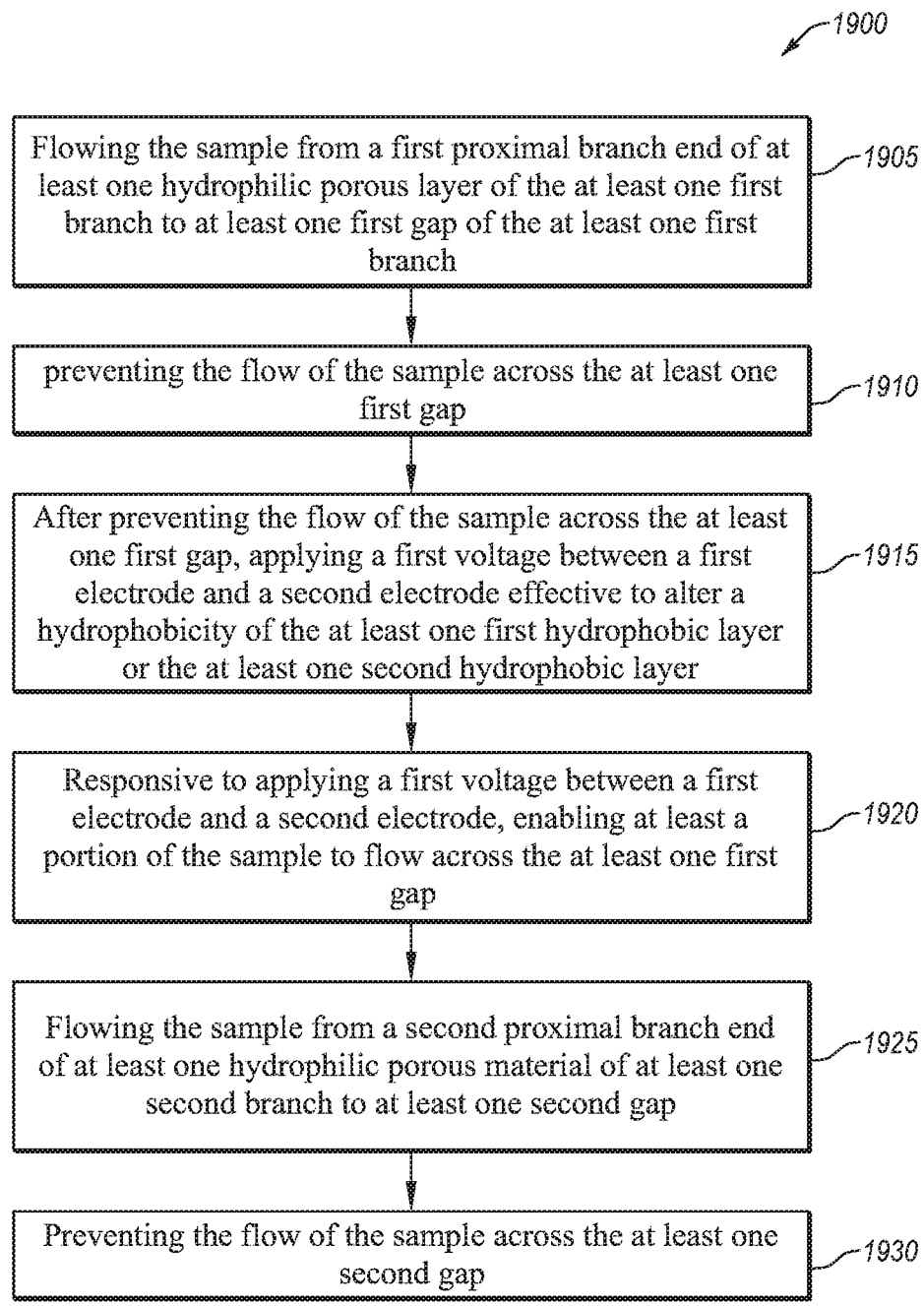
FIG. 19 is a schematic of a method of using a flow assay according to an embodiment.

FIG. 19 is a flow diagram of an embodiment of a method 1900 of detecting the presence of at least one analyte in a sample using any of the flow assays disclosed herein that include a plurality of branches (e.g., flow assays 800, 1000, 1100, 1200, 1300, 1400, 1500, 1600, 1700, and 1800 of FIGS. 8 and 10-18). The method 1900 can include flowing the sample through at least one first branch and flowing the sample at least partially through at least one second branch.

The method 1900 can include an act 1905 of flowing the sample from a first proximal branch end of at least one hydrophilic porous layer of the at least one first branch to at least one first gap of the at least one first branch. For example, the hydrophilic porous layer of the first branch includes a first proximal branch end, a first distal branch end that is spaced from the first proximal branch end, a first side spaced from a second side, and the first gap located between the first proximal branch end and the first distal branch end. The first gap is at least partially defined by a first distance between adjacent portions or segments of the hydrophilic porous layer of the first branch.

In an embodiment, the first branch includes at least one first conjugate or taggant disposed therein or thereon. In particular, the first branch can include the first conjugate or taggant disposed in or on a location of the hydrophilic porous layer of the first branch between the first proximal branch end and the first gap. In such an embodiment, act 1905 can include reacting the analyte with the first conjugate or taggant. For example, reacting the analyte with the first conjugate or taggant can include at least one of providing a visual indication of the presence of the analyte, causing at least one chemical reaction between the analyte and the first conjugate or taggant, or forming at least one analyte-conjugate complex from the analyte and the first conjugate.

The method 1900 can include an act 1910 of preventing the flow of the sample across the at least one first gap. For example, the first branch can include at least one first hydrophobic layer that is disposed adjacent to the first side that partially defines the first gap and at least one second hydrophobic layer that is disposed adjacent to the second side that partially defines the first gap. The presence of the first gap and the collective hydrophobicity of the first and second hydrophobic layers can form a first barrier that the sample cannot pass, at least until act 1915. The first gap can also include at least one first hydrophobic porous material disposed therein. The hydrophobicity of the first hydrophobic porous material can also form part of the first barrier.

In an embodiment, act 1910 can be performed for at least first period of time. The first period of time is selected to be sufficient to allow the analyte that may be present in the sample to react with at least one conjugate or taggant that is present in the flow assay (e.g., the first conjugate that is disposed in or on the first branch).

The method 1900 can include an act 1915 of, after preventing the flow of the sample across the at least one first gap, applying a first voltage between a first electrode and a second electrode effective to alter a hydrophobicity of the at least one first hydrophobic layer or the at least one second hydrophobic layer. For example, act 1915 includes generating an electric field between the first and second electrodes when the first voltage is applied to the first and second electrodes. The electric field can be effective to alter the hydrophobicity of the first hydrophobic layer or the second hydrophobic layer. The electric field can also be effective to alter the hydrophobicity of the first hydrophobic porous material. The power source can be configured to selectively apply the first voltage.

In an embodiment, act 1915 is performed a first selected time period after act 1910 started. The first selected time period is equal to or greater than the first period of time that is required to react the analyte with at least one conjugate or taggant that is present in the flow assay.

In an embodiment, act 1915 includes transmitting a first activation signal from control electrical circuitry of a control system and receiving the first activation signal at the power source. For example, the control electrical circuitry can transmit the first activation signal at the first selective time period. Responsive to receiving the first activation signal, the power source can apply the first voltage between the first and second electrodes.

In an embodiment, the power source applies the same voltage to the first and second electrodes and the third and fourth electrodes simultaneously. In such an embodiment, act 1915 includes applying the first voltage to the first and second electrodes and the third and fourth electrodes simultaneously. Applying the first voltage to the third and fourth electrodes may be sufficient to alter a hydrophobicity of at least a portion of a second barrier (e.g., at least one third hydrophobic layer, at least one fourth hydrophobic layer, or at least one second hydrophobic porous material) of the second branch. However, altering the hydrophobicity of at least a portion of the second barrier of the second branch may or may not be sufficient to enable the sample to flow across the second gap. In an embodiment, the power source selectively applies different voltage between the first and second electrodes and the third and fourth electrodes. In such an embodiment, act 1915 can include applying the first voltage between the first and second electrodes and a different voltage to the third and fourth electrodes simultaneously.

The method 1900 can include an act 1920 of, responsive to applying a first voltage between a first electrode and a second electrode, enabling at least a portion of the sample to flow across the at least one first gap. Flowing at least a portion of the sample across the first gap enables the sample the reach an indicator portion or at least one dry waste region.

In an embodiment, the first branch includes at least one first view area or indicator portion that is configured to detect a first concentration of the analyte. In such an embodiment, the method 1900 can include, after enabling at least a portion of the sample to flow across the at least one first gap, providing an indication that a first concentration of the at least one is or is not present at the at least one first viewing area or indicator strip. In an embodiment, the first branch includes at least one view area or indicator portion that is configured to detect at least one first analyte. The sample can also include at least one second analyte that is different than the first analyte. In such an embodiment, act 1095 can include, after enabling at least a portion of the sample to flow across the at least one first gap, providing an indication that the at least one first analyte is or is not present in the sample.

The method 1900 can include an act 1925 of flowing the sample from a second proximal branch end of at least one hydrophilic porous material of at least one second branch to at least one second gap. For example, the hydrophilic porous layer of the second branch includes a second proximal branch end, a second distal branch end that is spaced from the second proximal branch end, a third side spaced from a fourth side, and the second gap located between the second proximal branch end and the second distal branch end. The second gap is at least partially defined by a second distance between adjacent portions of segments of the hydrophilic porous layer of the first branch. The second distance can be the same as, similar to, or different than the first distance.

In an embodiment, the second branch includes at least one second conjugate or taggant disposed therein or thereon. In particular, the second branch can include the second conjugate or taggant disposed in or on a location of the hydrophilic porous layer of second first branch between the second proximal branch end and the second gap. In such an embodiment, act 1925 can include reacting the analyte with the second conjugate or taggant. For example, reacting the analyte with the second conjugate can include at least one of providing a visual indication of the presence of the analyte, causing at least one chemical reaction between the analyte and the second conjugate or taggant, or forming at least one analyte-conjugate complex from the analyte and the second conjugate. In an embodiment, the second conjugate or taggant is the same as the first conjugate or taggant. In such an embodiment, act 1925 can include reacting the second conjugate or taggant with the same analyte and in the same manner as in act 1905. In an embodiment, the second conjugate or taggant is different than the first conjugate or taggant. In such an embodiment, act 1925 can include reacting the second conjugate with a different analyte in a different manner as in act 1905.

The method 1900 can include an act 1930 of preventing the flow of the sample across the at least one second gap. For example, the second branch can include at least one third hydrophobic layer that is disposed adjacent to the third side that partially defines the second gap and at least one fourth hydrophobic layer that is disposed adjacent to the fourth side that partially defines the second gap. The presence of the second gap and the collective hydrophobicity of the third and fourth hydrophobic layers can provide a second barrier that the sample cannot pass, at least until a second voltage is provided to electrodes of the second branch. The second gap can also include at least one second hydrophobic porous material disposed therein. The hydrophobicity of the second hydrophobic porous material can also form part of the second barrier.

In an embodiment, act 1930 can be performed for at least second period of time. The second period of time is selected to be sufficient to allow the analyte that may be present in the sample to react with at least one conjugate or taggant that is present in the flow assay (e.g., the second conjugate or taggant that is disposed in or on the second branch).

The method 1900 can include, after preventing the flow of the sample across the at least one second gap, applying a second voltage between a third electrode and a fourth electrode effective to alter a hydrophobicity of the at least one third hydrophobic layer or the at least one fourth hydrophobic layer. For example, the method 1900 includes generating an electric field between the third and fourth electrodes when the second voltage is applied to the third and fourth electrodes. The electric field can be effective to alter the hydrophobicity of the third hydrophobic layer or the fourth hydrophobic layer. The electric field can also be effective to alter the hydrophobicity of the second hydrophobic porous material.

In an embodiment, the method 1900 includes performing the act of applying a second voltage between a third electrode and a fourth electrode at a second selected time period after act 1930 started. The second selected time period is equal to or greater than the second period of time that is required to react the analyte with at least one conjugate or taggant that is present in the flow assay.

In an embodiment, the method 1900 includes transmitting a second activation signal from control electrical circuitry of a control system and receiving the second activation signal at the power source. For example, the control electrical circuitry can transmit the second activation signal at the second selective time period after act 1930 started. Responsive to receiving the second activation signal, the power source applies the second voltage between the first and second electrodes.

In an embodiment, as previously discussed, the power source applies the same voltage to the first and second electrodes and the third and fourth electrodes simultaneously. In such an embodiment, the method 1900 also includes applying the second voltage to the first and second electrodes which may be sufficient to alter a hydrophobicity of at least a portion of the first barrier of the first branch. However, altering the hydrophobicity of at least a portion of the first barrier of the first branch may or may not be sufficient to enable the sample to flow across the first gap. In an embodiment, the power source applies different voltage between the first and second electrodes and the third and fourth electrodes simultaneously or temporally separately.

It is noted that in some embodiments, the method 1900 does not include applying a second voltage to the third and fourth electrodes. For example, the first branch is configured to detect a first characteristic of the sample and the second branch is configured to detect a second characteristic of the sample. In such an example, a user of the flow assay can determine that only the first characteristic needs to be determined and, as such, the method 1900 does not include applying a second voltage to the third and fourth electrodes.

The method 1900 can include, responsive to applying a second voltage between a third electrode and a fourth electrode, enabling at least a portion of the sample to flow across the at least one second gap. Flowing at least a portion of the sample across the enables the sample the reach at least one viewing area or indicator strip or at least one dry waste region that is disposed on or in the second branch.

In an embodiment, the second branch includes at least one second view area or indicator portion at or near the second distal branch end that is configured to detect a second concentration of the analyte. The second concentration is different than the first concentration that was previously discussed. In such an embodiment, the method 1900 can include, after enabling at least a portion of the sample to flow across the at least one second gap, providing an indication that the second concentration of the at least one analyte is or is not present in the sample. In an embodiment, the second view area or indicator portion is configured to detect at least one second analyte that can be present in the sample. The second analyte can be different than the first analyte that was previously discussed. In such an embodiment, the method 1900 can include, after enabling at least a portion of the sample to flow across the at least one second gap, providing an indication that the at least one second analyte is or is not present in the sample.

In an embodiment, the second branch can include at least one dry waste region positioned at or near the second distal branch end. In such an embodiment, the method 1900 can include, after enabling at least a portion of the sample to flow across the at least one second gap, storing at least a portion of the sample that flowed across the at least one second gap in the dry waste region. In an embodiment, enabling at least a portion of the sample to flow across the at least one second gap (e.g., storing at least a portion of the sample that flowed across the at least one second gap in the dry waste region) includes reducing a volume or flow rate of the sample flowing into the first branch.

The method 1900 can include introducing the sample at at least one common area that is fluidly coupled to the first proximal branch end of the at least one first branch and the second proximal branch end of the at least one second branch. Introducing the sample to at the common area can cause acts 1905 and 1925 to occur.

In an embodiment, the common area can include at least one third conjugate or taggant disposed therein or thereon. The third conjugate or taggant can react with at least one analyte that is present in the sample by at least one of providing an indication that the analyte is or is not present in the sample, causing a chemical reaction between the analyte and the third conjugate or taggant, or forming at least one analyte-conjugate complex with the analyte and the third conjugate. For example, the third conjugate or taggant can be the same as or similar to the first or second conjugate or taggant that is present in the first or second branch, respectively. In such an example, the third conjugate or taggant can react with the same analyte and in the same manner as the first or second conjugate or taggant. In another example, the third conjugate or taggant can be different than the first or second conjugate or taggant that is present in the first or second branch. In such an example, the third conjugate or taggant can react with a different analyte or in a different manner than the first or second conjugate or taggant. In another example, the first or second branch does not include the first or second conjugate or taggant. In such an example, the third conjugate or taggant reacts with the analyte instead of the first or second conjugate or taggant.

In an embodiment, the method 1900 can include, after applying the first voltage between the first and second electrodes, ceasing to apply the first voltage between the first and second electrodes. In an embodiment, the method 1900 can include, after applying the second voltage between the third and fourth electrodes, creasing to apply the second voltage between the third and fourth electrodes. In either embodiment, ceasing to apply the first or second voltages to the first, second, third, or fourth electrodes can cause the sample to stop flowing across the first or second gaps. In an embodiment, air can be flowed into the first or second gaps (e.g., using an air vent) to cause the sample to stop flowing across the first or second gaps.

In an embodiment, the flow assay can include three or more branches, such as the first branch, the second branch, and one or more additional branches. The one or more additional branches can be positioned in parallel with the first and second branches (e.g., the third branch 1511*c* of FIG. 15) or in series with at least one of the first and second branches (e.g., the third and fourth branches 1611*c* and 1611*d* of FIG. 16). In such an embodiment, the method 1900 can include operating the one or more additional branches in substantially the same manner as at least one of acts 1905, 1910, 1915, 1920, 1925, or 1930, or another of the other acts disclosed herein. For example, the method 1900 can include at least one of flowing a sample into the one or more additional branches, preventing the flow of the sample across at least one gap of the one or more additional branches, applying one or more additional voltages to electrodes of the one or more additional branches, or enabling the flow of at least a portion of the sample across the gap of the one or more additional branches.

WORKING EXAMPLE

A working example of a flow assay was made using nitrocellulose paper as a hydrophilic porous layer, with the nitrocellulose paper having a gap filled with air therein. The nitrocellulose paper was bordered (e.g., sandwiched) by a layer of hydrophobic trichloro(perfluorooctyl)silane extending past each side of the gap. Each layer of trichloro (perfluorooctyl)silane was electrically connected to a layer of transparent indium tin oxide disposed thereon. The transparent indium tin oxide was connected to a 9 volt power source.

A potassium chloride salt solution was applied to the nitrocellulose paper. The solution progressed through the nitrocellulose paper to the gap therein. The solution did not progress past the gap. The solution stayed at the gap without progressing for more than 10 minutes. A voltage of about 9V (DC) was applied across the electrodes. Upon application of the voltage, the solution progressed across the gap and on toward the proximal end of the flow assay. Once the solution crossed the gap the application of voltage was discontinued and the progression of the solution continued.

The reader will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. The reader will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. The reader will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein may be implemented in an analog or digital fashion or some combination thereof.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components may be referred to herein as "configured to." The reader will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, the recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. A flow assay comprising:
   at least one common area;
   at least one first branch and at least one second branch extending longitudinally from and fluidly coupled to the at least one common area, each of the at least one first branch and the at least one second branch including:
      at least one hydrophilic porous layer including a proximal branch end adjacent to the at least one common area, a distal branch end spaced from the proximal branch end, a first branch side spaced from a second branch end, and at least one gap located between the proximal branch end and the distal branch end;
      at least one first hydrophobic layer disposed adjacent to the first branch side to partially define the at least one gap;
      at least one second hydrophobic layer disposed adjacent to the second branch side to partially define the at least one gap;
      a first electrode separated from the at least one hydrophilic porous layer by the at least one first hydrophobic layer; and
      a second electrode separated from the at least one hydrophilic porous layer by the at least one second hydrophobic layer; and
   a power source electrically coupled to the first and second electrodes; the power source configured to generate:
      a first voltage between the first electrode and the second electrode of the at least one first branch to enable at least a portion of the sample to flow across the at least one gap of the at least one first branch; and
      a second voltage between the first electrode and the second electrode of the at least one second branch to enable at least a portion of the sample flow across the at least one gap of the at least one second branch, wherein the second voltage is different than the first voltage.

2. The flow assay of claim 1, wherein:
   the at least one gap of the at least one first branch is at least partially defined by a first distance between adjacent portions or segments of the at least one hydrophilic porous layer of the at least one first branch; and
   the at least one gap of the at least one second branch is at least partially defined by a second distance between adjacent portions or segments of the at least one hydrophilic porous layer of the at least one second branch, wherein the second distance is less than the first distance.

3. The flow assay of claim 2, wherein one of the first or second distance is at least 0.1 inches greater than the other of the first or second distance.

4. The flow assay of claim 1, wherein:
   the at least one gap of the at least one first branch is at least partially filled with at least one first hydrophobic porous material, the at least one first hydrophobic porous material exhibiting a first hydrophobicity; and the at least one gap of the at least one second branch is at least partially filled at least one second hydrophobic porous material, the at least one second hydrophobic porous material exhibiting a second hydrophobicity that is different than the first hydrophobicity.

5. The flow assay of claim 4, wherein at least one of:
the at least one first hydrophobic porous material is different than the at least one first hydrophobic layer of the at least one first branch or the at least one second hydrophobic layer of the at least one first branch; or
the at least one second hydrophobic porous material is different than the at least one first hydrophobic layer of the at least one second branch or the at least one second hydrophobic layer of the at least one second branch.

6. The flow assay of claim 1, wherein the at least one gap of the at least one first branch is at least partially filled with at least one hydrophobic porous material and the at least one gap of the at least one second gap is at least partially occupied by air.

7. The flow assay of claim 1, wherein the at least one first branch or the at least one second branch includes an air vent configured to flow air into the at least one gap of the at least one first branch or the at least one gap of the at least one second branch, respectively.

8. The flow assay of claim 1, wherein:
the at least one first hydrophobic layer and the at least one second hydrophobic layer of the at least one first branch exhibits a first hydrophobicity; and
the at least one first hydrophobic layer and the at least one second hydrophobic layer of the at least one second branch exhibits a second hydrophobicity that is different than the first hydrophobicity.

9. The flow assay of claim 1, wherein:
the at least one first hydrophobic layer and the at least one second hydrophobic layer of the at least one first branch include at least one first material; and
the at least one first hydrophobic layer and the at least one second hydrophobic layer of the at least one second branch include at least one second material that is different than the at least one first material.

10. The flow assay of claim 1, wherein the at least one first branch or the at least one second branch includes at least one insulating layer disposed between the first or second electrodes and the corresponding one of the at least one first hydrophobic layer or the at least one second hydrophobic layer.

11. The flow assay of claim 1, wherein the first electrode and the second electrode of the at least one first branch is electrically coupled to the at least one first hydrophobic layer or the at least one second hydrophobic layer.

12. The flow assay of claim 1, wherein:
the at least one first branch includes at least one view area or indicator strip between the at least one gap of the at least one first branch and the distal branch end of the at least one first branch; and
the at least one second branch includes at least one view area or indicator strip between the at least one gap of the at least one second branch and the distal branch end of the at least one second branch.

13. The flow assay of claim 12, wherein:
the at least one view area of indicator strip of the at least one first branch is configured to detect whether at least one first analyte is or is not present in the sample; and
the at least one view area of indicator strip of the at least one second branch is configured to detect whether at least one second analyte is or is not present in the sample, wherein the at least one second analyte is different than the at least one first analyte.

14. The flow assay of claim 12, wherein:
the at least one view area of indicator strip of the at least one first branch is configured to detect whether a first concentration of at least one analyte is or is not present in the sample; and
the at least one view area of indicator strip of the at least one second branch is configured to detect whether a second concentration of the at least one analyte is or is not present in the sample, wherein the second concentration is different than the first concentration.

15. The flow assay of claim 1, wherein the at least one second branch includes at least one dry waste region between the at least one gap and the distal branch end thereof, the at least one dry waste region configured to receive and store at least one fluid therein.

16. The flow assay of claim 1, wherein:
the at least one first branch includes at least one first conjugate or taggant located between the proximal branch end of the at least one first branch and the at least one gap of the at least one first branch; and
the at least one second branch includes at least one second conjugate or taggant located between the proximal branch end of the at least one second branch and the at least one gap of the at least one second branch.

17. The flow assay of claim 16, wherein the at least one first conjugate or taggant is different than the at least one second conjugate or taggant.

18. The flow assay of claim 17, wherein:
the at least one first conjugate or taggant is configured to at least one of provide an indication of at least one first analyte when the at least one first analyte is present in the sample, cause a chemical reaction with the at least one first analyte, or form at least one analyte-conjugate complex with the at least one first analyte; and
the at least one second conjugate or taggant is configured to at least one of provide an indication of at least one second analyte when the at least one second analyte is present in the sample, cause a chemical reaction with the at least one second analyte, or form at least one analyte-conjugate complex with the at least one second analyte, wherein the at least one second analyte is different than the at least one first analyte.

19. The flow assay of claim 1, further comprising one or more additional branches that are positioned to be in parallel with the at least one first branch and the at least one second branch.

20. The flow assay of claim 1, further comprising one or more additional branches that are positioned to be in series with the at least one first branch or the at least one second branch.

21. The flow assay of claim 20, wherein the one or more additional branches includes at least one third branch and at least one fourth branch that is fluidly coupled to the at least one first branch, the at least one third branch and the at least one fourth branch extending longitudinally from a location at or near the distal branch end of the at least one first branch, each of the at least one third branch and the at least one fourth branch including:
at least one hydrophilic porous layer including a proximal branch end adjacent to the distal branch end of the at least one first branch, a distal branch end spaced from the proximal branch end, a first branch side spaced from a second branch end, and at least one gap located between the proximal branch end and the distal branch end;

at least one first hydrophobic layer disposed adjacent to the first side of the at least one hydrophilic porous layer to partially define the at least one gap;

at least one second hydrophobic layer disposed adjacent to the second side of the at least one hydrophilic porous layer to partially define the at least one gap;

a first electrode separated from the at least one hydrophilic porous layer by the at least one first hydrophobic layer; and a second electrode separated from the at least one hydrophilic porous layer by the at least one second hydrophobic layer.

22. The flow assay of claim 21, wherein the power source is electrically coupled to the first and second electrodes of the at least one third and fourth branches, the power source configured to generate:

a third voltage between the first electrode and the second electrode of the at least one third branch to enable at least a portion of the sample to flow across the at least one gap of the at least one third branch; and a fourth voltage between the first electrode and the second electrode of the at least one fourth branch to enable at least a portion of the sample to flow across the at least one gap of the at least one fourth branch, wherein the fourth voltage is different than the third voltage.

23. The flow assay of claim 1, further comprising a control system including control electrical circuitry configured to activate the power source after one or more selected time periods, wherein the power source generates the first or second voltage when activated.

24. The flow assay of claim 23, further comprising one or more sensors positioned at least proximate to the at least one gap of the at least one first branch or the at least one second branch, the one or more sensors configured to sense a presence of the sample at or near the at least one gap of the at least one first branch or the at least one second branch, the one or more sensors operably coupled to the control system and configured to output one or more sensing signals to the control electrical circuitry responsive to detecting the presence of the sample.

25. The flow assay of claim 24, wherein the one or more sensors includes one or more capacitance sensors.

26. The flow assay of claim 23, wherein the control electrical circuitry is configured to send a first activation signal to the power source after a first selected time period and a second activation signal to the power source after a second selected time period that is different than the first selected time period, wherein the first activation signal causes the power source to generate the first voltage and the second activation signal causes the power source to generate the second voltage.

27. The flow assay of claim 1, further comprising a housing at least partially enclosing at least a portion of one or more of the at least one common area, the at least one first branch, the at least one second branch, or the power source.

28. A method to detect a presence of at least one analyte in a sample, the method comprising:

flowing the sample through at least one first branch including, flowing the sample from a first proximal branch end of at least one hydrophilic porous layer of the at least one first branch to at least one first gap, the at least one first gap located between the first proximal branch end and a first distal branch end that is spaced from the first proximal branch end, the at least one hydrophilic porous layer of the at least one first branch including a first branch side spaced from a second branch side;

preventing the flow of the sample across the at least one first gap because of at least:

at least one first hydrophobic layer that is disposed adjacent to the first branch side and partially defining the at least one first gap; and at least one second hydrophobic layer that is disposed adjacent to the second branch side and partially defining the at least one first gap;

after preventing the flow of the sample across the at least one first gap, applying a first voltage between a first electrode and a second electrode effective to alter a hydrophobicity of the at least one first hydrophobic layer or the at least one second hydrophobic layer, the first electrode separated from the at least one first hydrophilic porous layer of the at least one first branch by the at least one first hydrophobic layer, the second electrode separated from the at least one first hydrophilic porous layer of the at least one first branch by the at least one second hydrophobic layer; and responsive to applying a first voltage between a first electrode and a second electrode, enabling at least a portion of the sample to flow across the at least one first gap; and flowing the sample at least partially through at least one second branch including, flowing the sample from a second proximal branch end of at least one hydrophilic porous layer of the at least one second branch to at least one second gap, the at least one second gap located between the second proximal branch end and a second distal branch end that is spaced from the second proximal branch end, the at least one hydrophilic porous layer of the at least one second branch including a third branch side spaced from a fourth branch side; and preventing the flow of the sample across the at least one second gap because of at least:

at least one first hydrophobic layer that is disposed adjacent to the third branch side to partially define the at least one second gap; and at least one second hydrophobic layer that is disposed adjacent to the fourth branch side to partially define the at least one second gap.

29. The method of claim 28, wherein flowing the sample at least partially through the at least one second branch includes:

after preventing the flow of the sample across the at least one second gap, applying a second voltage that is different than the first voltage between a third electrode and a fourth electrode effective to alter a hydrophobicity of one or more of the at least one third hydrophobic layer or the at least one fourth hydrophobic layer, the third electrode separated from the at least one hydrophilic porous layer of the at least one second branch by the at least one third hydrophobic layer, the fourth electrode separated from the at least one hydrophilic porous layer of the at least one second branch by the at least one fourth hydrophobic layer; and responsive to applying a second voltage between a third electrode and a fourth electrode, enabling at least a portion of the sample to flow across the at least one second gap.

30. The method of claim 29, further comprising:
after enabling at least a portion of the sample to flow across the at least one first gap, providing an indication that a first concentration of the at least one analyte is or is not present at a first view area or indicator strip, the first view area or indicator strip is located at or near the first distal branch end; and
after enabling at least a portion of the sample to flow across the at least one second gap, providing an indication that a second concentration of the at least one analyte is or is not present at a second view area or indicator strip, the second view area or indicator strip is located at or near the second distal branch end, wherein the second concentration of the at least one analyte is different than the first concentration of the at least one analyte.

31. The method of claim 29, further comprising:
after enabling at least a portion of the sample to flow across the at least one first gap, providing an indication that at least one first analyte is or is not present at a first view area or indicator strip, the first view area or indictor strip is located at or near the first distal branch end; and
after enabling at least a portion of the sample to flow across the at least one second gap, providing an indication that at least one second analyte is or is not present at a second view area or indicator strip, the second view area or indicator strip is located at or near the second distal branch end, wherein the at least one second analyte is different than the at least one second analyte.

32. The method of claim 29, wherein:
the act of applying a first voltage between a first electrode and a second electrode is performed a first selected time period after a start of the act preventing the flow of the sample across the at least one first gap; and
the act of applying a second voltage between a third electrode and a fourth electrode is performed a second selected time period after a start of the act of preventing the flow of the sample across the at least one second gap, wherein the second selected time period is different than the first selected time period.

33. The method of claim 29, further comprising:
transmitting a first activation signal from control electrical circuitry of a control system and receiving the first activation signal at a power source;
responsive to receiving the first activation, the power source applies the first voltage between the first electrode and the second electrode;
transmitting a second activation signal from the control electrical circuitry of the control system and receiving the second activation signal at the power source; and
responsive to receiving the second activation, the power source applies the second voltage between the third electrode and the fourth electrode.

34. The method of claim 28, wherein:
flowing the sample through the at least one first branch includes at least one of providing an indication of the presence of the at least one analyte with at least one first conjugate or taggant, causing a chemical reaction between the at least one analyte and the at least one first conjugate or taggant, or forming at least one first analyte-conjugate complex from the at least one analyte and the at least one first conjugate or taggant, wherein the at least one first conjugate taggant is located in the at least one first branch between the first proximal branch end and the at least one first gap; and flowing the sample at least partially through the at least one second branch includes at least one of providing an indication of the presence of the at least one analyte with at least one second conjugate or taggant, causing a chemical reaction between the at least one analyte and the at least one second conjugate or taggant, or forming at least one second analyte-conjugate complex from the at least one analyte and the at least one second conjugate or taggant, wherein the at least one second conjugate taggant is located in the at least one second branch between the second proximal branch end and the at least one second gap;
wherein the at least one first conjugate or taggant is different than the at least one second conjugate or taggant.

35. The method of claim 28, further comprising storing at least a portion of the sample that flowed across the at least one first gap or the at least one second gap in at least one dry waste region.

36. The method of claim 35, wherein storing at least a portion of the sample that flowed across the at least one first gap or the at least one second gap includes reducing a flow rate of the sample.

37. The method of claim 28, further comprising, after applying a first voltage between a first electrode and a second electrode, ceasing to apply the first voltage between the first electrode and the second electrode.

38. The method of claim 37, further comprising, after ceasing to apply the first voltage between the first electrode and the second electrode, preventing the flow of the sample across the at least one first gap.

39. A flow assay for detecting a presence of an analyte in a sample, the flow assay comprising:
at least one common area;
at least one first branch and at least one second branch extending longitudinally from the at least one common area, each of the at least one first branch and the at least one second branch including:
at least one hydrophilic porous layer including a proximal branch end adjacent to the at least one common area, a distal branch end spaced from the proximal branch end, a first branch side spaced from a second branch end, and at least one gap located between the proximal branch end and the distal branch end;
at least one first hydrophobic layer disposed adjacent to the first side of the at least one hydrophilic porous layer to partially define the at least one gap;
at least one second hydrophobic layer disposed adjacent to the second side of the at least one hydrophilic porous layer to partially define the at least one gap;
a first electrode electrically coupled to the at least one first hydrophobic layer and separated from the at least one hydrophilic porous layer by the at least one first hydrophobic layer; and
a second electrode electrically coupled to the at least one second hydrophobic layer and separated from the at least one hydrophilic porous layer by the at least one second hydrophobic layer;
a power source electrically coupled to the first and second electrodes; the power source configured to generate:
a first voltage between the first electrode and the second electrode of the at least one first branch; and
a second voltage between the first electrode and the second electrode of the at least one second branch, wherein the second voltage is different than the first voltage; and a control system including control electrical circuitry communicably coupled to the power source, the control electrical circuitry configured to transmit:
   a first activation signal to the power source that is configured to cause the power source to generate the first voltage; and
   a second activation signal to the power source that is configured to cause the power source to generate the second voltage;
wherein at least one of:
   the at least one gap of the at least one first branch exhibits distance between adjacent portions or segments of the at least one hydrophilic porous layer of the at least one first branch and the at least one gap of the at least one second branch is at least partially defined by a second distance between adjacent portions or segments of the at least one hydrophilic porous layer of the at least one second branch, wherein the second distance is less than the first distance;
   the at least one first hydrophobic layer and the at least one second hydrophobic layer of the at least one first branch collectively exhibit a third hydrophobicity and the at least one first hydrophobic layer and the at least one second hydrophobic layer of the at least one second branch collectively exhibit a fourth hydrophobicity that is different than the third hydrophobicity;
   the at least one gap of the at least one first branch is at least partially occupied by at least one first hydrophobic porous material exhibiting a first hydrophobicity and the at least one gap of the at least one second branch is at least partially occupied by at least one second hydrophobic porous material exhibiting a second hydrophobicity that is different than the first hydrophobicity; or
   the at least one gap of the at least one first branch is at least partially occupied by at least one hydrophobic porous material and the at least one gap of the at least one second branch is at least partially occupied by air.

* * * * *